(12) United States Patent
Hashida et al.

(10) Patent No.: US 7,172,867 B2
(45) Date of Patent: Feb. 6, 2007

(54) METHODS OF TESTING FOR ALLERGIC DISEASES, AND THERAPEUTIC AGENTS FOR TREATING SAME

(75) Inventors: Ryoichi Hashida, Tsukuba (JP); Shinji Kagaya, Tokyo (JP); Yuji Sugita, Tsukuba (JP); Hirohisa Saito, Tokyo (JP)

(73) Assignees: Genox Research, Inc., Ibaraki (JP); Japan as Represented by General Director of Agency of National Center for Child Health & Development, Tokyo (JP)

( * ) Notice: Subject to any disclaimer, the term of this patent is extended or adjusted under 35 U.S.C. 154(b) by 58 days.

(21) Appl. No.: 10/611,310

(22) Filed: Jul. 1, 2003

(65) Prior Publication Data

US 2004/0214231 A1    Oct. 28, 2004

(30) Foreign Application Priority Data

Jul. 2, 2002    (JP)    ............................. 2002-193841

(51) Int. Cl.
*C12Q 1/68* (2006.01)
*C12P 19/34* (2006.01)
(52) U.S. Cl. ......................................... 435/6; 435/91.2
(58) Field of Classification Search .................. 435/6
See application file for complete search history.

(56) References Cited

U.S. PATENT DOCUMENTS

| | | | |
|---|---|---|---|
| 6,312,949 B1 | 11/2001 | Sakurada et al. | |
| 6,500,938 B1 * | 12/2002 | Au-Young et al. | ......... 536/23.1 |
| 2002/0049151 A1 | 4/2002 | Murphy et al. | |
| 2004/0214192 A1 | 10/2004 | Hashida et al. | |

FOREIGN PATENT DOCUMENTS

| | | |
|---|---|---|
| EP | 1185647 A1 | 12/2000 |
| EP | 1265628 A1 | 9/2001 |
| EP | 1287019 A1 | 11/2001 |
| WO | WO 00/58451 A1 | 10/2000 |
| WO | WO 00/77202 A1 | 12/2000 |
| WO | WO 200077202 A1 * | 12/2000 |
| WO | WO 01/70254 A1 | 9/2001 |
| WO | WO 01/87923 A1 | 11/2001 |

OTHER PUBLICATIONS

Haynes et al., Electrophoresis 1998, vol. 19(11): pp. 1862-1871, esp. p. 1863: section 2.1.*
Nakajima T, et al. Gene expression screening of human mast cells and eosinophils using high-density oligonucleotide probe arrays: abundant expression of major basic protein in mast cells. Blood. Aug. 15, 2001;98(4):1127-34.*
Paulsen, R. E., C. A. Weaver, T. J. Fahrner, and J. Milbrandt. 1992. Domains regulating transcriptional activity of the inducible orphan receptor NGFI-B. J. Biol. Chem. 267:16491-16496.*
Maira, et al., Heterodimerization between Members of the Nur Superfamily of Orphan Nuclear Receptors as a Novel Mechanism for Gene Activation. Mol Cell Bio. Nov. 1999, p. 7549-7557.*
Mages et al., NOT, a human intermediate-early response gene closely related to the steroid/thyroid hormone receptor NAK1/TR3. Mol Endocrinol. Nov. 1994; 8(11):1583-91.*
Wedi et al., J Allergy Clin Immunol Oct. 1997;100(4):536-43, Abstract only.*
Salin-Nordstrom et al., Society for Neuroscience Abstracts, Society for Neuroscience 1999;25(1/02):p. 1754, abstract 696.3.*
Kim, S.O., et al., "Orphan Nuclear Receptor Nur77 Is Involved in Caspase-independent Macrophage Cell Death," *J. Exp. Med.*, 197(11):1441-1452 (2003).
Wang, Z., et al., "Structure and function of Nurr1 identifies a class of ligand-independent nuclear receptors," *Nature*, 423:555-560 (2003).

* cited by examiner

*Primary Examiner*—Marianne P. Allen
*Assistant Examiner*—Cherie Woodward
(74) *Attorney, Agent, or Firm*—Hamilton, Brook, Smith & Reynolds, P.C.

(57) ABSTRACT

Differential expression of genes whose expression is different in the activated eosinophils of atopic dermatitis patients was measured by comparative analysis using a gene chip. As a result, the TR3 and TINUR genes, whose expression is significantly elevated in activated eosinophils, were successfully identified. The present inventors discovered that these genes can be used to test for allergic disease and to screen candidate compounds for therapeutic agents for allergic disease.

2 Claims, 15 Drawing Sheets

METHODS OF TESTING FOR ALLERGIC DISEASES, AND THERAPEUTIC AGENTS FOR TREATING SAME

RELATED APPLICATION

This application claims priority under 35 U.S.C. § 119 or 365 to Japan Application No. 2002-193841, filed Jul. 2, 2002. The entire teachings of the above application are incorporated herein by reference.

FIELD OF THE INVENTION

The present invention relates to methods of testing for allergic diseases, and methods of screening candidate compounds for therapeutic agents for allergic diseases, using the expression of the allergic disease-related TR3 or "TINUR genes as an index. The present invention is also directed to pharmaceutical agents for treating allergic diseases.

BACKGROUND OF THE INVENTION

Allergic diseases such as atopic dermatitis are considered to be multifactorial diseases. Multifactorial diseases are caused by the interaction of many different genes, the expression of each of which is independently influenced by multiple environmental factors. Thus, determining the specific genes that cause a specific allergic disease is extremely difficult.

Allergic diseases are generally presumed to be associated with the expression of genes having mutations or defects, and/or with the overexpression or reduced expression of specific genes. To determine the role of gene expression in a disease, it is necessary to understand how genes are involved in the onset of that disease, and how gene expression is altered by external stimulants such as drugs.

Recent developments in gene expression analysis techniques have enabled analysis and comparison of gene expression in multiple clinical samples. As an example of such methods, the differential display (DD) method is useful. Liang and Pardee originally developed this method in 1992 (Science, 1992, 257: 967–971). By using this method, several dozen or more samples can be screened at one time, thereby enabling the detection of genes whose expression in one sample differs from other samples. Information essential to determining the causative gene(s) of a disease is expected to be obtained by examining genes with mutations, or genes whose expression changes depending on time and the environment, including genes whose expression is influenced by environmental factors.

Recently, patient interviews and patient medical and family history have become important factors in the diagnosis of allergic disease. More objective methods of diagnosing allergies include testing patient blood samples and observing patient immune response to allergen(s). Examples of the former method include allergen-specific IgE measurement, the leukocyte histamine release test and the lymphocyte blast transformation test. The presence of allergen-specific IgE is evidence of an allergic reaction against an allergen. However, allergen-specific IgE is not always detected in every patient. Furthermore, in principle, IgE assaying requires tests to be performed on all of the allergens necessary for diagnosis. The leukocyte histamine release test and the lymphocyte blast transformation test are methods for observing immune system reaction towards a specific allergen in vitro. Operation of these methods is complex.

Another known method useful in allergy diagnosis is based on the immune response observed when a patient contacts an allergen (i.e., the latter method). Such tests include the prick test, scratch test, patch test, intradermal reaction and induction test. These tests allow direct diagnosis of a patient's allergic reaction, but are highly invasive as patients are actually exposed to allergens.

Methods of confirming the involvement of an allergic reaction, regardless of allergen type, are also being trialed. For example, a high serum IgE titer indicates an allergic reaction in a patient. The serum IgE titer corresponds to the total amount of allergen-specific IgE. Determining the total amount of IgE is simple, regardless of the type of allergen; however, IgE titer may be reduced in some patients, for example, in those with non-atopic bronchitis.

The number of eosinophils and the level of eosinophil cationic protein (ECP) are diagnostic items for delayed-type reactions following Type I allergy-and allergic inflammatory reactions. The number of eosinophils is considered to reflect the progress of allergic symptoms. ECP, a protein contained in eosinophil granules, is also strongly activated in patients having an asthma attack. Although allergic symptoms can indeed be identified using these diagnostic items, the extent to which they can actually be used as diagnostic indices is limited.

Therefore, diagnostic indices useful in understanding pathological conditions in patients with allergic diseases, and in determining treatment regimens for such diseases, regardless of the type of allergen, have been greatly sought after. Allergic disease markers that are less risky for patients and capable of readily providing information required for diagnosis would be of great use. If genes associated with allergic disease can be identified, the expression of such genes can be used as an index to test for allergic diseases. Furthermore, if the cellular function of proteins encoded by these genes can be elucidated, observations regarding these functions can be used as a base to promote the development of therapeutic methods and pharmaceutical agents for treating allergic diseases.

SUMMARY OF THE INVENTION

The present invention was achieved in light of the above context. An objective of the present invention is to identify genes associated with allergic diseases. Furthermore, using expression of these genes as an index, another objective of the present invention is to provide methods of testing for allergic diseases, and methods of screening candidate compounds for therapeutic agents for allergic diseases, as well as pharmaceutical agents for treating allergic diseases.

The present inventors performed extensive analyses to achieve the above-mentioned objectives. Peripheral blood eosinophil count commonly serves as typical clinical indicators of atopic dermatitis. Thus, the present inventors considered that if a gene whose expression level changes with eosinophil levels could be isolated, it could lead to the isolation of a gene directly involved in atopic dermatitis.

The present inventors first attempted to identify a gene whose expression level differs with a specific allergic disease. Differential expression comparative analysis using a gene chip was carried out on genes expressed in the peripheral blood eosinophils of healthy subjects, and three groups of atopic dermatitis patients with various pathological conditions (light, severe and steroid sensitive, and severe and steroid resistant). Genes showing a greater than 3-fold variation were sorted, and the TR3 gene was selected from among approximately 12,000 A-chip genes, wherein the chip was mainly loaded with known genes. Two cases of eosinophil RNA from each group, including the healthy subjects, were applied to the gene chip, and expression comparison between two groups was carried out by comparing gene expression in four combinations of two cases from each group. Comparison of expression between healthy subjects and subjects with severe symptoms (steroid sensitive) showed that TR3 expression varied by more than three-fold (enhanced in severe symptoms) in all four combinations. To confirm those observations, RT-PCR was carried out on panels of peripheral blood eosinophils having a larger number of patients from healthy subjects and atopic dermatitis patients. These results showed that TR3 expression in atopic dermatitis patients was enhanced as compared to that in healthy subjects, thus reproducing the results obtained using the gene chip.

TR3 is known as an α-type of the nuclear orphan receptor subfamily; however, to date it has not been reported as being related to allergic disease.

TINUR is a β-type of the nuclear orphan receptor subfamily, and predicted to be functionally similar to TR3. In the same manner as for TR3, the present inventors carried out a comparison of TINUR expression between healthy subjects and patients, using ABI7700 and the same panel of patient peripheral blood eosinophils, in which there were more than ten samples per group. The results confirmed that, regardless of symptom severity, TINUR gene expression was significantly enhanced in atopic dermatitis patients as compared to healthy subjects. Like the TR3 gene, a relationship between the TINUR gene and allergic disease has not yet been reported.

Genes suggestive of apoptotic character are found in the peripheral blood eosinophils of atopic dermatitis patients. This may be because negative feedback regulation acts to reduce the increase in peripheral blood eosinophils that occurs in association with a pathologic condition.

Allergic diseases may be tested by using the expression level of the TR3 or TINUR gene of this invention as an index.

The TR3 and TINUR receptors are orphan receptors, and hitherto, neither their native ligands nor activators have been found. The present inventors developed a high-throughput system for searching for ligands, and using this system, succeeded in obtaining compounds that may function as activators of TR3 or TINUR transcription. These compounds are prostaglandins (PGA derivatives) comprising a cyclopentenone structure, and may be native ligands of the TR3 or TINUR receptor. Experiments using mutants in which a receptor's ligand-binding domain (LBD) region had been deleted indicated that the prostaglandin derivatives function by acting on this region. Moreover, experiments utilizing BIAcor demonstrated that PGA derivatives bind to TR3 and TINUR.

Thus, the present inventors found that it is possible to screen candidate compounds for a therapeutic agent for an allergic disease, and that PGA derivatives are TR3 or TINUR ligand activators.

The present inventors used a pharmacophore model to simulate the binding site of a PGA derivative TR3 ligand binding domain. The present inventors selected compounds from the database based on structure-activity relationship information for the PGA derivative reporter system. The present inventors selected compounds other than PGA derivatives that matched the binding pocket. These compounds are expected to function as TR3 receptor ligands.

Compounds that induce TR3 or TINUR gene expression, or compounds that bind to the TR3 or TINUR receptor and promote transcription activity (for example, ligand activators) are expected to have therapeutic effects on allergic diseases.

Furthermore, the present inventors discovered for the first time that the expression of TR3 and TINUR in cultured peripheral blood eosinophils is dramatically induced by apoptosis stimulation of cells via an anti-CD30 antibody comprising agonist activity towards eosinophil CD30. Therefore, a therapeutic agent for allergic diseases can be provided, wherein such an agent increases TR3 or TINUR gene expression using eosinophil CD30 ligand stimulation, and induces eosinophil apoptosis by regulating the expression of genes downstream of TR3 or TINUR occurring in eosinophils.

The present invention relates to a method of testing for allergic diseases, and a method of screening candidate compounds for therapeutic agents for allergic diseases. These methods are performed using, as an index, expression of the TR3 or TINUR gene, which are genes highly expressed in activated eosinophils during allergic disease. The present invention also relates to pharmaceutical agents for treating allergic diseases. Specifically, the present invention provides:

[1] a method of testing for an allergic disease, said method comprising the steps of:
  a) measuring the expression level of a TR3 or TINUR receptor protein, or a gene encoding the TR3 or TINUR receptor protein, in eosinophil cells of a test subject; and
  b) comparing the expression level of the protein or gene in the eosinophil cells of the test subject with an expression level in eosinophil cells of a healthy subject.

[2] the testing method of [1], wherein the gene expression level is measured by cDNA PCR.

[3] the testing method of [1] or [2], wherein the allergic disease is atopic dermatitis.

[4] a reagent for testing for an allergic disease, said reagent comprising an oligonucleotide of at least 15 nucleotides in length that comprises a nucleotide sequence complementary to a polynucleotide encoding a TR3 or TINUR receptor protein, or to its complementary strand.

[5] a method of detecting the influence of a candidate compound on the expression level of a polynucleotide of (a) or (b) below, wherein said method comprises the steps of:
  (1) contacting the candidate compound with a cell that expresses a polynucleotide of (a) or (b):
    (a) a polynucleotide encoding a TR3 or TINUR receptor protein; and
    (b) a polynucleotide encoding a protein whose expression in the eosinophils of an atopic dermatitis patient is increased, wherein said polynucleotide hybridizes under stringent conditions with a polynucleotide encoding a TR3 or TINUR receptor protein; and
  (2) measuring the expression level of the polynucleotide of (a) or (b).

[6] the method of [5], wherein the cell is from a leukocyte cell line.

[7] a method of detecting the influence of a candidate compound on the expression level of a polynucleotide of (a) or (b) below, wherein said method comprises the steps of:
  (1) administering the candidate compound to a test animal; and
  (2) measuring the expression intensity of a polynucleotide in the eosinophil cells of the test animal, wherein the polynucleotide is selected from (a) or (b):

(a) a polynucleotide encoding a TR3 or TINUR receptor protein; and (b) a polynucleotide encoding a protein whose expression in the eosinophils of an atopic dermatitis patient is increased, wherein said polynucleotide hybridizes under stringent conditions with a polynucleotide encoding a TR3 or TINUR receptor protein.

[8] a method of screening for a compound that increases the expression level of the polynucleotide (a) or (b), wherein said method comprises the steps of detecting the influence on expression level by the method of any one of [5] to [7], and selecting a compound that increases that expression level as compared to a control.

[9] a method of detecting the influence of a candidate compound on the expression level of a polynucleotide encoding a TR3 or TINUR receptor protein, wherein said method comprises the steps of:

(1) contacting a candidate compound with a cell or cell extract containing a DNA comprising a structure such that a reporter gene and the transcription regulatory region of a gene encoding a TR3 or TINUR receptor protein are operably linked; and (2) measuring the activity of the reporter gene.

[10] a method of screening for a candidate compound that increases the expression level of a gene encoding a TR3 or TINUR receptor protein, wherein said method comprises the steps of detecting the influence of a compound on the activity of the reporter gene by the method of [9], and selecting a compound that increases the activity compared to a control.

[11] a method of screening candidate compounds for a therapeutic agent for an allergic disease, wherein said method comprises the steps of:

1) contacting a test compound with a TR3 or TINUR receptor protein;

2) measuring the binding activity between the test compound and the TR3 or TINUR receptor protein; and 3) selecting the compound that binds to the TR3 or TINUR receptor protein.

[12] a method of screening candidate compounds for a therapeutic agent for an allergic disease, wherein said method comprises the steps of:

1) providing cells transfected with (a) a DNA that can express a fusion protein of a TR3 or TINUR receptor protein or its ligand binding domain and a transcription regulatory region binding protein, and (b) a DNA having a reporter gene is operably linked downstream of a DNA sequence to which the transcription regulatory region binding protein binds;

2) contacting the cell with the test compound;

3) measuring the activity of the reporter gene; and 4) selecting the compound that changes this activity.

[13] a therapeutic agent for an allergic disease, said agent comprising, as an active ingredient, a compound obtainable by the screening method of any one of [10] to [12].

[14] a therapeutic agent for an allergic disease, said agent comprising, as an active ingredient, a prostaglandin comprising a cyclopentenone structure and that is obtainable by the screening method of any one of [10] to [12].

[15] a therapeutic agent for an allergic disease, said agent comprising, as an active ingredient, a ligand of a TR3 or TINUR receptor.

[16] the therapeutic agent for an allergic disease of [15], wherein the ligand of a TR3 or TINUR receptor is a prostaglandin comprising a cyclopentenone structure.

[17] the therapeutic agent for an allergic disease of [16], wherein the prostaglandin having a cyclopentenone structure is selected from the group consisting of prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $A_1$, 15-deoxy-delta 12,14-prostaglandin $J_2$, and 8-isoprostaglandin $A_1$.

[18] the therapeutic agent for an allergic disease of [15], wherein the ligand of a TR3 receptor is any one of the compounds listed in Tables 14 to 49.

[19] the therapeutic agent for an allergic disease of any one of [13] to [18], wherein the allergic disease is atopic dermatitis.

[20] an animal model for an allergic disease, wherein the animal is a transgenic non-human vertebrate in which the expression intensity of polynucleotide (a) or (b) below is decreased in eosinophil cells:

(a) a polynucleotide encoding a TR3 or TINUR receptor protein; and (b) a polynucleotide encoding a protein whose expression in the eosinophils of an atopic dermatitis patient is increased, wherein said polynucleotide hybridizes under stringent conditions with a polynucleotide encoding a TR3 or TINUR receptor protein.

[21] the animal model of [20], wherein the transgenic animal is a knockout animal.

[22] a method of inducing cell apoptosis, said method comprising activation of a TR3 or TINUR receptor protein in the cell.

[23] the apoptosis induction method of [22], which comprises the step of contacting a cell with a compound that is obtainable by the screening method of any one of [10] to [12], or a prostaglandin comprising a cyclopentenone structure.

[24] the apoptosis induction method of [22] or [23], wherein said cell is an eosinophil cell.

[25] an apoptosis-inducing agent, which comprises a compound or a prostaglandin comprising a cyclopentenone structure and that is obtainable by the screening method of any one of [10] to [12].

[26] an apoptosis-inducing agent comprising a ligand of a TR3 or TINUR receptor as an active ingredient.

[27] the apoptosis-inducing agent of [26], wherein the ligand of the TR3 or TINUR receptor is a prostaglandin comprising a cyclopentenone structure.

[28] the apoptosis-inducing agent of [27], wherein the prostaglandin comprising a cyclopentenone structure is selected from the group consisting of prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $A_1$, 15-deoxy-delta 12,14-prostaglandin $J_2$, and 8-isoprostaglandin $A_1$.

[29] the apoptosis-inducing agent of [26], wherein the ligand of the TR3 receptor is any one of the compounds listed in Tables 14 to 49.

[30] a TR3 or TINUR gene expression-inducing agent, which comprises a ligand of an eosinophil CD30 receptor.

DETAILED DESCRIPTION OF THE INVENTION

Figure 1:
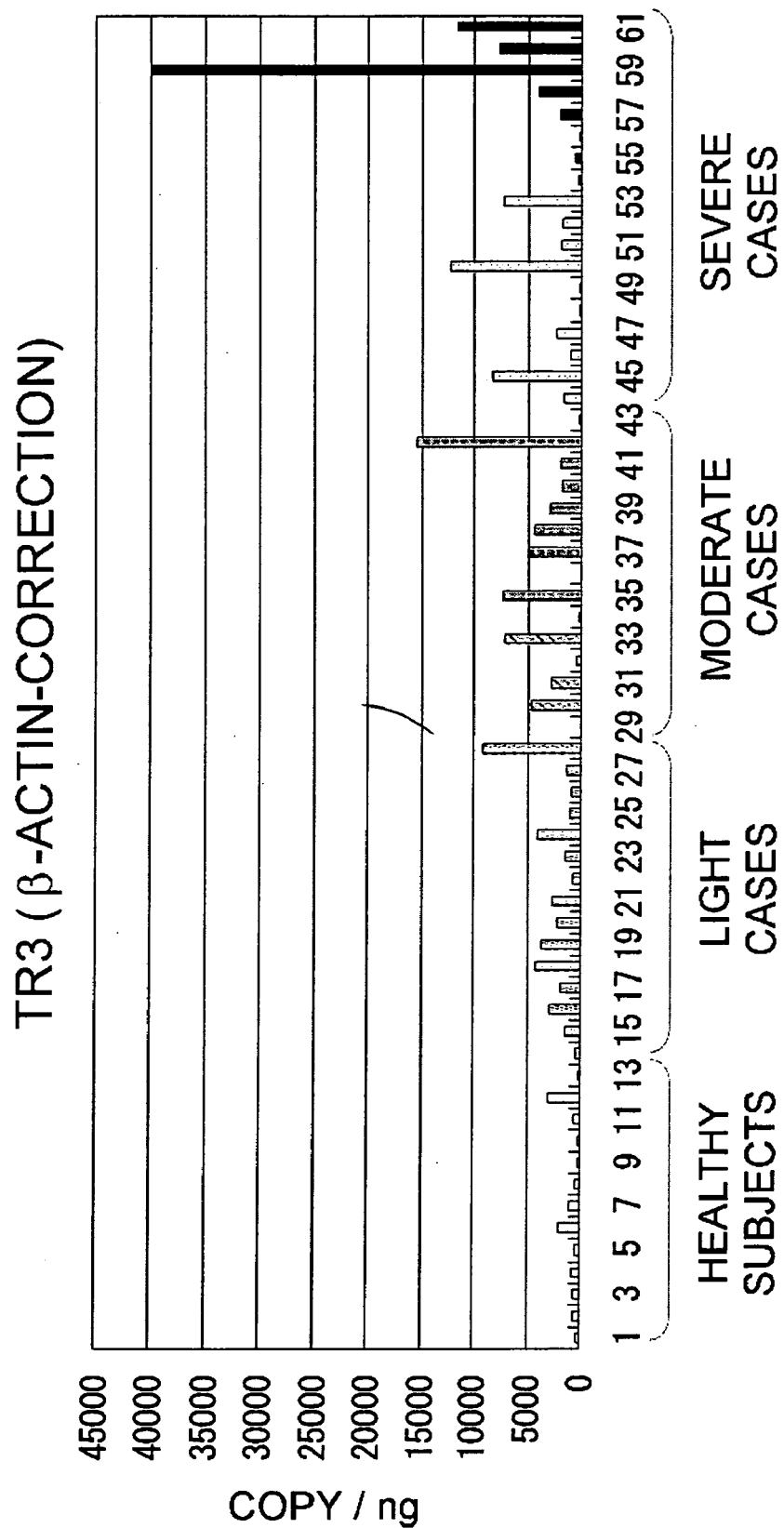
FIG. 1 shows a graph of Table 6.

The present inventors discovered that the expression level of the TR3 and/or TINUR genes increases in the eosinophils of atopic dermatitis patients. Therefore, using TR3 and/or TINUR gene expression level as an index, tests for allergic disease can be performed on test subjects.

The present invention provides methods for testing for an allergic disease, which comprise the step of measuring the expression level of the TR3 or TINUR gene.

A preferred embodiment of the present invention includes the following steps:

(a) measuring the expression level of a gene encoding the TR3 or TINUR receptor protein in the eosinophil cells of a test subject; and (b) comparing this measured value to that measured in the eosinophils of a healthy subject.

The TR3 and TINUR receptors are α and β-type orphan nuclear receptors respectively, wherein orphan nuclear receptors are composed of three subfamilies. As shown in Table 1, orphan nuclear receptors have various names, and the terms "TR3 gene" and "TINUR gene" as used in the context of the present invention should not necessarily be construed as being limited to human-derived genes.

TABLE 1

|   | Human | Mouse | Rat |
|---|---|---|---|
| α | NAK-1 (TR3) | nur77 | NGFI-B |
| β | TINUR/NOT | Nurr1 | RNR-1 |
| γ | MINOR/CHN | TEC | NOR-1 |

Information relating to the amino acid sequences of these TR3 and TINUR receptor proteins, and the nucleotide sequences of genes encoding these proteins, can be readily obtained from various gene databases available to those skilled in the art. Specifically, the nucleotide sequence of a gene encoding the human TR3 receptor protein (TR3 gene) is shown in SEQ ID NO: 1; and the amino acid sequence of the human TR3 receptor protein is shown in SEQ ID NO: 2. The nucleotide sequence of a gene encoding the human TINUR receptor protein (TINUR gene) is shown in SEQ ID NO: 3; and the amino acid sequence of the human TINUR receptor protein is shown in SEQ ID NO: 4.

Herein, the general phrase "allergic disease" refers to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation. Examples of allergens include mite antigens and pollen antigens.

Representative allergic diseases include bronchial asthma, allergic rhinitis, atopic dermatitis, and pollen and insect allergies. Allergic diathesis is a genetic factor that can be inherited by the children of allergic parents. Familial allergic diseases are also called atopic diseases, and the causative, genetically transmitted factor is atopic diathesis. "Atopic dermatitis" is a general term for an atopic disease, especially diseases accompanied by dermatitis symptoms.

The tests for allergic diseases of the present invention can include, for example, a test for determining whether a subject is affected with an allergic disease, a test for determining whether a subject comprises the trait of being easily affected by an allergic disease, and a test for assessing whether allergic symptoms are improving. The TR3 or TINUR gene of this invention showed increased expression level in the activated eosinophils of atopic dermatitis patients. Since eosinophils are a representative clinical marker for atopic dermatitis, a clinical marker associated with their decrease is useful for assessing therapeutic effects. More specifically, increased TR3 or TINUR gene expression indicates improvement of the allergic disease, accompanied by a decrease in eosinophils.

There is a correlation between atopic dermatitis severity and the number of eosinophils, such that active reduction of eosinophil number may lead to curing the disease. Measurement of these genes, whose specific induction in eosinophils is accompanied by a decrease in eosinophil numbers, along with discovery of methods or substances that actively induce these genes from outside the cell, may lead to novel methods of atopic dermatitis therapy, and diagnostic methods for evaluating these therapeutic methods.

Herein, the expression level of the TR3 or TINUR gene includes transcription of the gene to mRNA, as well as translation into their protein. Therefore, a method of testing for an allergic disease according to the present invention can be performed by comparing the expression intensity of mRNA corresponding to the particular gene, or the expression level of the protein encoded by that gene.

Measurement of TR3 or TINUR gene expression level in a method of testing for allergic diseases of the present invention may be conducted according to gene analytical methods known to those skilled in the art. More specifically, a hybridization technique using as a probe a nucleic acid that hybridizes to either the TR3 or TINUR gene, or a gene amplification technique using as a primer a DNA that hybridizes to a gene of this invention, or such can be utilized.

Primers or probes that can be used as reagents for testing for an allergic disease according to the present invention include a polynucleotide comprising at least 15 nucleotides that is complementary to the nucleotide sequence of SEQ ID NO: 1 or 3, or the complementary strand thereof. Herein, the term "complementary strand" refers to the other strand of one strand of a double stranded DNA, which is composed of A:T (or A:U for RNA) and G:C base pairs. In addition, "complementary" means not only those sequences completely complementary to a region of at least 15 continuous nucleotides, but also those having a homology of at least 70%, preferably at least 80%, more preferably 90%, and even more preferably 95% or higher. The degree of homology between nucleotide sequences can be determined using a known algorithm, such as BLASTN.

Such polynucleotides are useful as probes to detect and isolate a polynucleotide encoding a protein of the present invention, or as primers to amplify a polynucleotide of the present invention. When used as a primer, these polynucleotides have a chain length of usually 15 bp to 100 bp, and preferably 15 bp to 35 bp. When used as a probe, DNAs comprising the entire sequence of a polynucleotide of the present invention, or its partial sequence containing at least 15-bp, are used. When used as a primer, the 3' region must be complementary to a polynucleotide of the present invention, however the 5' region can be linked to a restriction enzyme-recognition sequence, tag, or the like.

A "polynucleotide" of the present invention may be either DNA or RNA. These polynucleotides may be either synthetic (isolated) or naturally occurring. In addition, DNA used as a hybridization probe is preferably labeled. Examples of labeling methods are described below. Herein, the term "oligonucleotide" refers to polynucleotides with a relatively low degree of polymerization. Oligonucleotides are included in polynucleotides. Exemplary labeling methods are as follows:

nick translation labeling using DNA polymerase I;
end labeling using polynucleotide kinase;
fill-in end labeling using the Klenow fragment (Berger, SL, Kimmel, AR. (1987) Guide to Molecular Cloning Techniques, Method in Enzymology, Academic Press; Hames, B D, Higgins, S J (1985) Genes Probes: A Practical Approach. IRL Press; Sambrook, J, Fritsch, E F, Maniatis, T. (1989) Molecular Cloning: a Laboratory Manual, 2nd Ed. Cold Spring Harbor Laboratory Press);
transcription labeling using RNA polymerase (Melton, D A, Krieg, P A, Rebagkiati, M R, Maniatis, T, Zinn, K, Green, M R. (1984) Nucleic Acid Res., 12, 7035–7056); and
non-radioisotopic labeling of DNA by incorporating modified nucleotides (Kricka, L J. (1992) Nonisotopic DNA Probing Techniques. Academic Press).

When testing for allergic diseases using hybridization techniques, for example, Northern hybridization, dot blot hybridization or DNA microarray techniques may be used. Gene amplification techniques such as RT-PCR may also be used. During the gene amplification step of RT-PCR, PCR amplification monitoring can be used to quantitatively analyze expression of the gene of the present invention.

In PCR gene amplification monitoring, the detection target (the DNA or reverse transcript of RNA) is hybridized to probes that are dual-labeled at both ends with different fluorescent dyes, whose fluorescence cancels each other out. As the PCR proceeds and the Taq polymerase degrades the probe due to its 5'-3' exonuclease activity, the two fluorescent dyes become distant from each other and fluorescence is detected. Fluorescence is detected in real time. By simultaneously measuring a standard sample in which the target copy number is known, it is possible to use cycle number to determine the target copy number of the subject sample, when PCR amplification is linear (Holland, P. M. et al., 1991, Proc. Natl. Acad. Sci. USA 88: 7276–7280; Livak, K. J. et al., 1995, PCR Methods and Applications 4(6): 357–362; Heid, C. A. et al., 1996, Genome Research 6: 986–994; Gibson, E. M. U. et al., 1996, Genome Research 6: 995–1001). For example, ABI PRISM7700 (PE BIOSYSTEMS) may be used for the PCR amplification monitoring method.

A method of testing for allergic diseases of the present invention can also be carried out by detecting a protein encoded by the TR3 or TINUR gene. Test methods that may be employed include those using an antibody that binds to a protein encoded by the TR3 or TINUR gene, such as Western blotting, immunoprecipitation and ELISA.

Antibodies that bind to the TR3 or TINUR protein used in the detection step may be produced by techniques well known to those skilled in the art. Antibodies used in the present invention may be polyclonal or monoclonal (Milstein, C. et al., 1983, Nature 305 (5934): 537–40). For example, polyclonal antibodies against a protein of the present invention may be produced by collecting blood from mammals sensitized with an antigen, and separating serum from this blood using known methods. Serum containing polyclonal antibodies may be used as polyclonal antibodies. A fraction containing polyclonal antibodies can be further isolated from this serum as required. Alternatively, monoclonal antibodies may be obtained by isolating immune cells from mammals sensitized with an antigen, fusing these cells with myeloma cells or the like, cloning the hybridomas thus obtained, and collecting the antibodies from the culture for use as monoclonal antibodies.

These antibodies may be appropriately labeled to detect the TR3 or TINUR protein. Alternatively, instead of labeling these antibodies, a substance that specifically binds to these antibodies, for example, protein A or protein G, may be labeled to indirectly detect the protein. ELISA is one example of such an indirect detection method.

A protein or its partial peptide to be used as an antigen may be obtained by: 1) inserting the TR3 or TINUR gene, or a portion of the TR3 or TINUR gene, into an expression vector, 2) introducing the vector into an appropriate host cell to produce a transformant, 3) culturing the transformant to express the recombinant protein, and 4) purifying the expressed recombinant protein from the culture or the culture supernatant. Alternatively, oligonucleotides consisting of a partial amino acid sequence of the amino acid encoded by the TR3 or TINUR gene can be chemically synthesized and used as the immunogen.

The samples of this invention are preferably eosinophils derived from test subjects. Eosinophils can be prepared from peripheral blood using conventional methods. For example, leukocytes are isolated by fractionating heparinized blood using centrifugation. Granulocytes can then be fractionated by, for example, Ficoll centrifugation of the leukocytes. Eosinophils can be then isolated by neutrophil depletion using the CD16 antibody. A sample for immunological assays of the aforementioned proteins can then be obtained by disrupting these isolated eosinophils to produce a lysate. Alternatively, a sample for measuring mRNA corresponding to the aforementioned gene can be obtained by extracting mRNA from this lysate. The use of a commercially available kit is useful in extracting mRNA or preparing eosinophil lysate.

In the present invention, the expression level of the gene serving as the index can be measured from whole blood or a peripheral blood leukocyte population, without isolating eosinophils. In this case, the change of gene expression level in cells can be determined by correcting measured values. For example, the measured expression level of an index gene of the present invention can be corrected based on the measured expression level of a housekeeping gene, that is, a gene specifically expressed in eosinophils, and whose expression level does not significantly change, regardless of cellular conditions.

Alternatively, where the protein to be detected is a secretory protein, comparison of the expression level of a gene encoding the protein can be accomplished by measuring the amount of the target protein in a sample of the subject's body fluid, such as blood or serum.

When the result of a test for allergic disease of this invention shows elevated expression of a gene of this invention, allergic symptoms are presumed to be improving together with a decrease in eosinophils. This is especially the case for patients with an allergic disease such as atopic dermatitis Furthermore, this invention also relates to an allergic disease animal model, wherein said animal is a transgenic non-human animal having decreased expression of the polynucleotide of (a) or (b) in eosinophil cells:
(a) a polynucleotide encoding the TR3 or TINUR receptor protein; and
(b) a polynucleotide encoding a protein whose expression in the eosinophils of atopic dermatitis patients is increased, wherein the polynucleotide hybridizes under stringent conditions with a polynucleotide encoding the TR3 or TINUR receptor protein.

According to this invention, a decrease in expression level includes a knockout condition in which gene function has been substantially repressed. Herein, substantial repression of gene function refers to a condition in which neither expression of the gene, nor activity of the protein encoded by that gene, can be observed. Gene expression level can be confirmed by quantitative PCR, such as that shown in the Examples. Comparison with normal conditions can be used to confirm that translation product protein activity is virtually undetectable.

Such transgenic animals include animals that are incapable of expressing the original protein activity due to, for example, the introduction of a mutation into the coding region of the gene, which artificially causes an amino acid sequence mutation, or the introduction of a stop codon. Examples of amino acid sequence mutations include substitution, deletion, insertion and addition of amino acid(s). In addition, by mutating the transcriptional regulatory region of the gene, the actual expression of the gene of this invention can be controlled.

Methods for obtaining transgenic animals comprising a particular target gene are known. For example, a transgenic animal can be obtained by a method wherein a gene and an ovum are mixed and treated with calcium phosphate; a method wherein the gene is directly introduced into the nucleus of an pronuclear-stage oocyte using a micropipette under a phase contrast microscope (microinjection method, U.S. Pat. No. 4,873,191); a method wherein embryonic stem cells (ES cells) are used; etc. Other methods have also been developed, including a method for infecting ovum with a retroviral vector in which a gene has been inserted, and a method for transducing a gene into ovum via sperm. This latter sperm vector method is a gene recombination technique whereby an exogenous gene is introduced into an ovum by fertilization with a sperm, wherein that exogenous gene has been incorporated into the sperm by adhesion, electroporation, or the like (M. Lavitranoet, et al. Cell, 57, 717, 1989).

Transgenic animals of the present invention can be produced using any vertebrate except humans. Transgenic animals comprising various gene insertions and modified gene expression levels are currently being produced using vertebrates such as mice, rats, rabbits, miniature pigs, goats, sheep or cattle.

An example of a transgenic animal of this invention includes a knockout animal in which expression of a non-human homologue of the human TR3 or TINUR gene (described in SEQ ID NO: 1 and 3 respectively) is inhibited. Observation of the knockout animal phenotype enables knowledge of the specific function of the knocked out gene. The gene comprising the nucleotide sequence of SEQ ID NO: 1 or 3 showed increased expression in the eosinophils of human atopic dermatitis patients. Therefore, an animal in which a homologue of this gene is knocked out is useful as an animal model for allergic diseases.

For example, if a knockout animal of this invention develops dermatitis, or exhibits a change in measured values relating to some sort of allergic disease, a screening system can be constructed to search for a compound that comprises the function of facilitating recovery from that change.

Methods for producing knockout animals are well known. Using the example of a mouse, a known method for the production of a knockout animal is by homologous recombination using embryonic stem cells, and then selection of embryonic stem cells in which one of the alleles is modified or destroyed. A chimeric animal containing cells derived from an embryonic stem cell together with cells derived from an embryo can be obtained, for example, by inserting a genetically manipulated embryonic stem cell into a fertilized egg. When this chimeric animal (chimera refers to a single individual formed from somatic cells derived from two or more fertilized eggs) is crossed with a normal mouse, a heterozygote in which one of the alleles is modified or destroyed in its entirety, can be produced. Furthermore, a homozygote can be produced by crossing heterozygotes. The transgenic animals of this invention include both heterozygotes and homozygotes.

Homologous recombination refers to a mechanism of genetic recombination that occurs between two genes comprising the same or very similar nucleotide sequences. PCR can be used to select cells that have undergone homologous recombination. A portion of an inserted gene, and a portion of the region in which insertion is expected, can be used as primers in a PCR reaction carried out to confirm homologous recombination in cells that produce amplification products. Furthermore, when inducing homologous recombination of a gene expressed in an embryonic stem cell, cell selection can be easily carried out using neomycin resistance, wherein a neomycin resistance gene has been linked to a transgene and introduced into a cell. This and other known methods, and modified methods thereof, can be used to select cells.

In addition to use in the screening of pharmaceutical agents for the treatment or prevention of allergic diseases, described below, transgenic animals of this invention are also useful for elucidating the mechanisms of allergic diseases, and for testing the safety of screened compounds.

The present invention revealed that expression of the TR3 and TINUR genes increases in the eosinophils of atopic dermatitis patients. This may be because negative feedback regulation acts to reduce the increase in peripheral blood eosinophils that occurs in association with a pathologic condition. Therefore, animals that can be used as allergic disease model animals include animals in which the expression level of the TR3, the TINUR gene, or a gene functionally equivalent to the TR3 or TINUR gene, has been artificially lowered in eosinophil cells. A decrease of gene expression level in eosinophils includes a decrease in the expression level over the entire leukocyte population. In other words, this phrase includes decreased expression of the aforementioned genes not only in eosinophils but also over the general leukocyte population. In the present invention, a functionally equivalent gene normally refers to a gene of either (a) or (b), described above. More specifically, examples of functionally equivalent genes of this invention include genes that hybridize under stringent conditions to a gene that encodes TR3 or TINUR. Generally, the following conditions can be indicated as the stringent conditions of this invention. For example, hybridization in 4×SSC at 65° C. followed by washing with 0.1×SSC at 65° C. for one hour. The temperature conditions for hybridization and washing greatly influence stringency and can be adjusted using melting temperature (Tm). Tm varies with the ratio of constitutive nucleotides in the hybridizing base pairs, and with the composition of the hybridization solution (concentrations of salts, formamide and sodium dodecyl sulfate). Therefore, on considering these conditions, one skilled in the art can select appropriate conditions to achieve an equal stringency based experience or experimentation.

For example, the aforementioned transgenic animals may be used as the animal model of this invention.

Furthermore, the present invention provides a method for detecting the influence of a candidate compound on the expression level of a polynucleotide of this invention. According to this invention, TR3 or TINUR gene expression level is significantly increased in the eosinophils of atopic dermatitis patients. This is thought to be due to negative feedback regulation that acts to reduce the increase in peripheral blood eosinophils that occurs in association with a pathologic condition. Therefore, based on these methods for detecting influence on gene expression level, compounds that increase gene expression level can be selected, and therapeutic drugs for allergic diseases can be obtained. Herein, compounds that increase the expression level of a gene refer to compounds that comprise the function of inducing any one of the steps selected from gene transcription, translation and expression of protein activity. The present invention further provides a method for detecting the activity of the TR3 or TINUR gene product protein (transcriptional activation ability), as well as TR3 or TINUR gene expression level. Therapeutic drugs for allergies can be devised by selecting compounds that increase the activity of the TR3 or TINUR gene product protein (transcriptional activation ability).

The method for detecting the influence of a candidate compound on the expression level of a polynucleotide of this invention can be performed in vivo or in vitro. To detect in vivo influence, an appropriate test animal should be used. Test animals that can be used include, for example, an allergic disease animal model, or an allergic disease animal model that is a transgenic non-human animal in which the expression of the aforementioned (a) or (b) gene is inhibited in eosinophils. In vivo influence on expression level based on the present invention can be detected, for example, according to the following steps:

(1) administering a candidate compound to a test animal; and
(2) measuring the expression level of the polynucleotide of the above-described (a) or (b) in the eosinophils of the test animal.

A test animal for the method of detection of this invention can also include, for example, transgenic animals in which TR3 or TINUR gene expression has been decreased through the expression of a TR3 or TINUR antisense gene. Such transgenic animals may be produced by first constructing an antisense RNA expression vector by inserting the full-length TR3 or TINUR gene, or partial sequence thereof, in the reverse direction and downstream of an appropriate promoter sequence. This expression vector is then introduced into the nucleus to express a TR3 or TINUR antisense gene. Thus, a transgenic animal with reduced TR3 or TINUR gene expression can be obtained. When the expression vector contains a promoter whose transcription is regulated by an appropriate pharmaceutical substance, TR3 or TINUR gene expression level in the transgenic animal can be controlled by administering that substance.

The influence of a pharmaceutical agent candidate compound on TR3 or TINUR gene expression can be detected by administering that compound to an animal model in which TR3 or TINUR gene expression has been reduced as described above, and then monitoring the effect of that compound on TR3 or TINUR gene expression in the eosinophils of that animal model.

The method of screening of this invention allows selection of pharmaceutical agents involved in TR3 or TINUR gene expression in various ways. For example, this invention enables the discovery of pharmaceutical agent candidate compounds having any of the following functions:

Activating a signal transduction pathway that drives TR3 or TINUR gene expression;
Increasing TR3 or TINUR gene transcription activity;
Inhibiting degradation or stabilization of the TR3 or TINUR gene transcription product; etc.

In vitro detection can be performed using a method wherein a candidate compound is contacted with cells expressing one of the above-described (a) or (b) genes, and the expression level of that gene is detected. More specifically, the method may be carried out according to the following steps:

(1) contacting a candidate compound with cells that express a polynucleotide of the above-described (a) or (b); and
(2) measuring the expression level of that polynucleotide of the above-described (a) or (b).

In this invention, cells to be used in step (1) can be obtained by inserting such a polynucleotide into an appropriate expression vector, and then transfecting suitable host cells with that vector. Vector or host cells capable of expressing a gene of this invention should be used. Examples of host cells in the host-vector system are *Escherichia coli*, yeast cells, insect cells, animal cells and the like. Vectors for use with each of these cells can be routinely selected.

Vectors may be transfected into a host by biological, physical or chemical methods. Biological methods include, for example, methods using viral vectors; methods using specific receptors; and cell-fusion methods (HVJ (hemagglutinating virus of Japan; Sendai virus) method, polyethylene glycol (PEG) method, electric cell fusion method, and microcell fusion method (chromosome transfer)). Examples of physical methods include microinjection, electroporation and the use of a gene particle gun. Chemical methods are exemplified by the calcium phosphate precipitation method, liposome method, DEAE-dextran method, protoplast method, erythrocyte ghost method, erythrocyte membrane ghost method, and microcapsule method.

In a detection method of this invention, leukocyte cell lines can be used as cells for expressing the polynucleotide of the aforementioned (a) or (b). Examples of leukocyte cell lines are cell lines derived from leukocytes, such as Eol, YY-1, HL-60, TF-1 and AML14.3D10. Among the leukocyte cell lines, cell lines derived from eosinophils are preferred for a detection method of this invention. Examples of cell lines derived from eosinophils include Eol, YY-1 and AML14.3D10.

Eol (Eol-1: Saito H et al., Establishment and characterization of a new human eosinophilic leukemia cell line. Blood 66, 1233–1240, 1985) can be obtained from the Hayashibara Research Institute. YY-1 (Ogata N et al., The activation of the JAK2/STAT5 pathway is commonly involved in signaling through the human IL-5 receptor. Int. Arch. Allergy Immunol., Suppl 1, 24–27, 1997) is available from the Institute of Cytosignal Research. AML14.3D10 (Baumann M A et al., The AML14 and AML14.3D10 cell lines: a long-overdue model for the study of eosinophils and more. Stem Cells, 16, 16–24, 1998) is commercially available from Paul CC at Research Service, VA Medical Center, Dayton, Ohio, USA.

HL-60 clone 15 (ATCC CRL-1964), an undifferentiated leukocyte cell line, will differentiate into eosinophils to produce an eosinophil cell line when cultured for about a week in the presence of butyric acid. Eosinophils are polymorphonuclear and exhibit eosinophilic granules, and can thus be detected by their morphological characteristics. Morphological observations are performed using Giemsa staining and Difquick staining. Generally, a human leukocyte cell line containing eosinophils can be established by cloning an immortalized cell sample from a leukemia patient. Therefore, one skilled in the art can use a conventional method to obtain an eosinophil cell line, as necessary. The method of screening involves the addition of a candidate compound to the aforementioned leukocyte cell line, measurement of the expression levels of the polynucleotides of (a) or (b) in the leukocyte cell line, and selection of a compound that increases the gene expression level.

Transformed cells in which the expression of the polynucleotide of the aforementioned (a) or (b) is modified can be used as cells for the in vitro detection method. Examples of such transformed cells include cells transformed with an expression vector for the polynucleotide antisense. Cells transformed with an antisense expression vector can be obtained according to a principle similar to that used in the production of the aforementioned transgenic animal. Using the transformed cell thus obtained, the influence of the candidate compound on gene expression level can be detected.

In a method of the present invention, the expression levels of the polynucleotide of the above-described (a) or (b) can be compared by detecting the expression levels of not only proteins encoded by these genes, but also of their corresponding mRNAs. When comparing expression level using mRNA, the step of preparing an mRNA sample as described above is conducted instead of preparing a protein sample. Protein and mRNA detection can be carried out according to known methods, such as those described above.

By obtaining the transcriptional regulatory region of the TR3 or TINUR gene, a reporter assay system can be constructed. A reporter assay system is a system of screening for a transcriptional regulatory factor that acts on the transcriptional regulatory region. Such a system uses the expression level of a reporter gene located downstream of the transcriptional regulatory region, and expressed under the control of that regulatory region, as an index.

A transcriptional regulatory region is exemplified by a promoter and an enhancer, as well as a CAAT box, TATA box or the like, usually found in the promoter region. Examples of suitable reporter genes include the chloramphenicol acetyltransferase (CAT) gene, luciferase gene and growth hormone genes.

A transcriptional regulatory region of the TR3 or TINUR gene can be obtained using conventional methods as follows. First, a genomic DNA clone comprising the cDNA sequence based on a nucleotide sequence described in SEQ ID NO: 1 or 3, is screened by a method using PCR or hybridization from a human genomic DNA library, such as the BAC or YAC libraries. Based on the resulting genomic DNA sequence, the transcriptional regulatory region of the TR3 or TINUR gene is predicted and obtained. A reporter construct is prepared by cloning the obtained transcriptional regulatory region upstream of a reporter gene. The resulting reporter construct is introduced into a cultured cell strain to prepare transformants for screening. By contacting a candidate compound with a transformant and detecting reporter gene expression, the effect of that candidate compound on the transcriptional regulatory region can be assessed.

Based on the methods for detecting influence on the expression level of the polynucleotides of the present invention, a compound that alters the expression level of these polynucleotides can be screened. The present invention relates to a method of screening for a compound that alters the expression level of a polynucleotide of above-described (a) or (b), comprising the steps below.

The present invention provides a method of screening for a compound that increases the expression level of a polynucleotide of above-described (a) or (b), the method comprising the steps of: 1) detecting the influence of a candidate compound on the expression level of the polynucleotide in vivo and/or in vitro, and 2) selecting the compound that increases expression level as compared to a control.

This invention also relates to a method of screening for a compound that acts on the transcriptional regulatory region, wherein that method uses a reporter assay which utilizes the transcriptional regulatory region of the TR3 or TINUR gene. A compound that increases reporter gene expression level as compared to a control can be selected based on the results of the reporter assay of the present invention, and a compound that induces TR3 or TINUR gene expression can thus be obtained. Thus, the present invention relates to a method of screening for agonists or antagonists that bind to the ligand-binding domain.

The TR3 and TINUR receptor proteins, discovered by the present inventors as proteins associated with allergic diseases, are orphan receptors and hitherto, their native ligand activators have not been found. TR3 or TINUR protein ligand activators are considered to directly activate TR3 or TINUR in eosinophils, and to promote apoptosis. Therefore, TR3 or TINUR receptor ligand activators are expected to serve as therapeutic agents for allergic disease. Generally, a receptor ligand can be obtained by searching for compounds that bind to the receptor protein.

The present invention provides a method of screening candidate compounds for therapeutic agents for allergic disease, wherein such a method comprises selecting compounds that can bind to the TR3 or TINUR protein. In this method, the TR3 or TINUR receptor protein is contacted with a test compound, binding activity between each receptor protein and the test compound is measured, and a compound that binds to a receptor protein is selected. Agonists and antagonists can be selected by measuring this binding as well as by measuring TR3 or TINUR transcription activity.

The TR3 and TINUR receptor proteins of this method include their partial peptides. One skilled in the art can use known methods to measure binding activity between the TR3 or TINUR receptor protein and a test compound of the above-described method.

For example, if the compound that binds to TR3 or TINUR is a protein, West-Western blotting can be performed as the screening method of the present invention. Specifically, a cDNA library that uses a phage vector (λgtll, ZAPII, etc.) is constructed from tissues or cells predicted to express a protein (test protein) that binds to the TR3 or TINUR protein. This library is then expressed on LB-agarose, and expressed proteins are immobilized onto a filter. The TR3 or TINUR protein is purified as a biotin labeled protein, or as a fusion protein with the GST protein, and reacted with the above-mentioned filter. Binding activity can be evaluated by using streptavidin, anti-GST antibodies, or the like to detect plaques that express the test protein.

Another embodiment of the method for screening a candidate compound for an allergic disease therapeutic agent of this invention includes the steps of:
(1) providing cells transfected with (a) a DNA that can express a fusion protein of the TR3 or TINUR receptor protein or a ligand binding domain thereof, and a transcription regulatory region binding protein, and (b) a DNA comprising a reporter gene operably linked downstream of the DNA sequence to which the transcription regulatory region binding protein binds;
(2) contacting the above-mentioned cells with a test compound;
(3) measuring the activity of the above-mentioned reporter gene; and
(4) selecting the compound that changes the above-mentioned activity.

The phrase "operably linked" in the above-mentioned method refers to a condition in which the reporter gene is bound such that it can be expressed when the TR3 or TINUR receptor protein, or the ligand binding domain of that protein, binds to a ligand of the receptor protein or to a ligand-like compound. The GAL4 protein can be preferably used as the "transcription regulatory region binding protein" in the above-mentioned method. Furthermore, the "DNA sequence to which a transcription regulatory region binding protein binds" can be, for example, a GAL4-binding DNA region. The screening method of the present invention can be performed using a high throughput method.

In a preferred embodiment of the screening method of the present invention, screening may be performed using the "two-hybrid system" (for example, "MATCHMAKER Two-Hybrid System", "Mammalian MATCHMAKER Two-Hybrid Assay Kit", "MATCHMAKER One-Hybrid System" (all of which are manufactured by CLONTECH), "HybriZAP Two-Hybrid Vector System" (STRATAGENE), and methods reported in the literature (Dalton S, and Treisman R (1992) "Characterization of SAP-1, a protein recruited by serum response factor to the c-fos serum response element." Cell 68, 597–612"). More specifically, the method of the present invention may be performed as described below, though it is not to be construed as being limited thereto, and those skilled in the art can appropriately modify the method illustrated below to achieve this invention.

In the two-hybrid system, the TR3 or TINUR protein or a partial peptide thereof is normally fused with the GAL4 DNA binding domain and expressed in yeast cells. Using cells that are predicted to express a protein that binds to the TR3 or TINUR protein or to the partial peptide thereof, a cDNA library is constructed which expresses the protein as a fusion protein fused with a VP16 or GAL4 transcriptional activating region. The library is then introduced into yeast cells, and library-derived cDNAs are isolated from detected positive clones. (A positive clone can be detected by reporter gene activation caused when a protein that binds to the TR3 or TINUR protein, or their partial peptides including their ligand binding domain, is expressed in yeast cells, and that protein binds to the TR3 or TINUR protein or the partial peptide.) Proteins encoded by the isolated cDNAs can be obtained by transfecting and expressing these cDNAs in $E.$ $coli.$ Thus, proteins that bind to the TR3 or TINUR protein or their partial peptide, and genes encoding these proteins may be prepared. Examples of reporter genes that can be used in the two-hybrid system include, but are not limited to, the HIS3 gene, Ade2 gene, LacZ gene, CAT gene, luciferase gene and Plasminogen activator inhibitor type 1 (PAI-1) gene. Screening using the two-hybrid method can also be performed using mammalian cells or the like, in addition to yeast cells.

The present inventors utilized a two-hybrid system that uses mammalian cells, and constructed a high throughput system that can screen for ligands that increase the transcriptional activation function of the TR3 or TINUR protein. This system is an improvement over conventional mammalian two-hybrid systems, and is outlined in FIG. 2 (see Examples below).

In a preferred embodiment, the screening method of this invention is performed using the aforementioned high throughput system, developed by the present inventors.

TR3 or TINUR expression is induced under conditions of leukocyte hyperactivity, as in the peripheral blood during atopic dermatitis. As a result, there is a strong possibility that cell apoptosis will be induced. Ligands that exist in vivo can exist in locations where the nuclear receptor is highly expressed. Therefore, the present inventors screened according to the above-mentioned method, using small molecule lipid-soluble mediators predicted to be produced under such conditions as ligand candidate test compounds. Accordingly, the present inventors succeeded in obtaining from among the lipid-soluble mediators the following ligand activators for TR3: prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $A_1$, 15-deoxy-delta 12,14-prostaglandin $J_2$, 8-isoprostaglandin $A_1$ and such; and for TINUR: prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$, 8-isoprostaglandin $A_1$ and such. These compounds are prostaglandins comprising a cyclopentenone structure. This shows that ligand activators that up-regulate the transcriptional activating function of TR3 or TINUR can be obtained using a method of this invention.

Screening of compounds that bind to the TR3 or TINUR protein can also be performed using affinity chromatography. For example, the TR3 or TINUR protein can be immobilized on an affinity column carrier, and a test sample predicted to express a protein that binds to the TR3 or TINUR protein is applied thereto. Test samples that can be used in this case include cell extracts and cell lysates. After applying a test sample, the column is washed and any protein that has bound to the TR3 or TINUR protein can be prepared.

A DNA encoding a prepared protein can be obtained by analyzing that protein's amino acid sequence, synthesizing oligo DNAs based on the analyzed sequence, and then screening a cDNA library using those DNAs as a probe.

In the present invention, a biosensor utilizing the phenomenon of surface plasmon resonance may also be used to detect or measure the bound compound. A biosensor utilizing surface plasmon resonance (for example, BIACORE, PHARMACIA) uses surface plasmon resonance signals to allow real-time observation of the interaction between the TR3 or TINUR protein and the test compound. Therefore, biosensors such as BIACORE can be used to evaluate binding between the TR3 or TINUR protein and a test compound.

Isolation of compounds that bind to the TR3 or TINUR protein can be routinely performed by those skilled in the art. Methods for screening molecules that bind to a protein of this invention, other than those mentioned above, include methods wherein synthetic compounds, natural product banks or random phage peptide display libraries are acted on the immobilized TR3 or TINUR protein.

A cell used to detect the influence of a candidate compound on the expression level and transcriptional activation mechanism of the TR3 or TINUR gene, and a polynucleotide or antibody for examining the expression level of this gene, can be combined as a detection kit using a method of the present invention. Candidate compound(s) for use as a positive or negative control, as well as instructions and the like, may be included in the kit. Based on the present invention, a kit for detecting the influence of a candidate compound on the expression level and transcriptional activation mechanism of the TR3 or TINUR gene, may be utilized as a kit for screening compounds that modify the expression level or transcriptional activation mechanism of the TR3 or TINUR gene.

Test candidate compounds that can be used in a screening method of this invention include, without limitation, compound preparations synthesized by chemical methods, such as steroid derivatives; compound preparations synthesized by combinatorial chemistry; mixtures containing multiple compounds, such as extracts from animal or plant tissues, or microbial cultures; purified proteins; expression products of gene libraries; and libraries of synthetic peptides. Furthermore, in a method of screening for compounds that bind to the TR3 or TINUR protein of the present invention, without limitation, it is preferable to use small molecule lipid-soluble mediators as test candidate compounds.

Compounds selected using a method of screening of the present invention are useful as therapeutic agents for allergic diseases. Expression of the TR3 or TINUR gene increases in the eosinophils of atopic dermatitis patients. These apoptosis associated genes may be induced due to negative feedback regulation which acts to reduce the increase in peripheral blood eosinophils that occurs in association with a pathologic condition. Therefore, compounds that can enhance the expression or function of these genes are expected to comprise the action of suppressing the symptoms of atopic dermatitis.

Compounds selected using a screening method of the present invention are expected to serve as allergic disease therapeutic agents that utilize a completely novel functional mechanism that involves TR3 or TINUR activation accompanied by eosinophil apoptosis induction. Therefore, the present invention provides allergic disease therapeutic agents comprising, as an active ingredient, a compound that can be obtained by a screening method of this invention.

The above-mentioned compound includes compounds in which a portion of the structure of the compound that may be isolated using a screening method of this invention is altered by addition, deletion and/or replacement. As described above, among lipid-soluble mediators, prostaglandins comprising a cyclopentenone structure were found by the present inventors to be compounds that enhance the transcriptional activation ability of TR3 or TINUR (TR3 or TINUR ligand activators). Therefore, examples of allergic disease therapeutic agents according to this invention preferably include those that comprise, as an active ingredient, a prostaglandin that comprises a cyclopentenone structure and that can be obtained using a screening method of this invention. Specific examples of prostaglandins for TR3 include prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $A_1$, 15-deoxy-delta 12,14-prostaglandin $J_2$, 8-isoprostaglandin $A_1$ and such. Prostaglandins for TINUR include prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$, 8-isoprostaglandin $A_1$ and such.

Furthermore, substances having TR3 or TINUR receptor ligand activity of the present invention appear to induce eosinophil apoptosis and may have anti-allergic effects. Therefore, the present invention provides apoptosis-inducing agents comprising a TR3 or TINUR receptor ligand as an active ingredient, as well as allergic disease therapeutic agents comprising a TR3 or TINUR receptor ligand as an active ingredient. An apoptosis-inducing agent of the present invention is preferably an eosinophil apoptosis-inducing agent.

Examples of TR3 or TINUR receptor ligands include the above-mentioned prostaglandins comprising a cyclopentenone structure, and the compounds listed in Tables 14 to 49, shown below.

From docking studies of the three-dimensional structure of TR3 and TINUR respectively, one skilled in the art can readily infer, synthesize, and develop synthetic TR3 or TINUR ligands.

Generally, the term "docking study" refers to a computer-mediated search for compounds and conformations that fit into a ligand-binding domain, wherein these compounds and conformations are taken from a 3D database comprising several hundred thousand compounds, and wherein a 3D query pharmacophore model based on the 3D structure of a receptor is used. The docking study can be performed, for example, according to procedures (1) to (4):
(1) Construct a 3D protein structure (homology model) using Modeler;
(2) Search for a binding site using C2.LigandFit;
(3) Construct a pharmacophore query for the binding site using C2. SBF; and
(4) Search a 3D database using the pharmacophore query.

Literature relating to 3D pharmacophore searches includes, for example, Pharmacophore Perception, Development, and Use in Drug Design (1 ul Biotechnology Series, 2)-US-ISBN:0963681761 (Hardcover) Guner, Osman F. (Ed.)/Publisher: Intl. Univ. Line Published 1999/12.

Pharmaceutical agents containing such a synthetic ligand as an active ingredient are also included in the allergic disease therapeutic agents of this invention. Furthermore, by using the above-described synthetic ligands as test candidate compounds in an above-mentioned method of this invention, one can evaluate whether or not the synthetic ligand is a true ligand.

Having discovered that expression of the TR3 or TINUR receptor of this invention is specifically induced in eosinophils, the present inventors went on to search for small molecule ligands of these receptors. More specifically, they used a pharmacophore model to simulate the binding site of the PGA derivative of the TR3 ligand-binding region, and based on structure-activity relationship information on the PGA derivative reporter system, they selected from the database compounds other than PGA derivatives matching the binding pocket. Thus, compounds selected as described above are included as ligands of the TR3 or TINUR receptor of this invention. These compounds are shown in Tables 14 to 49. Such compounds may be more useful than agonist antibodies against the receptor of this invention.

The present inventors further discovered that eosinophil CD30 ligand stimulation increases the expression of the TR3 or TINUR gene. Thus, the present invention provides an expression-inducing agent for the TR3 or TINUR gene, which includes a ligand of the eosinophil CD30 receptor. The expression-inducing agent is expected to serve as an allergic disease therapeutic agent that functions by inducing eosinophil apoptosis by regulating expression of genes downstream of TR3 or TINUR in eosinophils.

The therapeutic agents, apoptosis-inducing agents, and gene expression-inducing agents for an allergic disease of this invention can be formulated by mixing an active ingredient with a physiologically acceptable carrier, excipient, diluent or such. The therapeutic agent for an allergic disease of this invention can be administered orally or parenterally, with the aim of improving allergic symptoms.

Oral drugs can be selected from dosage forms such as granules, powders, tablets, capsules, solutions, emulsions, suspensions and so on. Examples of parenteral agents include injections, suppositories and ointments. Injections may include subcutaneous injections, intramuscular injections and intraperitoneal injections.

The dosage of the therapeutic agent for allergic disease according to the present invention may vary depending upon patient age, sex, bodyweight and symptoms; treatment effects; administration method; treatment duration; and the type of active ingredient contained in the pharmaceutical composition, etc. Generally, the agent can be administered to an adult in the range of 0.1 mg to 500 mg per dose, and preferably 0.5 mg to 20 mg per dose. However, since dose changes with a variety of conditions, a dosage less than that described above may be sufficient in certain cases, and a dosage exceeding this range may be required in others.

The present inventors also discovered that cell apoptosis is induced by increased expression of the TR3 or TINUR receptor protein. Therefore, apoptosis can be induced by activating the TR3 or TINUR protein in cells. Thus, the present invention provides a method of inducing apoptosis of cells that comprises activation of the TR3 or TINUR receptor protein in these cells. The above method also includes a method wherein cell apoptosis is induced by the activation of TR3 or TINUR gene expression.

In a preferred embodiment of a method of the present invention, apoptosis is induced by contacting cells with a compound, or with a prostaglandin comprising a cyclopentenone structure, where these can be obtained by a screening method of this invention. The cells in a method of this invention are preferably eosinophils. The number of peripheral blood eosinophils is known to decrease in the remission stage in atopic dermatitis patients. Therefore, an allergic disease may be treated by specifically leading eosinophils to cell death, utilizing the method of the present invention. Thus, the present method is expected to lead to the development of novel methods for treating allergic disease.

Since compounds or prostaglandins comprising a cyclopentenone structure obtainable using a screening method of this invention are considered to comprise the function of inducing apoptosis, the present invention also provides apoptosis-inducing agents that comprise these compounds.

The present invention provides a gene whose expression differs in the activated eosinophils of atopic dermatitis patients. The use of the expression of a gene of this invention as an index enables testing for allergic disease and screening for candidate compounds for therapeutic agents.

The expression level of the allergic disease-associated genes of the present invention can be conveniently determined, regardless of allergen type. Therefore, the pathology of allergic reactions can be comprehensively understood.

The method of testing for allergic diseases of the present invention is less invasive for patients because gene expression level can be analyzed using peripheral blood eosinophils as samples. Every year, high throughput and cost effective gene analysis technology methods are being developed. Therefore, it is expected that in the near future, a method of testing for allergic diseases of the present invention will become an important bedside diagnostic tool. Accordingly, a method of the present invention is very valuable from a diagnostic perspective.

A screening method of the present invention is carried out using, as an index, a genetic function closely associated with eosinophil variation, which is a representative clinical marker for atopic dermatitis. Therefore, compounds that can be found using a screening method of the present invention are expected to be useful for pathological regulation of a wide variety of allergies.

The therapeutic agents for an allergic disease provided by the present invention are also useful as pharmaceutical agents that utilize a completely novel functional mechanism involving TR3 or TINUR activation along with eosinophil apoptosis induction.

Hereinafter the present invention is specifically illustrated with reference to Examples; however, is not to be construed as being limited thereto.

EXAMPLE 1

Differential Expression Analysis in the Peripheral Blood Eosinophils of Atopic Dermatitis Patients Using Affymetrix GeneChip In order to discover novel therapy-associated genes with fluctuating expression, or genes useful in diagnosis, differential expression comparison analysis using GeneChip was carried out on genes expressed in the peripheral blood eosinophils of healthy subjects, and of atopic dermatitis patients with various pathologic conditions (light and severe steroid sensitivity, severe steroid resistance) This analysis is described below.

Table 2 shows the profiles of six atopic dermatitis patients and two healthy subjects from whom blood samples were drawn. Allergen non-specific (Total IgE), mite-specific and cedar-specific IgEs were measured using the EIA method. More specifically, test sera were allowed to react with an anti-human IgE antibody-bound cap, and allergen non-specific, mite-specific or cedar-specific IgE antibodies in the sera were bound. Next, β-D-galactosidase-labeled anti-human IgE antibody and a substrate solution (4-methylumbelliferyl-β-D-galactopyranoside) were added and reacted, producing a fluorescent substance. The reaction was quenched by adding a quenching solution, and antibody concentration was determined using the fluorescence intensity of a simultaneously measured standard IgE. L-lactate dehydrogenase (LDH) was measured using the UV method (Wroblewski-La Due method). The rate of NADH decrease caused by its reaction with pyruvic acid was calculated using decreases in absorbance. L-type Wako LDH (Wako Pure Chemicals) and a 7170-type automatic analyzer (HITACHI) were used to measure LDH values. The number of eosinophils was measured using microscopic examination and an automatic hemocyte analyzer SE-9000 (RF/DC impedance system, Sysmex), using 2 ml of EDTA-supplemented blood as the sample.

Eosinophils prepared as described above were dissolved in

Isogen (Nippon Gene; Wako Pure Chemicals) and RNA was separated from this solution according to the Isogen protocol. Chloroform was added, the mixture was stirred and centrifuged, and the aqueous layer was collected. Next, isopropanol was added, the mixture was stirred and centrifuged, and the precipitated total RNA was collected. DNase (Nippon Gene; Wako Pure Chemicals) was added to the collected total RNA, the mixture was reacted at 37° C. for 15 minutes, and RNA was collected by phenol-chloroform extraction followed by ethanol precipitation. Using these RNAs and a gene chip, analyses were carried out according to the Affymetrix protocol, as detailed below.

(2) cDNA Synthesis for DNA Chip

Single stranded cDNA was prepared from 2 μg to 5 μg of total RNA, using reverse transcription with T7-(dT)$_{24}$ (Amersham Pharmacia Biotech) as a primer, Superscript II Reverse Transcriptase (Life Technologies), and the method of the Affymetrix Expression Analysis Technical Manual. The T7-(dT)$_{24}$ primer comprises a nucleotide sequence whereby d(T)$_{24}$ has been added to a T7 promoter nucleotide sequence as shown below.

T7-(dT)$_{24}$ primer:

5'-GGCCAGTGAATTGTAATACGACTCACTATAG   (SEQ ID NO:11)
GGAGGCGG-(dT)$_{24}$-3'

TABLE 2

|  | Healthy subject | | Light AD* subject | | Severe AD subject (steroid sensitive**) | | Severe AD subject (steroid resistant**) | |
| --- | --- | --- | --- | --- | --- | --- | --- | --- |
|  | Sex | | | | | | | |
|  | Male | Female | Male | Female | Female | Male | Male | Male |
| Age | 23 | 17 | 30 | 25 | 12 | 16 | 24 | 16 |
| Total IgE (U/ml) | 45 | 25 | 5 | 380 | 2,400 | 15,000 | 14,000 | 70,000 |
| Cedar IgE | <0.34 | <0.34 | <0.34 | 6.12 | <0.34 | 94.8 | 60.6 | >100 |
| Mite IgE | <0.34 | <0.34 | <0.34 | 18.2 | >100 | >100 | >100 | >100 |
| LDH | 228 | 241 | 211 | 296 | 477 | 465 | 303 | 595 |

*the dermatitis area <=10% the entire surface area
**sensitivity compared to standard local glucocorticoid therapy.

(1) RNA Extraction from Peripheral Blood Eosinophils for Use with a DNA Chip

A 3% dextran solution was added to whole blood drawn from a patient, and the mixture was left to stand at room temperature for 30 minutes to precipitate erythrocytes. The leukocyte fraction in the upper layer was collected, layered onto Ficoll solution (Ficoll-Paque PLUS; AMERSHAM PHARMACIA Biotech), and centrifuged at 1500 rpm for 30 minutes at room temperature. The granulocyte fraction collected in the lower layer was reacted with CD16 antibody magnetic beads at 4° C. for 30 minutes. Cells were separated using Magnetic cell sorting (MACS), and cells that eluted without being trapped were used in the experiment as eosinophils.

Next, in accordance with the Expression Analysis Technical Manual, DNA ligase, DNA polymerase I, and RNase H were added to synthesize double-stranded cDNA. The cDNA was extracted by phenol-chloroform extraction, passed through Phase Lock Gels, and then purified using ethanol precipitation.

Biotin-labeled cRNA was synthesized using a BioArray High Yield RNA Transcription Labeling Kit. The cRNA was then purified using an RNeasy Spin column (QIAGEN), and fragmented by heat treatment.

One to 5 μof this cRNA was added to a hybridization cocktail, in accordance with the Expression Analysis Technical Manual. This was placed into an array and hybridized for 16 hours at 45° C. The DNA chip used was a GeneChip$^R$ HG-U95A (AFFYMETRIX). GeneChip$^R$ HG-U95A consists of probes comprising approximately 12,000 kinds of nucleotide sequence, derived from human cDNAs and ESTs.

The DNA chip was washed, and then streptavidin phycoerythrin was added for staining. After washing, a mixed antibody solution of normal goat IgG and biotinylated goat anti-streptavidin IgG antibody was added to the array. To enhance fluorescence intensity, streptavidin phycoerythrin was again added for staining. After washing, the chip was set into a scanner and analyzed using DNA chip analysis software.

(3) DNA Chip Analysis

Expression fluorescence sensitivity was measured and data analysis was performed using the DNA chip analysis software 'Suite'. First, absolute analysis was performed on all chips, and gene expression level in each of the samples used was measured.

In the analysis of a chip's data, positives and negatives were determined by fluorescence intensity comparison with a probe set of perfect-match and m is match probes. Using Positive Fraction, Log Avg, and Pos/Neg values, results were evaluated into the three categories of Absolute Call: P (present), A (absent), and M (marginal). Definitions of these terms are shown below:

Positive Fraction: the ratio of positive pairs to probe pairs.
Log Avg: the average of the log of the fluorescence intensity ratio between perfect match and mismatch probe cells.
Pos/Neg: the ratio between the number of positive and negative probe pairs.

Average difference (Avg Diff), which is the average value of the difference in fluorescence intensities between perfect-match and mismatch probe cells, was also calculated.

Genes whose expression varied by more than threefold between patients and healthy subjects were screened, and TR3 was selected from approximately 12,000 HG-U95A chip genes. Since two eosinophil RNA samples from each group, including the healthy groups, were placed onto a gene chip, four combinations of expression comparison, 2×2 between each case, could be carried out. Expression comparison results indicated that TR3 showed a greater than three-fold variation (enhanced in severe cases) in all four combinations between healthy and severe (steroid sensitive) cases (Table 3).

Primer 2 (3'): ACTTTCGGATGACCTCCAGAGA (SEQ ID NO: 6)

TaqMan probe: ATGTACAGCAGTTCTACGACCT-GCTCTCCG (SEQ ID NO: 7)

cDNA prepared from the total RNA by reverse transcription using poly-T (12 to 18 mer) as primers was used as the template. In order to make a standard curve for the calculation of copy number, a plasmid clone containing the nucleotide sequence amplified using both primers was prepared, and serial dilutions thereof were utilized as the template for reaction. The reaction mixture composition for monitoring PCR amplification is shown in Table 4.

TABLE 4

| Reaction mixture composition for ABI-PRISM 7700 (amount per well) | |
|---|---|
| Sterile distilled water | 25.66 (µl) |
| 10× TaqMan buffer A | 5 |
| 25 mM MgCl$_2$ | 7 |
| dATP (10 mM) | 1.2 |
| dCTP (10 mM) | 1.2 |
| dGTP (10 mM) | 1.2 |
| dUTP (10 mM) | 1.2 |
| Forward Primer (100 µM) | 0.15 |
| Reverse Primer (100 µM) | 0.15 |
| TaqMan Probe (6.7 µM) | 1.49 |
| AmpliTaq Gold (5 U/µl) | 0.25 |
| AmpErase UNG (1 U/µl) | 0.5 |
| Template solution | 5 |
| Total volume | 50 |

In order to correct differences in cDNA concentrations among the samples, the same quantitative analysis was carried out for the β-actin gene that was used as the internal standard. The copy number of the target gene was calculated by performing corrections based on the copy number of this β-actin gene. For β-actin gene quantification, human cDNA was used as the template.

The primers and probe accompanying the TaqMan β-actin Control Reagents (PE Biosystems) were used for the measurement of β-actin. Their nucleotide sequences are as follows:

TABLE 3

| Experiment Name | Probe Set | Accession No. | Annotation | Avg Diff | Abs Call | Diff Call | Avg Diff Change | B = A | Fold Change | |
|---|---|---|---|---|---|---|---|---|---|---|
| C4E307-315 | 280_g_at | L13740 | TR3 orphan receptor | 1316 | P | I | 1208 | * | ~3.7 | 4(4I) |
| C4E307-340 | 280_g_at | | | 1234 | P | I | 1259 | * | ~3.9 | |
| C4E309-315 | 280_g_at | | | 2042 | P | I | 1758 | * | ~4.9 | |
| C4E309-340 | 280_g_at | | | 1913 | P | I | 1956 | * | ~5.5 | |

Primers and TaqMan probes used in ABI7700 were designed by Primer Express (PE BIOSYSTEMS) from sequence information at the National Center for Biotechnology Information (NCBI), and based on accession numbers obtained using Suite. The 5'-end of the TaqMan probe was labeled with FAM (6-carboxy-fluorescein) and the 3'-end was labeled with TAMRA (6-carboxy-N,N,N',N'-tetramethylrhodamine). The primers and probe used in the TaqMan method are shown below.

Primer 1 (5'): CCACTTTGGGAAGGAAGATGCT (SEQ iD NO: 5)

β-Actin forward primer:

TCA CCC ACA CTG TGC CCA TCT ACG A    (SEQ ID NO:12)

β-Actin reverse primer:

CAG CGG AAC CGC TCA TTG CCA ATG G    (SEQ ID NO:13)

β-actin TaqMan probe:

5'-(FAM)ATGCCC-T(TAMRA)-    (SEQ ID NO:14)
CCCCATGCCATCCTGCGTp-3'

FAM: 6-carboxy-fluorescein:
TAMRA: 6-carboxy-N,N,N',N'-tetramethylrhodamine

GeneChip expression analysis is principally aimed at genetic screening, however as each group had only two samples, the reliability of this screening was confirmed by carrying out an expression comparison between healthy subjects and patients by ABI7700 in a large patient peripheral blood eosinophil panel, in which the number of samples per group was more than ten (Table 5).

TR3 expression in peripheral blood eosinophils was confirmed to be significantly enhanced in multiple comparisons of atopic dermatitis patients compared to healthy subjects, and this was largely independent of case severity (Table 6, FIG. 1).

TABLE 5

| | No. | Sample ID | Donor ID | Transfer ID | Sex | Age | Toal IgE | Anti-mite IgE | Anti-cedar IgE | LDH | Eosinophil (%) | Eosinophil (mm$^3$) |
|---|---|---|---|---|---|---|---|---|---|---|---|---|
| 13 healthy subjects | 1 | BL10138 | V-00026 | 10138 | F | 26 | 5 | <0.34 | <0.34 | 105 | 0 | 80 |
| | 2 | BL10140 | V-00015 | 10140 | M | 52 | 81 | 0.71 | <0.34 | 78 | 2 | 150 |
| | 3 | BL10141 | V-00040 | 10141 | F | 32 | 59 | 0.37 | <0.34 | 326 | 0 | 40 |
| | 4 | BL10142 | V-00032 | 10142 | F | 35 | 83 | 14.6 | 11.2 | 187 | 3 | 250 |
| | 5 | BL10143 | V-00029 | 10143 | F | 45 | 29 | <0.34 | 1.75 | 113 | 2 | 90 |
| | 6 | BL10144 | V-00027 | 10144 | F | 29 | 17 | <0.34 | 1.51 | 74 | 2 | 90 |
| | 7 | BL10145 | V-00034 | 10145 | F | 26 | 120 | <0.34 | 17.1 | 272 | 3 | 590 |
| | 8 | BL10146 | V-00030 | 10146 | F | 30 | 560 | <0.34 | 63.2 | 251 | 1 | 120 |
| | 9 | BL10147 | V-00001 | 10147 | M | 50 | 44 | <0.34 | 17.9 | 265 | 4 | 130 |
| | 10 | BL10148 | V-00003 | 10148 | M | 43 | 220 | 4 | 3.54 | 242 | 5 | 250 |
| | 11 | BL10149 | V-00028 | 10149 | M | 32 | 110 | 1 | 9.84 | 245 | 3 | 180 |
| | 12 | BL10150 | V-00035 | 10150 | M | 63 | 86 | <0.34 | 12.6 | 209 | 5 | 300 |
| | 13 | BL10151 | V-00019 | 10151 | M | 48 | 42 | <0.34 | 14 | 300 | 1 | 180 |
| 15 light cases | 14 | BL00058 | PA00079 | 9707311 | M | 0 | 581 | | | | 9.7 | 1390 |
| | 15 | BL00068 | PA00084 | 9708072 | F | 13 | 1687 | | | | 6.8 | 365 |
| | 16 | BL00112 | PA00112 | 9712051 | M | 2 | 519 | | | | 2.2 | 151 |
| | 17 | BL00123 | PA00120 | 9712252 | F | 10 | 799 | | | | 12.9 | 1050 |
| | 18 | BL00133 | PA00129 | 9712266 | M | 12 | 274 | | | | 1.6 | 122 |
| | 19 | BL00198 | PA00023 | 9807213 | M | 21 | 9630 | | | | 15.1 | 1080 |
| | 20 | BL00207 | PA00181 | 9807273 | F | 6 | 668 | | | | 8 | 635 |
| | 21 | BL00217 | PA00190 | 9808033 | M | 5 | 777 | | | | 22.3 | 1790 |
| | 22 | BL00221 | PA00042 | 9808061 | F | 8 | 1494 | | | | 6.6 | 378 |
| | 23 | BL00234 | PA00029 | 9808311 | F | 5 | 702 | | | | 6.6 | 510 |
| | 24 | BL00252 | PA00176 | 9901071 | M | 14 | 2096 | | | | 7.2 | 333 |
| | 25 | BL00259 | PA00162 | 9902161 | M | 20 | 2622 | | | | 13.3 | 846 |
| | 26 | BL00270 | PA00213 | 9903292 | M | 15 | 230 | | | | 7.5 | 368 |
| | 27 | BL00317 | PA00240 | 0003282 | F | 14 | 106 | 3.77 | 24.7 | | 2.8 | 154 |
| | 28 | BL00327 | PA00136 | 0004033 | M | 8 | 1178 | <0.35 | <0.35 | | 4.4 | 396 |
| 15 moderate cases | 29 | BL00095 | PA00099 | 9710031 | M | 3 | 159 | | | | 2.5 | 190 |
| | 30 | BL00128 | PA00124 | 9712261 | M | 12 | 7158 | | | | 5.2 | 361 |
| | 31 | BL00145 | PA00048 | 9802192 | F | 9 | 2349 | | | | 5.1 | 193 |
| | 32 | BL00268 | PA00179 | 9903261 | M | 9 | 512 | | | | 9.5 | 906 |
| | 33 | BL00278 | PA00217 | 9904061 | M | 15 | 1082 | | | | 22.1 | 1110 |
| | 34 | BL00328 | PA00175 | 0004041 | M | 7 | 4775 | >100 | 93.3 | | 7.1 | 638 |
| | 35 | BL00089 | PA00098 | 9709092 | M | 7 | 359 | | | | 13.3 | 638 |
| | 36 | BL00110 | PA00110 | 9711281 | F | 3 | 11.5 | | | | 6.1 | 198 |
| | 37 | BL00122 | PA00119 | 9712251 | F | 12 | 528 | | | | 9.7 | 643 |
| | 38 | BL00139 | PA00025 | 9801082 | M | 18 | 22614 | | | | 13.7 | 1140 |
| | 39 | BL00156 | PA00143 | 9803264 | M | 6 | 2625 | | | | 5 | 551 |
| | 40 | BL00287 | PA00221 | 9906231 | M | 15 | 1149 | | | | 3.7 | 601 |
| | 41 | BL00296 | PA00059 | 9908201 | M | 5 | 1639 | | | | 6.8 | 477 |
| | 42 | BL00323 | PA00244 | 0003302 | M | 6 | 4532 | >100 | 69.1 | | 11 | 909 |
| | 43 | BL00335 | PA00259 | BL 18526369 | F | 14 | 1581 | >100 | 5.46 | | 15.9 | 1820 |
| 18 severe cases | 44 | BL00078 | PA00090 | 9708251 | F | 3 | 135 | | | | 3.8 | 254 |
| | 45 | BL00084 | PA00067 | 9709021 | M | 3 | 2149 | | | | 9.8 | 1000 |
| | 46 | BL00163 | PA00148 | 9803304 | M | 11 | 137 | | | | 3.5 | 274 |
| | 47 | BL00168 | PA00152 | 9804033 | F | 19 | 2732 | | | | 5.2 | 261 |
| | 48 | BL00180 | PA00163 | 9805151 | M | 17 | 14758 | | | | 13.6 | 1010 |
| | 49 | BL00242 | PA00001 | 9810061 | M | 19 | 13747 | | | | 13 | 1230 |
| | 50 | BL00243 | PA00200 | 9810221 | F | 6 | 10967 | | | | 5.9 | 662 |
| | 51 | BL00247 | PA00071 | 9812211 | M | 16 | 11610 | | | | 13.4 | 972 |
| | 52 | BL00260 | PA00209 | 9902162 | M | 0 | 136 | | | | 2.5 | 277 |
| | 53 | BL00262 | PA00120 | 9902181 | F | 10 | 120 | | | | 3 | 109 |
| | 54 | BL00150 | PA00137 | 9803161 | F | 8 | 371 | | | | 4.9 | 375 |
| | 55 | BL00257 | PA00208 | 9902053 | M | 11 | 268 | | | | 7.6 | 468 |
| | 56 | BL00293 | PA00227 | 9907221 | F | 10 | 18301 | | | | 13.8 | 1750 |
| | 57 | BL00298 | PA00229 | 9909141 | M | 11 | 9591 | >100 | 18.2 | | 11.9 | 940 |
| | 58 | BL00314 | PA00238 | 0002151 | M | 19 | 23726 | >100 | 30 | | 6 | 376 |
| | 59 | BL00318 | PA00241 | 0003283 | F | 7 | 131 | <0.35 | <0.35 | | 5.7 | 330 |
| | 60 | BL00321 | PA00243 | 0003286 | F | 4 | 232 | <0.35 | <0.35 | | 9.1 | 856 |
| | 61 | BL00337 | PA00261 | 0005191 | F | 29 | 474 | 52.5 | 31.6 | | 12.3 | 797 |

TABLE 6

| C1E-2 L13740 | Blood | β-actin (raw) copy/ng | L13740(raw) copy/ 5 ng | L13740(raw) copy/ 1 ng | β-correction raw/(ng)/average | L13740 correction raw/beta correction |
|---|---|---|---|---|---|---|
| 13 healthy subjects | 1 | 253126 | 1119 | 224 | 1.01130301 | 221 |
| | 2 | 541166 | 5637 | 1127 | 2.16209434 | 521 |
| | 3 | 214239 | 2454 | 491 | 0.855938946 | 573 |
| | 4 | 369621 | 5176 | 1035 | 1.476729393 | 701 |
| | 5 | 716536 | 6324 | 1265 | 2.862741935 | 442 |
| | 6 | 169173 | 6969 | 1394 | 0.675887508 | 2062 |
| | 7 | 601310 | 11426 | 2285 | 2.40238633 | 951 |
| | 8 | 213062 | 2097 | 419 | 0.851236036 | 493 |
| | 9 | 371589 | 1266 | 253 | 1.484591854 | 171 |
| | 10 | 646297 | 1955 | 391 | 2.582119848 | 151 |
| | 11 | 208737 | 2183 | 437 | 0.833956352 | 524 |
| | 12 | 212114 | 13130 | 2626 | 0.84744903 | 3099 |
| | 13 | 379539 | 1205 | 241 | 1.516355526 | 159 |
| 15 light cases | 14 | 508758 | 4893 | 979 | 2.032618527 | 481 |
| | 15 | 248937 | 6962 | 1392 | 0.994564691 | 1400 |
| | 16 | 221813 | 12928 | 2586 | 0.886198604 | 2918 |
| | 17 | 315168 | 11862 | 2372 | 1.259174796 | 1884 |
| | 18 | 141827 | 11906 | 2381 | 0.566636769 | 4202 |
| | 19 | 244028 | 17542 | 3508 | 0.974953584 | 3598 |
| | 20 | 348051 | 14940 | 2988 | 1.390552351 | 2149 |
| | 21 | 387693 | 20063 | 4013 | 1.548931234 | 2591 |
| | 22 | 268468 | 4232 | 846 | 1.072599907 | 789 |
| | 23 | 206673 | 5843 | 1169 | 0.825709955 | 1415 |
| | 24 | 136652 | 10968 | 2194 | 0.545959033 | 4018 |
| | 25 | 218963 | 4619 | 924 | 0.874812329 | 1056 |
| | 26 | 209273 | 3879 | 776 | 0.836097009 | 928 |
| | 27 | 131977 | 3296 | 659 | 0.52728236 | 1250 |
| | 28 | 121064 | 22191 | 4438 | 0.483680797 | 9176 |
| 6 moderate cases in the remission stage | 29 | 165901 | | 0 | 0.662815331 | 0 |
| | 30 | 134119 | 12595 | 2519 | 0.535841346 | 4701 |
| | 31 | 86340 | 4693 | 939 | 0.344949082 | 2721 |
| | 32 | 472440 | 3797 | 759 | 1.887519071 | 402 |
| | 33 | 170914 | 24513 | 4903 | 0.682845244 | 7180 |
| | 34 | 367818 | 1497 | 299 | 1.469525949 | 204 |
| 9 moderate cases in the exacerbation stage | 35 | 162258 | 23698 | 4740 | 0.648261218 | 7311 |
| | 36 | 90969 | | 0 | 0.363443211 | 0 |
| | 37 | 246460 | 24652 | 4930 | 0.984671042 | 5007 |
| | 38 | 146805 | 12808 | 2562 | 0.586522301 | 4367 |
| | 39 | 179179 | 10603 | 2121 | 0.715863818 | 2962 |
| | 40 | 138858 | 4884 | 977 | 0.554771366 | 1761 |
| | 41 | 133317 | 5210 | 1042 | 0.532635051 | 1956 |
| | 42 | 171308 | 52561 | 10512 | 0.684419966 | 15359 |
| | 43 | 285295 | 904 | 181 | 1.139827753 | 159 |
| 10 severe cases in the remission stage | 44 | 154902 | 4994 | 999 | 0.618872876 | 1614 |
| | 45 | 78948 | 12992 | 2598 | 0.315418709 | 8238 |
| | 46 | 231612 | 4595 | 919 | 0.925346905 | 993 |
| | 47 | 155564 | 7337 | 1467 | 0.621516584 | 2361 |
| | 48 | 385848 | 1428 | 286 | 1.541561787 | 185 |
| | 49 | 264744 | 437 | 87 | 1.05772078 | 83 |
| | 50 | 144715 | 35283 | 7057 | 0.578174465 | 12205 |
| | 51 | 205943 | 7545 | 1509 | 0.822795017 | 1834 |
| | 52 | 155395 | 5335 | 1067 | 0.62084169 | 1719 |
| | 53 | 151703 | 21933 | 4387 | 0.606092505 | 7238 |
| 8 severe cases in the exacerbation stage | 54 | 397821 | 2000 | 400 | 1.589395971 | 252 |
| | 55 | 446400 | 5057 | 1011 | 1.783480045 | 567 |
| | 56 | 280724 | 895 | 179 | 1.121564845 | 160 |
| | 57 | 161385 | 6500 | 1300 | 0.644775207 | 2016 |
| | 58 | 134978 | 11103 | 2221 | 0.539271624 | 4118 |
| | 59 | 24740 | 19712 | 3942 | 0.0988414 | 39885 |
| | 60 | 241793 | 37484 | 7497 | 0.966023991 | 7760 |
| | 61 | 93068 | 21520 | 4304 | 0.371831799 | 11575 |
| | total | 15268113 | | | | |

(4) Statistical Analysis

Using the above-mentioned data, parametric and non-parametric multiple comparison tests were carried out. Statistical analyses were carried out using an SAS SYSTEM, Version 4.0 Preclinical Package (SAS Institute Inc.). The results are shown in Table 7. Values were significantly greater in the patient group for all of the multiple comparisons between healthy subjects and light cases, healthy subjects and moderate cases, and healthy subjects and severe cases.

TABLE 7

| | C4E HG-U95A statistical analysis results (β-actin-corrected) | | | | | | | |
|---|---|---|---|---|---|---|---|---|
| | Parametric multiple comparison | | | | Non-parametric multiple comparison | | | |
| Name of gene | Dunnett | p-value | Tukey | p-value | Dunnett | p-value | Tukey | p-value |
| L13740 TR3 orphan receptor | AS > Nm | 0.0533 | | | AL > Nm<br>AM > Nm<br>AS > Nm | 0.0339<br>0.01<br>0.0204 | AM > Nm<br>AS > Nm | 0.0189<br>0.0378 |

(Nm = normal subject,
AL = Light case of atopic dermatitis,
AM = Moderate case of atopic dermatitis,
AS = Severe case of atopic dermatitis)

Genes indicative of apoptotic character may be enhanced in the peripheral blood eosinophils of patients with atopic dermatitis conditions due to negative feedback regulation, which acts to reduce the increase in peripheral blood eosinophils that occurs in association with a pathologic condition.

EXAMPLE 2

TR3 Receptor Ligand Search

Enhanced TR3 function can be used to promote a pathway that specifically leads eosinophils to cell death. It is highly possible that this will lead to therapies for not only asthma, but also for a variety of allergic diseases including atopic dermatitis, which was investigated by the present inventors. Structurally, TR3 is a nuclear receptor; however, it is an orphan receptor and its native ligand and activator are still unknown. If these can be discovered, TR3 can be directly activated in eosinophil cells to promote apoptosis. Therefore, it was thought that the ligand activators were highly likely to be anti-allergic agents, and a high-throughput system for ligand screening was constructed.

Figure 2:
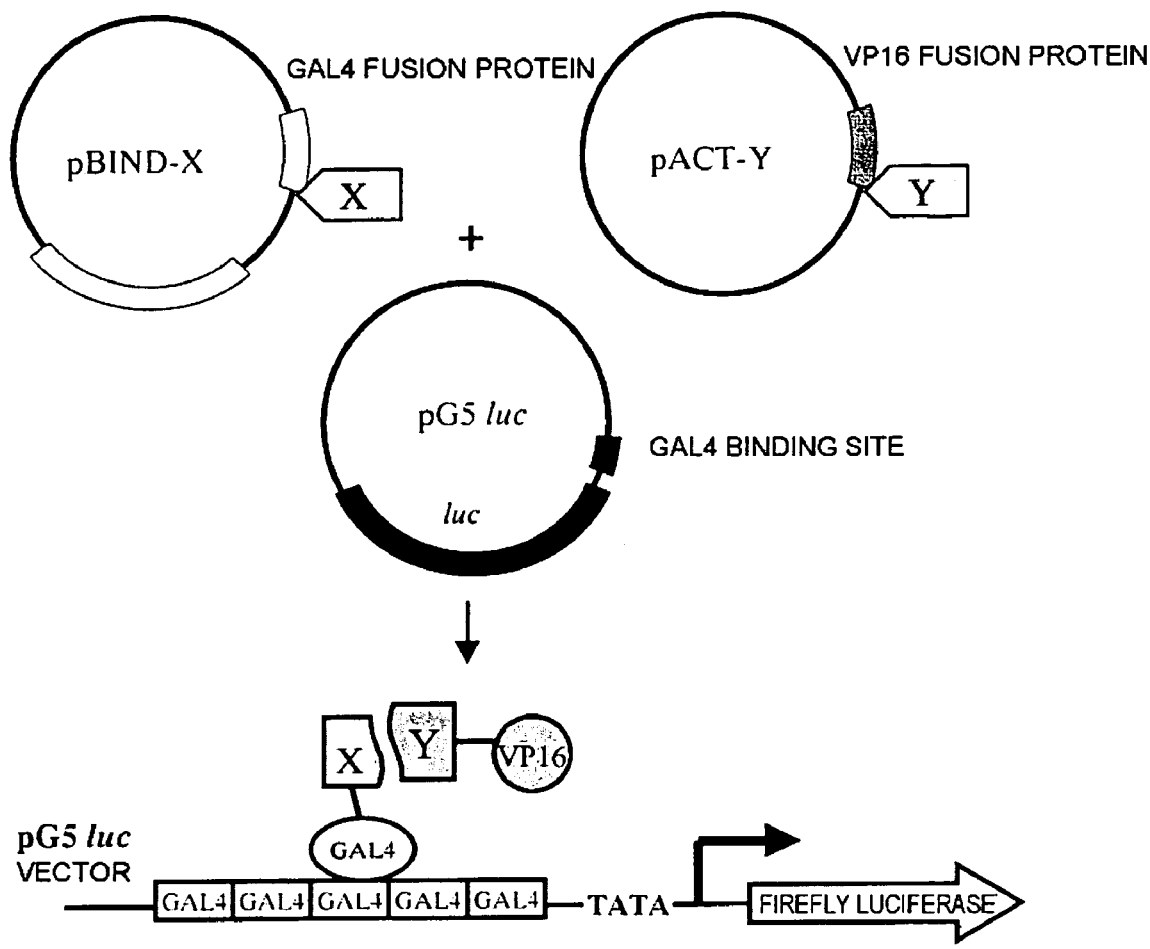
FIG. 2 shows a schematic illustration of a ligand searching system for a TR3 or TINUR receptor constructed by the present inventors. A TR3 or TINUR ligand-binding site is inserted into X, and the full-length retinoic acid X receptor (RXR) α gene is inserted into Y. These constructs are transfected into NIH3T3 cells, and the activity of induced luciferase is measured.
Figure 3:
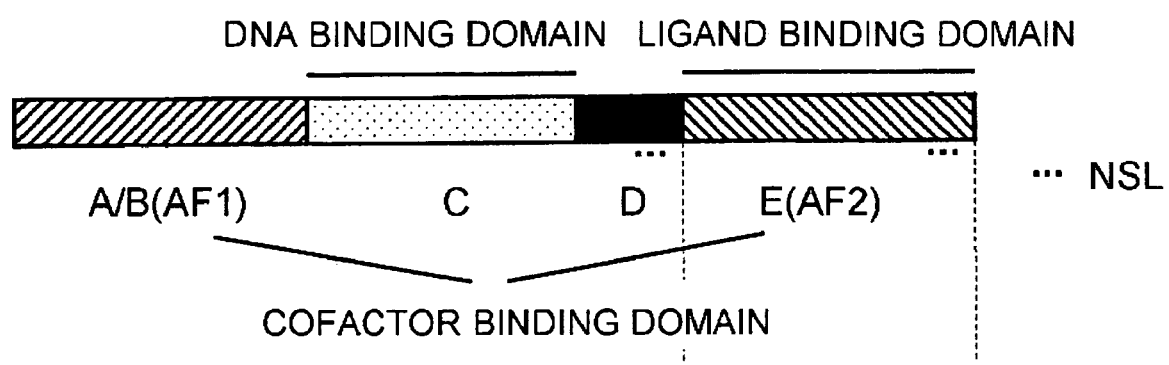
FIG. 3 shows a schematic illustration of the structure of the TR3 and TINUR receptor proteins.

As shown in FIG. 2, a mammalian two hybrid system was slightly modified by inserting the ligand binding domain sequence or full-length TR3 gene (FIG. 3) into pBIND. This was done to facilitate expression of a protein in which the DNA binding domains of TR3 and GAL4 were fused in frame. A plasmid comprising the TR3 ligand binding domain sequence inserted into pBIND, and a luciferase reporter plasmid comprising a GAL4 binding site, were co-transfected into NIH3T3 cells. Luciferase activity was measured automatically. At this time, activity was also measured by adding a retinoic acid X receptor (RXR) α-gene, which is a transcription factor that forms a heterodimer with TR3. By further adding low molecular weight substances to this system, transcriptional enhancement activity can also be used for screening.

Figure 4:
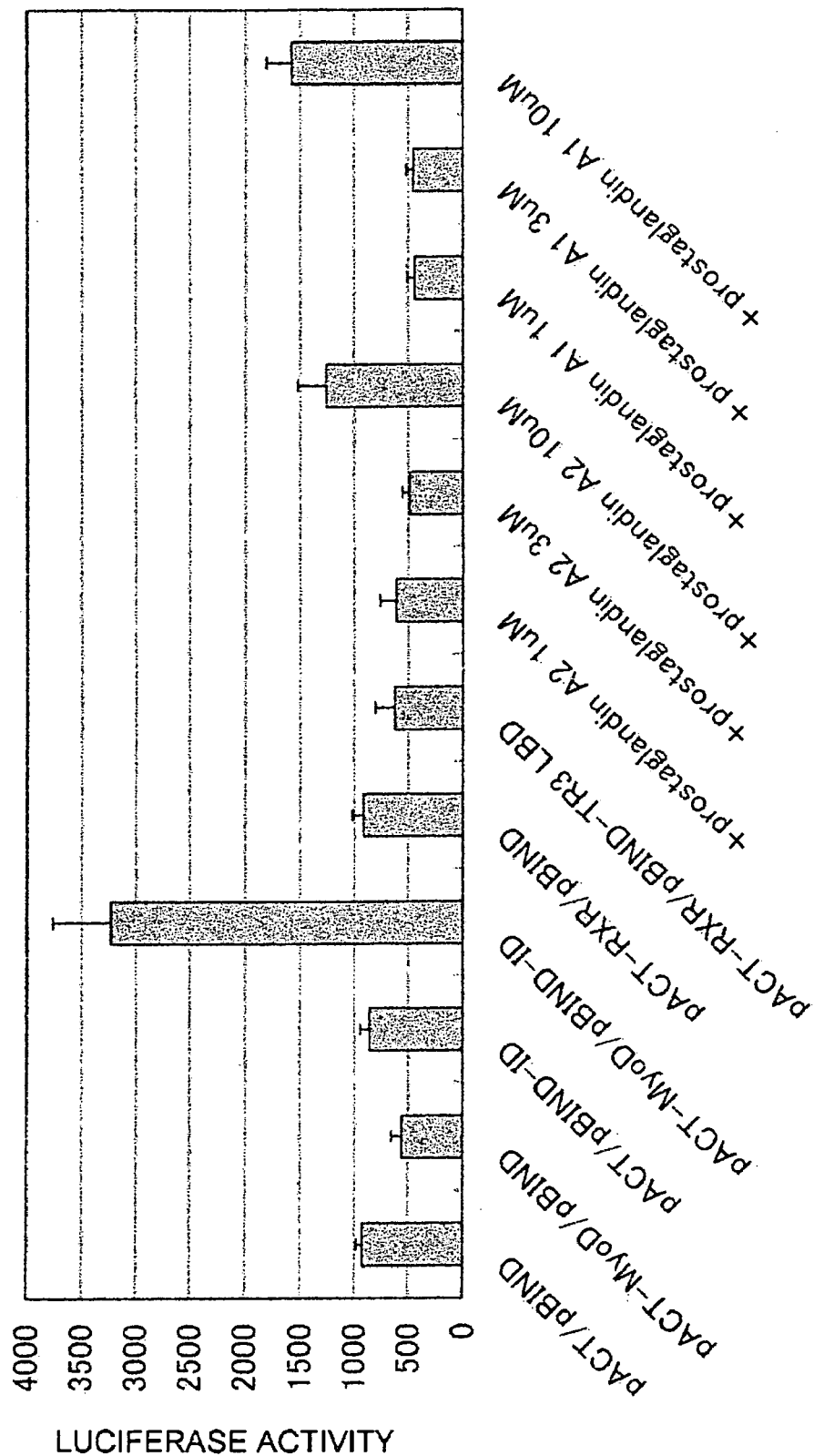
FIG. 4 shows a graph demonstrating the transcription-activating function of TR3 in a series of cyclopentenone prostaglandins using the system of FIG. 2.

TR3 expression is enhanced in activated eosinophils, such as in the peripheral blood of atopic dermatitis patients. Ligands existing in vivo may exist in sites where nuclear receptors are highly expressed. Therefore, small molecule lipid-soluble mediators considered to be produced under such conditions were added to the assay system, and evaluated based on their ability to enhance luciferase activity. Of these lipid-soluble mediators, the activity of enhancing the transcription-activating ability of TR3 was found in prostaglandins comprising a cyclopentenone structure, such as prostaglandin $A_2$, prostaglandin $A_1$, 15-epi prostaglandin $A_1$, 13,14-dihydro-15-keto prostaglandin $A_2$, 15(R)-15-methyl prostaglandin $A_2$, and delta12-prostaglandin J2 (FIG. 4, Tables 8 to 12). In this manner, the method established by the present inventors paved the way for the high throughput discovery of native and synthetic TR3 ligands. At the same time the present inventors also found that compounds such as prostaglandin $A_2$, prostaglandin $A_1$, and similar metabolites have a high probability of being authentic TR3 native ligands.

TABLE 8

| | | Nur77 LBD-ligand activity | | Full length Nur77-ligand activity | | Nurr1 LBD-ligand activity | | Full length Nurr1-ligand activity | |
|---|---|---|---|---|---|---|---|---|---|
| Name of compound | Structural formula | RXR(+) | RXR(−) | RXR(+) | RXR(−) | RXR(+) | RXR(−) | RXR(+) | RXR(−) |
| Prostaglandin $A_2$ | 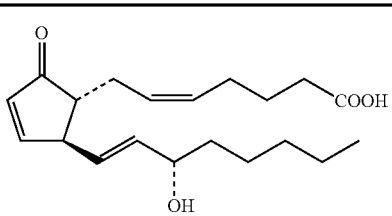 | ◯ 10 μM | X | ◯ 10 μM | ◯ 10 μM | ◯ 10 μM | X | ◯ 10 μM | ◯ 10 μM |

TABLE 8-continued

| Name of compound | Structural formula | Nur77 LBD-ligand activity | | Full length Nur77-ligand activity | | Nurr1 LBD-ligand activity | | Full length Nurr1-ligand activity | |
|---|---|---|---|---|---|---|---|---|---|
| | | RXR(+) | RXR(−) | RXR(+) | RXR(−) | RXR(+) | RXR(−) | RXR(+) | RXR(−) |
| Prostaglandin $A_1$ | | ◯ 10 μM | X | ◯ 10 μM | ◯ 10 μM | ◯ 10 μM | X | ◯ 10 μM | ◯ 10 μM |
| 16,16-dimethyl Prostaglandin $A_2$ | | X | X | X | X | X | X | X | X |

TABLE 9

| Prostaglandin $A_3$ | | X | X | X | X | X | X | X | X |
|---|---|---|---|---|---|---|---|---|---|
| Prostaglandin $A_1$ ethyl ester | | X | X | X | X | X | X | X | X |
| 15-epi Prostaglandin $A_1$ | | ◯ 10 μM | X | ◯ 10 μM | ◯ 10 μM | ◯ 10 μM | X | X | X |
| 16,16-dimethyl Prostaglandin $A_1$ | | X | X | X | X | X | X | X | X |

TABLE 10

| Compound | Structure | | | | | | | | |
|---|---|---|---|---|---|---|---|---|---|
| 13,14-dihydro-15-keto Prostaglandin A$_2$ | 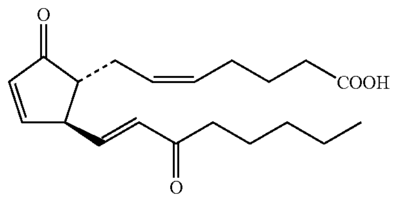 | X | X | X | X | X | X | X | X |
| 15(R)-15-methyl Prostaglandin A$_2$ | 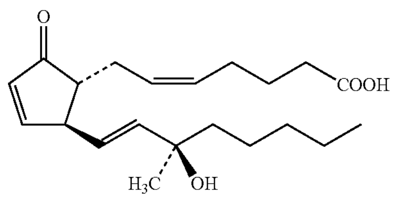 | ○ 10 μM | X | ○ 10 μM | ○ 10 μM | ○ 10 μM | X | ○ 10 μM | X |
| 15-deoxy-Δ$^{12,14}$-Prostaglandin A$_2$ | | X | X | X | X | X | X | X | X |
| 16-phenoxy tetranor Prostaglandin A$_2$ | 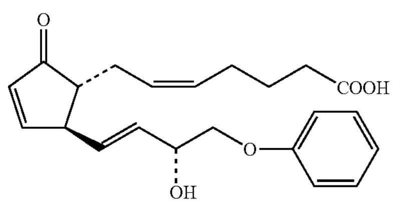 | X | X | X | ○ 30 μM | ○ 10 μM | X | ○ 30 μM | ○ 30 μM |

TABLE 11

| Compound | Structure | | | | | | | | |
|---|---|---|---|---|---|---|---|---|---|
| 17-phenyl trinor Prostaglandin A$_2$ | 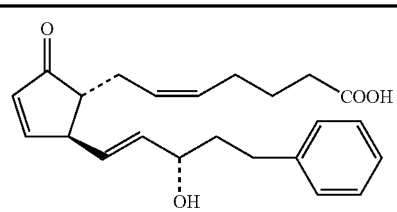 | ○ 10 μM | X | ○ 10 μM | X | ○ 10 μM | X | ○ 10 μM | X |
| 17-phenyl trinor-13,14-dihydro Prostaglandin A$_2$ | 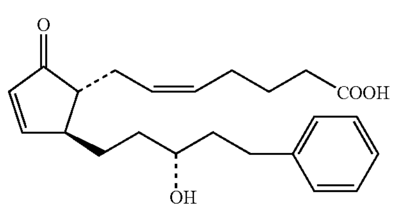 | X | X | X | X | X | X | X | X |
| 19(R)-hydroxy Prostaglandin A$_2$ | 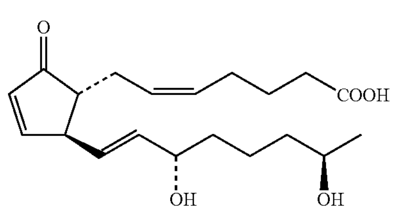 | X | X | X | X | X | X | X | X |

TABLE 11-continued

| Compound | Structure | 1 | 2 | 3 | 4 | 5 | 6 | 7 | 8 |
|---|---|---|---|---|---|---|---|---|---|
| 15-deoxy-Δ$^{12,14}$-Prostaglandin A$_1$ | (structure) | O 30 μM | X | O 30 μM | X | X | X | X | X |

TABLE 12

| Compound | Structure | 1 | 2 | 3 | 4 | 5 | 6 | 7 | 8 |
|---|---|---|---|---|---|---|---|---|---|
| Prostaglandin J$_2$ | (structure) | X | X | X | X | X | X | X | X |
| 15-deoxy-Δ$^{12,14}$-Prostaglandin J$_2$ | (structure) | X | X | O 10 μM | O 10 μM | O 10 μM | X | X | X |
| Δ12-Prostaglandin J$_2$ | (structure) | X | X | X | X | X | X | X | X |
| 9,10-dihydro-15-deoxy-Δ$^{12,14}$-Prostaglandin J$_2$ (CAY10410) | (structure) | X | X | X | X | X | X | X | X |
| 8-iso Prostaglandin A$_1$ | (structure) | O 10 μM | ND | O 3 μM | ND | O 10 μM | ND | O 10 μM | ND |

EXAMPLE 3

Expression Analysis of the TINUR Gene

TINUR, a β-type of the nuclear orphan receptor subfamily, was not selected from expression comparison analysis by DD and GeneChip using clinical peripheral blood samples. This receptor's association with specific diseases, including allergic diseases, has not been very clearly elucidated. However, since TINUR was predicted to have functional similarity with TR3, expression comparison with TINUR was carried out between healthy subjects and patients in the same manner as for TR3, that is, using ABI7700 and the same patient peripheral blood eosinophil panel (Table 5) in which the number of examples in a group amounts to more than ten. The primers and probe used for the TaqMan method were the following:

```
Primer 1 (5'):   AGCACAGGCTACGACGTCAA       (SEQ ID
                                            NO:8)
Primer 2 (3'):   TCTTCTACCTTAATGGAGGACTGC   (SEQ ID
                                            NO:9)
TaqMan probe:    TTGTACCAAATGCCCCTGTCCGGA   (SEQ ID
                                            NO:10)
```

Figure 5:
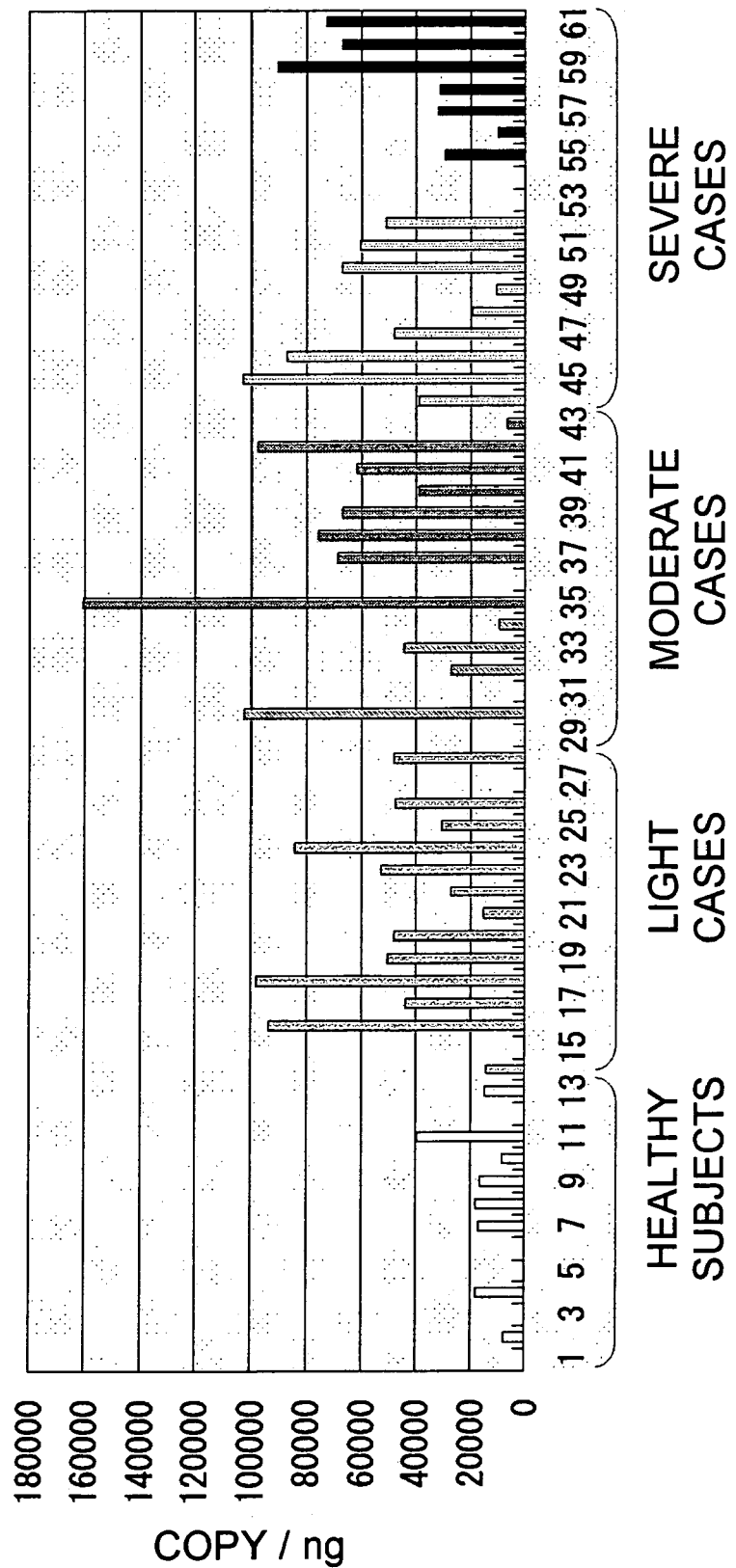
FIG. 5 shows a graph demonstrating the results of measuring the expression levels of the TINUR gene in healthy subjects and patients using ABI7700.

As shown in Table 13 and FIG. 5, significant enhancement was confirmed in atopic dermatitis patients as compared to normal subjects, regardless of case severity.

TABLE 13

| C1E-2 TINUR | Blood | β-actin (raw) copy/ng | TINUR (raw) copy/5 ng | TINUR (raw) copy/1 ng | For β-correction raw(/ng)/average | TINUR-correction raw/beta-correction |
|---|---|---|---|---|---|---|
| 13 healthy subjects | 1 | 253126 | | 0 | 1.01130301 | 0 |
| | 2 | 541166 | 81382 | 16276 | 2.16209434 | 7528 |
| | 3 | 214239 | | 0 | 0.855938946 | 0 |
| | 4 | 369621 | 136368 | 27274 | 1.476729393 | 18469 |
| | 5 | 716536 | | 0 | 2.862741935 | 0 |
| | 6 | 169173 | | 0 | 0.675887508 | 0 |
| | 7 | 601310 | 203504 | 40701 | 2.40238633 | 16942 |
| | 8 | 213062 | 78318 | 15664 | 0.851236036 | 18401 |
| | 9 | 371589 | 121882 | 24376 | 1.484591854 | 16420 |
| | 10 | 646297 | 105612 | 21122 | 2.582119848 | 8180 |
| | 11 | 208737 | 165619 | 33124 | 0.833956352 | 39719 |
| | 12 | 212114 | | 0 | 0.84744903 | 0 |
| | 13 | 379539 | 112142 | 22428 | 1.516355526 | 14791 |
| 15 light cases | 14 | 508758 | 146688 | 29338 | 2.032618527 | 14433 |
| | 15 | 248937 | | 0 | 0.994564691 | 0 |
| | 16 | 221813 | 414582 | 82916 | 0.886198604 | 93564 |
| | 17 | 315168 | 275505 | 55101 | 1.259174796 | 43760 |
| | 18 | 141827 | 279290 | 55858 | 0.566636769 | 98578 |
| | 19 | 244028 | 246709 | 49342 | 0.974953584 | 50609 |
| | 20 | 348051 | 332180 | 66436 | 1.390552351 | 47777 |
| | 21 | 387693 | 119505 | 23901 | 1.548931234 | 15431 |
| | 22 | 268468 | 144812 | 28962 | 1.072599907 | 27002 |
| | 23 | 206673 | 216900 | 43380 | 0.825709955 | 52537 |
| | 24 | 136652 | 228928 | 45786 | 0.545959033 | 83863 |
| | 25 | 218963 | 135292 | 27058 | 0.874812329 | 30930 |
| | 26 | 209273 | 198420 | 39684 | 0.836097009 | 47463 |
| | 27 | 131977 | | 0 | 0.52728236 | 0 |
| | 28 | 121064 | 115898 | 23180 | 0.483680797 | 47923 |
| 6 moderate cases in the remission stage | 29 | 165901 | | 0 | 0.662815331 | 0 |
| | 30 | 134119 | 273684 | 54737 | 0.535841346 | 102151 |
| | 31 | 86340 | | 0 | 0.344949082 | 0 |
| | 32 | 472440 | 259151 | 51830 | 1.887519071 | 27459 |
| | 33 | 170914 | 151666 | 30333 | 0.682845244 | 44422 |
| | 34 | 367818 | 71428 | 14286 | 1.469525949 | 9721 |
| 9 moderate cases in the exacerbation stage | 35 | 162258 | 519205 | 103841 | 0.648261218 | 160184 |
| | 36 | 90969 | | 0 | 0.363443211 | 0 |
| | 37 | 246460 | 338300 | 67660 | 0.984671042 | 68713 |
| | 38 | 146805 | 221751 | 44350 | 0.586522301 | 75616 |
| | 39 | 179179 | 240130 | 48026 | 0.715863818 | 67088 |
| | 40 | 138858 | 107895 | 21579 | 0.554771366 | 38897 |
| | 41 | 133317 | 163876 | 32775 | 0.532635051 | 61534 |
| | 42 | 171308 | 333904 | 66781 | 0.684419966 | 97573 |
| | 43 | 285295 | 38321 | 7664 | 1.139827753 | 6724 |
| 10 severe cases in the remission stage | 44 | 154902 | 121579 | 24316 | 0.618872876 | 39290 |
| | 45 | 78948 | 162181 | 32436 | 0.315418709 | 102835 |
| | 46 | 231612 | 402817 | 80563 | 0.925346905 | 87063 |
| | 47 | 155564 | 149795 | 29959 | 0.621516584 | 48203 |
| | 48 | 385848 | 148392 | 29678 | 1.541561787 | 19252 |
| | 49 | 264744 | 56146 | 11229 | 1.05772078 | 10616 |
| | 50 | 144715 | 194006 | 38801 | 0.578174465 | 67110 |
| | 51 | 205943 | 249286 | 49857 | 0.822795017 | 60595 |
| | 52 | 155395 | 157681 | 31536 | 0.62084169 | 50796 |
| | 53 | 151703 | | 0 | 0.606092505 | 0 |
| 8 severe cases in the exacerbation stage | 54 | 397821 | | 0 | 1.589395971 | 0 |
| | 55 | 446400 | 263974 | 52795 | 1.783480045 | 29602 |
| | 56 | 280724 | 54818 | 10964 | 1.121564845 | 9775 |
| | 57 | 161385 | 102355 | 20471 | 0.644775207 | 31749 |
| | 58 | 134978 | 85303 | 17061 | 0.539271624 | 31637 |
| | 59 | 24740 | 44743 | 8949 | 0.0988414 | 90534 |
| | 60 | 241793 | 322099 | 64420 | 0.966023991 | 66686 |
| | 61 | 93068 | 135613 | 27123 | 0.371831799 | 72943 |
| | total | 15268113 | | | | |
| | Av. | 250297 | | | | |

EXAMPLE 4

TINUR Receptor Ligand Search

Like TR3, TINUR is an orphan nuclear receptor whose native ligands and activators are still unknown. If discovered, they may directly activate TINUR in eosinophil cells and promote apoptosis. Such ligand activators would therefore be anti-allergic agents, and thus a high-throughput system for ligand screening was constructed, using the same methods as for TR3.

The TINUR ligand binding domain sequence or full length gene (FIG. 3) was inserted into pBIND as shown in FIG. 2, in order to facilitate expression of a protein in which the DNA binding domains of TINUR and GAL4 are fused in frame. A plasmid comprising the TINUR ligand binding domain sequence inserted into pBIND, and a luciferase reporter plasmid comprising a GAL4 binding site, were co-transfected into NIH3T3 cells. Luciferase activity was measured automatically. At the same time, activity measurement was also carried out by adding retinoic acid X receptor (RXR) α-gene, a transcription factor that forms a heterodimer with TINUR. Low molecular weight substances can also be added to this system to screen using transcriptional enhancement activity.

Figure 6:
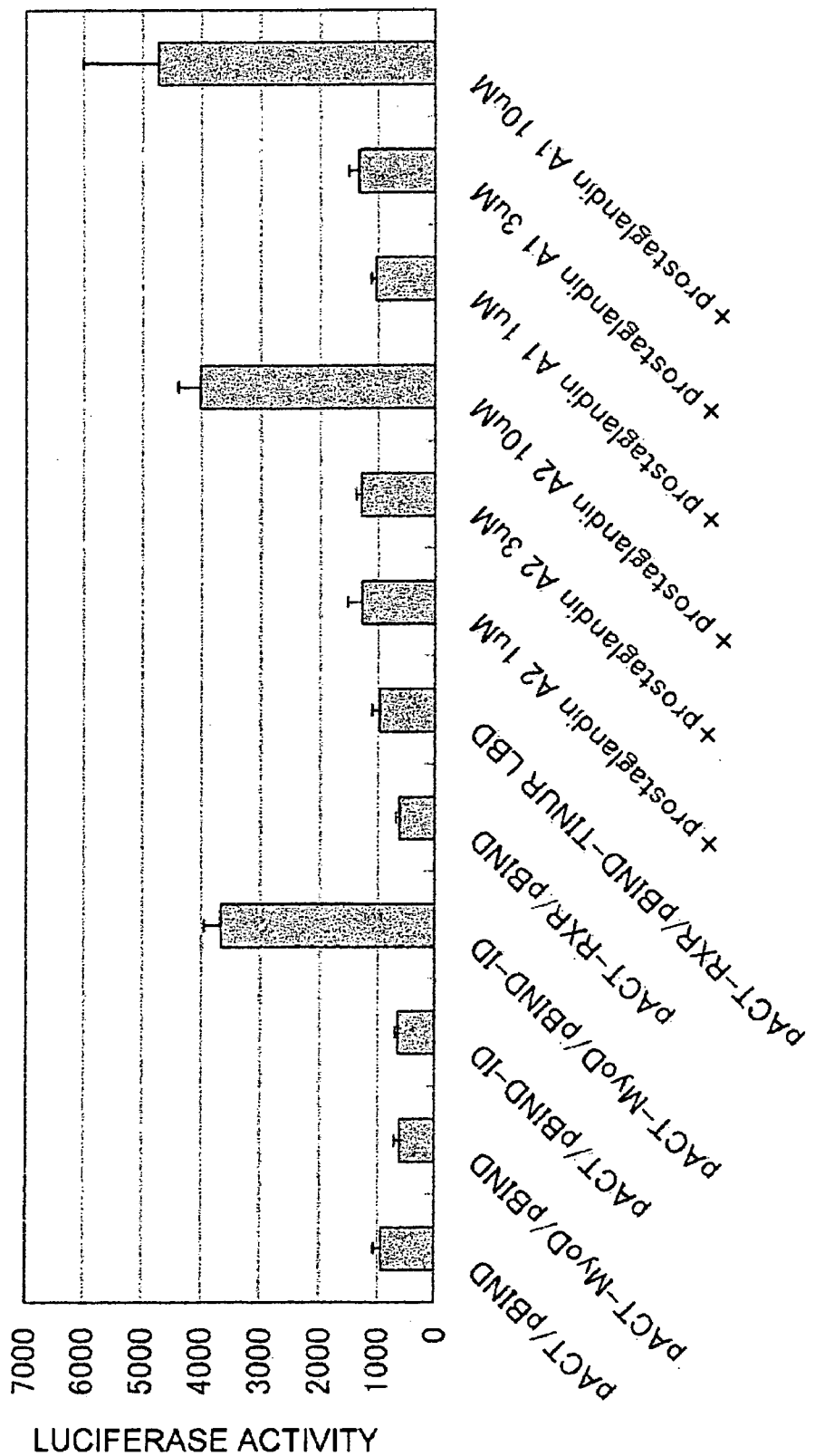
FIG. 6 shows a graph demonstrating the transcription-activating function of the TINUR gene in a series of cyclopentenone prostaglandins using the system of FIG. 2.

Like TR3 expression, TINUR expression is enhanced in activated eosinophils. Ligands existing in vivo may exist in sites where nuclear receptors are highly expressed. The native ligands of TR3 were found to be prostaglandin $A_2$ and prostaglandin $A_1$. Ligands of the nuclear receptor subfamily are assumed to have structural redundancy. Therefore, derivatives similar to TR3 activator compounds were added, and enhancement of transcriptional activity was investigated. Compounds found to comprise the activity of activating TINUR transcription were prostaglandins comprising a cyclopentenone structure, such as prostaglandin $A_2$, prostaglandin $A_1$, 15-epi prostaglandin $A_1$, 15(R)-15-methyl prostaglandin $A_2$, 16-phenoxy tetranor prostaglandin $A_2$, 17-phenyl trinor prostaglandin $A_2$, 15-deoxy-delta 12,14-prostaglandin $J_2$ and 8-isoprostaglandin $A_1$ (FIG. 6, Tables 8 to 12). According to the X-ray crystallography results of Wang et al, the TINUR (Nurr1) ligand pocket is closed, suggesting it may be a nuclear receptor without a native ligand (Z. Wang, G. Benoit, J. Liu, S. Prasad, P. Aarnisalo, X. Liu, H. Xu, N. P. C. Walker, T. Perlmann, "Structure and function of Nurr1 identifies a class of ligand-independent nuclear receptors" (Tularik Inc.); Nature 423, 29 May, p 555–560 (2003)). However, since the above-mentioned reactions are reproducible, and structure-activity relationships exist in compounds similar to prostaglandin $A_2$, the present inventors revealed that there is a strong possibility that compounds such as prostaglandin $A_2$, prostaglandin $A_1$, and similar metabolites are native ligands of not only TR3, but also of TINUR.

EXAMPLE 5

Virtual Compounds

Figure 7:
FIG. 7 shows diagram of prostaglandin $A_2$ in alpha model, in which the binding position of the PGA derivative for the TR3 ligand binding domain has been simulated using the Pharmacophore model.

A pharmacophore model was used to simulate the binding position of the PGA derivatives to the TR3 ligand binding domain (LBS) (FIG. 7). Based on structure-activity relationship information for the PGA derivative reporter system, compounds other than PGA derivatives that matched the binding pocket were selected from the Catalyst database (screened from BioByte Master File 2001 39,383 compounds, 2,198,646 conformations).

The 158 compounds selected as strongly binding compounds using this simulation are shown in Tables 14 to 45 (including the structural formula). The 117 compounds subsequently selected are shown in Tables 46 to 49.

TABLE 14

| Compound | LUDI_ score | HB_ score | LIPO_ score |
|---|---|---|---|
| 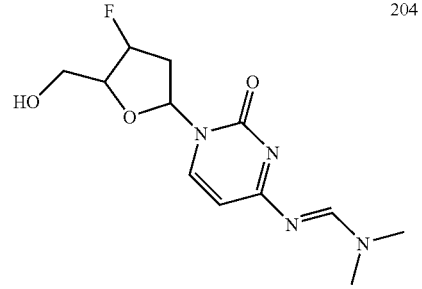 2DEOXY3FLUORO CYTIDINEN4DIMETHYL AMINOMETHYLENE | 204 | 0 | 325 |
| 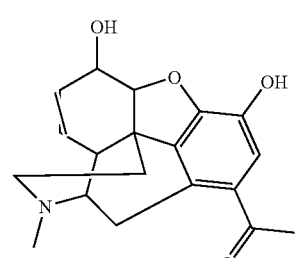 1ACETOMORPHINE | 158 | 0 | 254 |
| 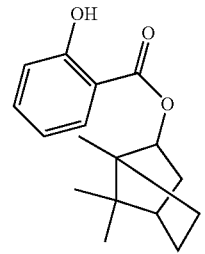 BORNYLSALICYLATE | 151 | 0 | 272 |
| 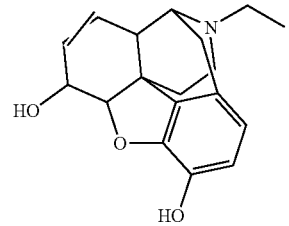 NETHYLMORPHINE | 136 | 0 | 257 |
| 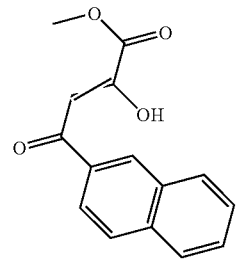 2HYDROXY42NAPHTHALENYL 4OXO2BUTENOICACID METHYLESTER | 126 | 0 | 222 |

TABLE 15
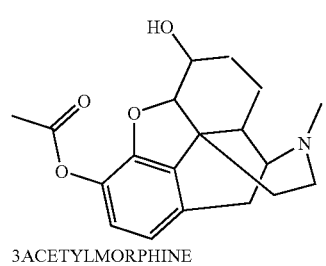
3ACETYLMORPHINE
123  0  219
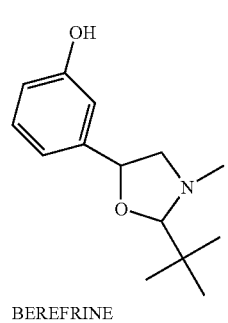
BEREFRINE
112  0  233
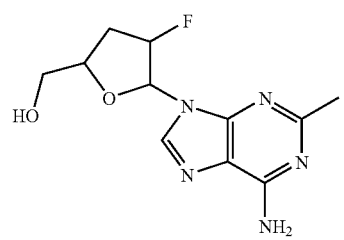
DIDEOXYARAA
2METHYL2FLUORO
112  83  150
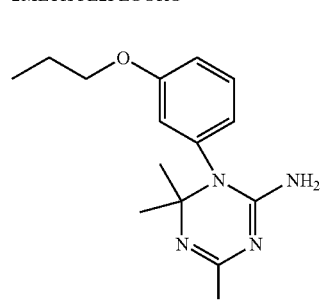
STRIAZINE46DIAMINO
12H222DIMETHYL
13PROPOXYPHENYL
108  0  254
TABLE 16
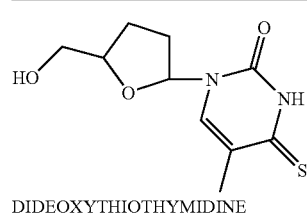
DIDEOXYTHIOTHYMIDINE
107  83  145
TABLE 16-continued
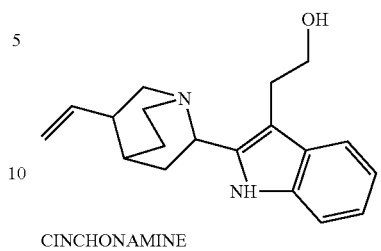
CINCHONAMINE
103  0  275
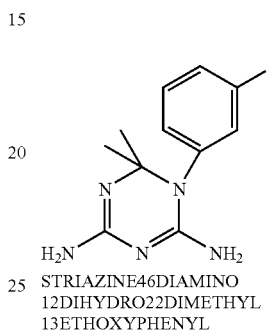
STRIAZINE46DIAMINO
12DIHYDRO22DIMETHYL
13ETHOXYPHENYL
103  0  224
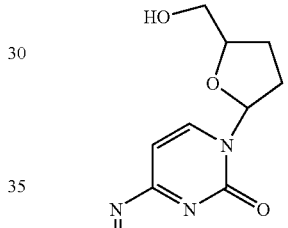
23DIDEOXYCYTIDINEN
4DIMETHYLAMINOMETHYLENE
101  0  222
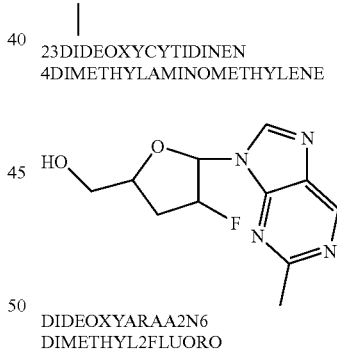
DIDEOXYARAA2N6
DIMETHYL2FLUORO
101  0  222
TABLE 17
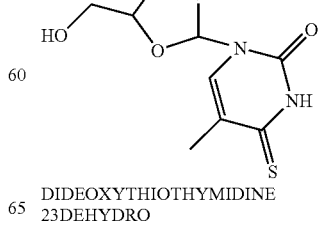
DIDEOXYTHIOTHYMIDINE
23DEHYDRO
101  72  150

TABLE 17-continued
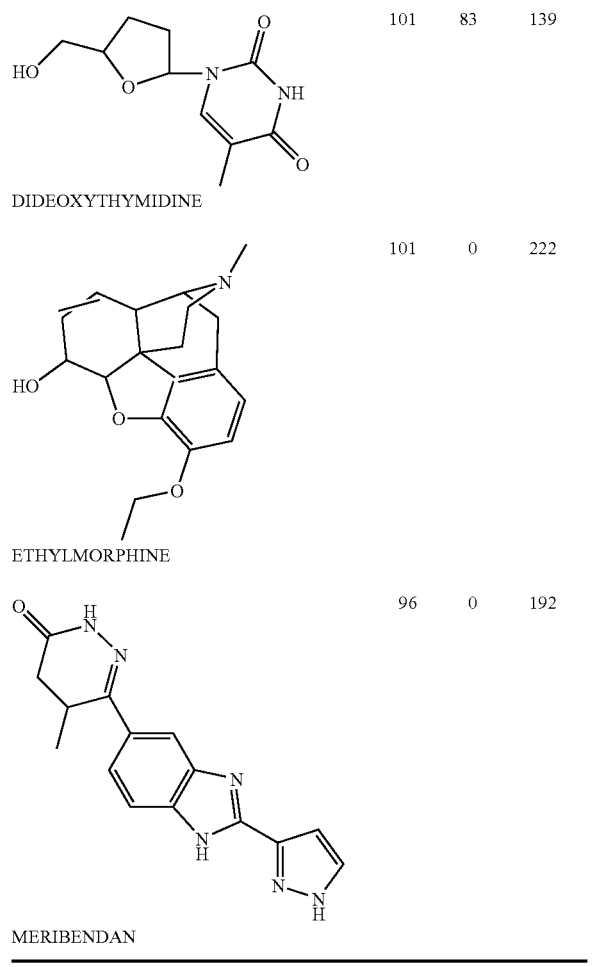
| Compound | | | |
|---|---|---|---|
| DIDEOXYTHYMIDINE | 101 | 83 | 139 |
| ETHYLMORPHINE | 101 | 0 | 222 |
| MERIBENDAN | 96 | 0 | 192 |
TABLE 18
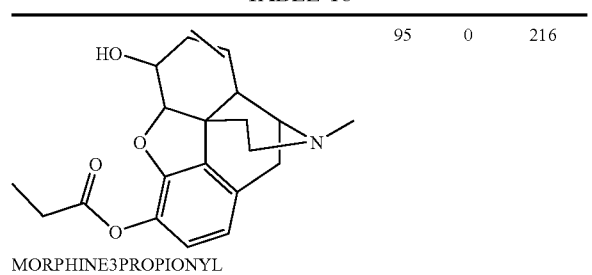
MORPHINE3PROPIONYL 95 0 216
TABLE 18-continued
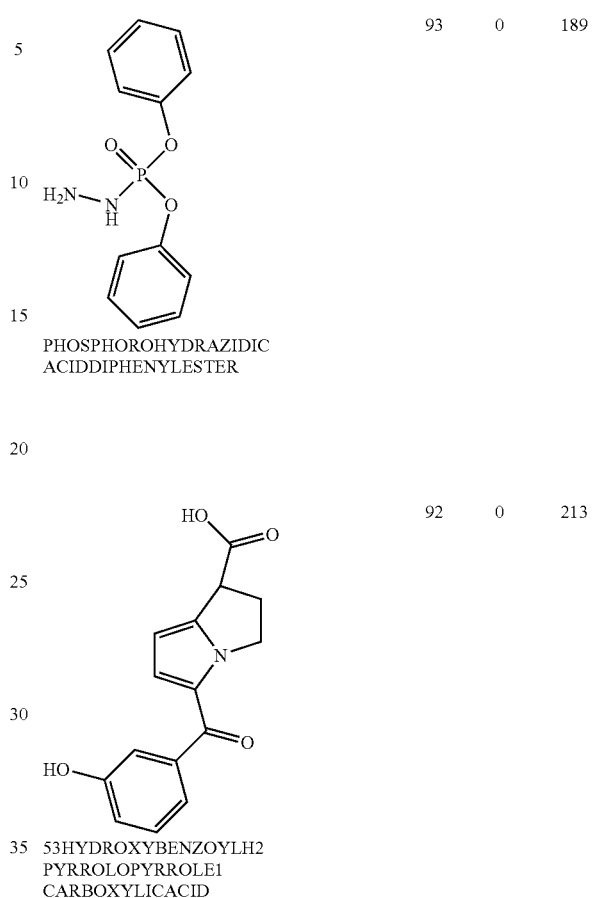
| Compound | | | |
|---|---|---|---|
| PHOSPHOROHYDRAZIDIC ACIDDIPHENYLESTER | 93 | 0 | 189 |
| 53HYDROXYBENZOYLH2 PYRROLOPYRROLE1 CARBOXYLICACID | 92 | 0 | 213 |
| OXAZEPAM | 90 | 0 | 236 |
TABLE 19
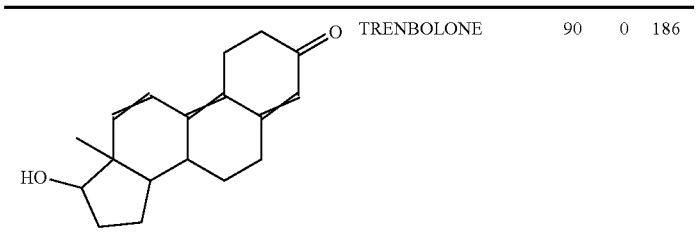
TRENBOLONE 90 0 186

TABLE 19-continued

| Structure | Name | | | |
|---|---|---|---|---|
| (structure) | STAVUDINE | 89 | 74 | 136 |
| (structure) | THYMINE123DIDEOXY 2FLUOROPENTO FURANOSYL | 89 | 83 | 127 |
| (structure) | ALOVUDINE | 87 | 63 | 145 |

TABLE 20

| Structure | Name | | | |
|---|---|---|---|---|
| (structure) | NAPROXOL | 87 | 0 | 233 |
| (structure) | MDL72638 | 86 | 0 | 207 |

TABLE 20-continued

| Structure | Name | | | |
|---|---|---|---|---|
| (structure) | 12DIHYDRO TRIAZINE46 DIAMINO22 DIMETHYL13 METHOXYPHENYL | 84 | 0 | 180 |
| (structure) | 4QUINOLINAMINE 2PAMINOSTYRYL | 84 | 0 | 180 |

TABLE 21

| Structure | Name | | | |
|---|---|---|---|---|
| (structure) | 2AMINO4PHENYL QUINAZOLINE | 81 | 0 | 177 |
| (structure) | DIPHENYLACETAL DEHYDEENOL | 81 | 0 | 177 |
| (structure) | GUANABENZ | 81 | 0 | 177 |
| (structure) | MHYDROXY DIPHENYLAMINE | 81 | 0 | 177 |
| (structure) | PRECLAMOL | 81 | 0 | 227 |

TABLE 22

| Structure | Name | | | |
|---|---|---|---|---|
| (structure) | FENISOREX | 77 | 0 | 198 |
| (structure) | LY195115 | 75 | 0 | 171 |
| (structure) | PLATINUMBISCYCLO HEXYLAMMONIO DIAQUADINITRATE | 75 | 0 | 171 |
| (structure) | 11DIMETHYL33 AMINOPHENYL UREA | 72 | 0 | 168 |

TABLE 23

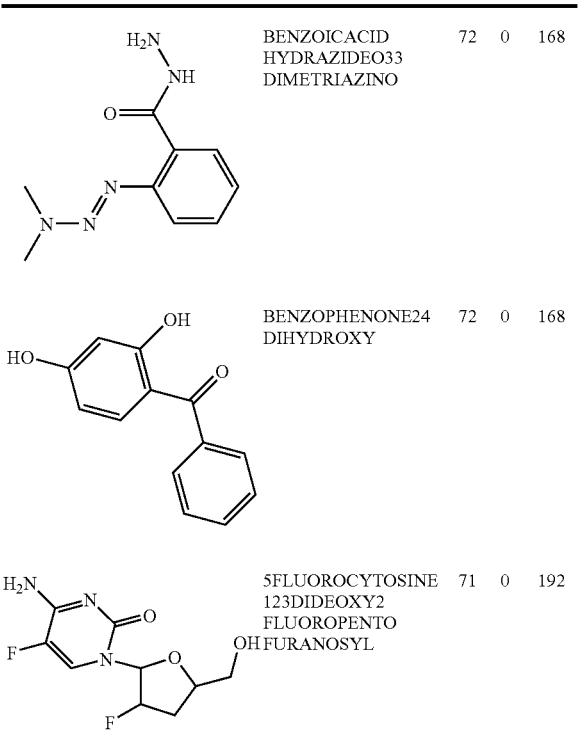

| Structure | Name | | | |
|---|---|---|---|---|
| 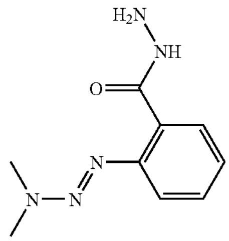 | BENZOICACID HYDRAZIDEO33 DIMETRIAZINO | 72 | 0 | 168 |
| 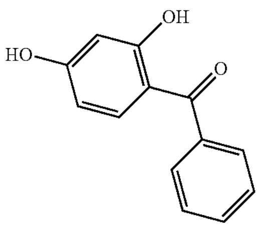 | BENZOPHENONE24 DIHYDROXY | 72 | 0 | 168 |
| 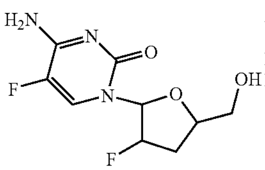 | 5FLUOROCYTOSINE 123DIDEOXY2 FLUOROPENTO FURANOSYL | 71 | 0 | 192 |

TABLE 23-continued

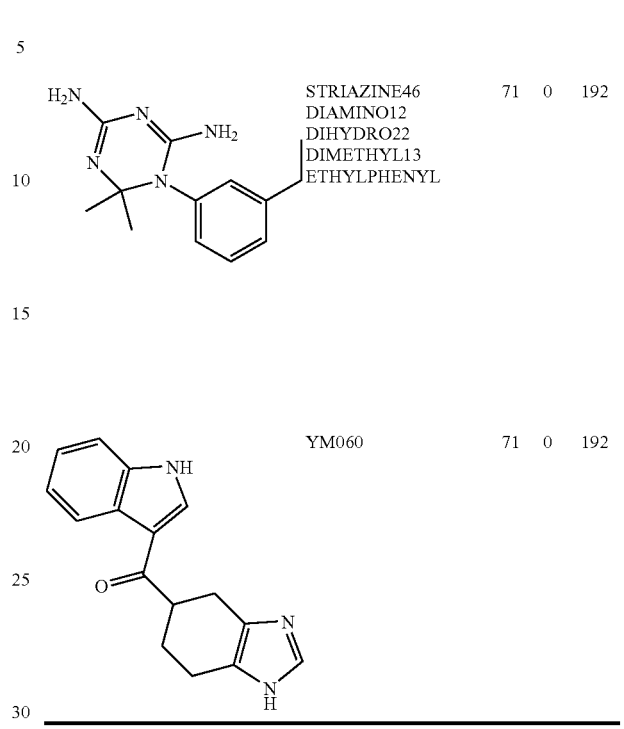

| Structure | Name | | | |
|---|---|---|---|---|
| 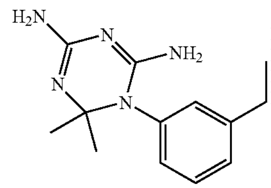 | STRIAZINE46 DIAMINO12 DIHYDRO22 DIMETHYL13 ETHYLPHENYL | 71 | 0 | 192 |
| 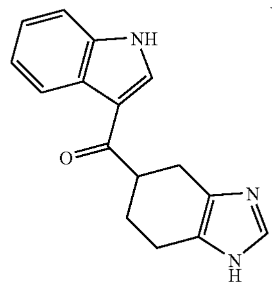 | YM060 | 71 | 0 | 192 |

TABLE 24

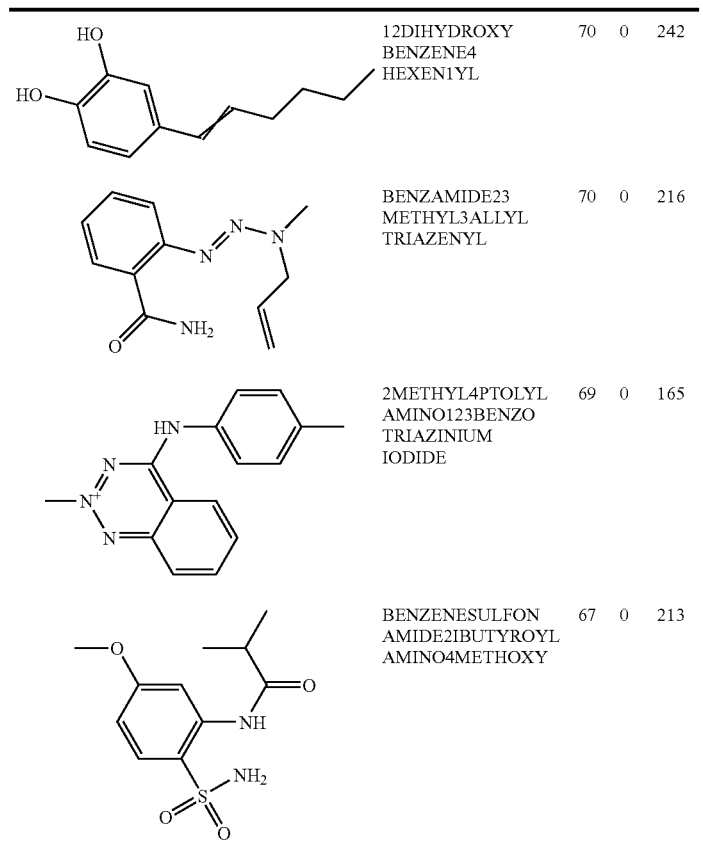

| Structure | Name | | | |
|---|---|---|---|---|
| 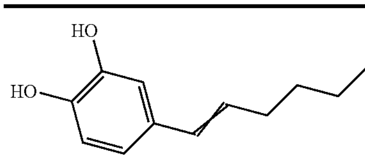 | 12DIHYDROXY BENZENE4 HEXEN1YL | 70 | 0 | 242 |
| 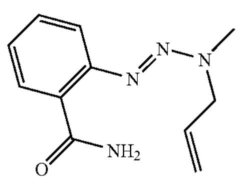 | BENZAMIDE23 METHYL3ALLYL TRIAZENYL | 70 | 0 | 216 |
| 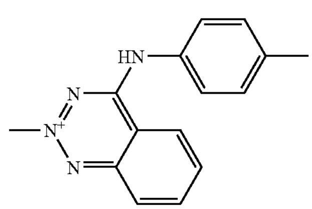 | 2METHYL4PTOLYL AMINO123BENZO TRIAZINIUM IODIDE | 69 | 0 | 165 |
| 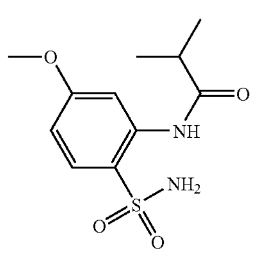 | BENZENESULFON AMIDE2IBUTYROYL AMINO4METHOXY | 67 | 0 | 213 |

TABLE 24-continued
| Structure | Name | | | |
|---|---|---|---|---|
| 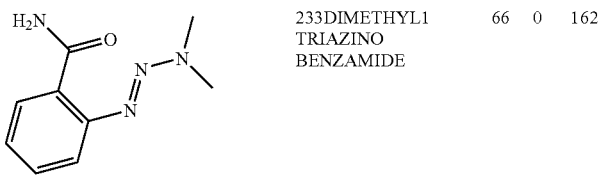 | 233DIMETHYL1 TRIAZINO BENZAMIDE | 66 | 0 | 162 |
| 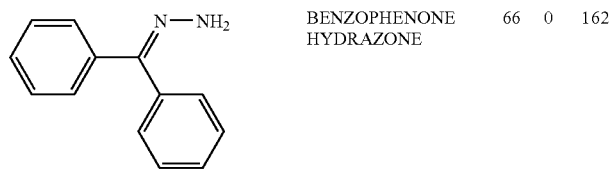 | BENZOPHENONE HYDRAZONE | 66 | 0 | 162 |
TABLE 25
| Structure | Name | | | |
|---|---|---|---|---|
| 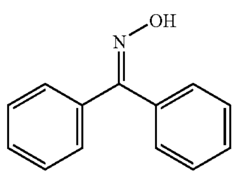 | BENZOPHENONE OXIME | 66 | 0 | 162 |
| 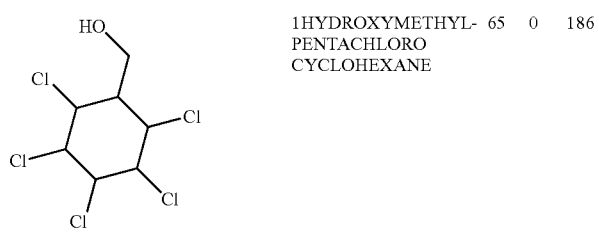 | 1HYDROXYMETHYL-PENTACHLORO CYCLOHEXANE | 65 | 0 | 186 |
| 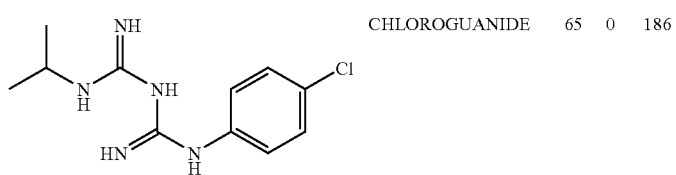 | CHLOROGUANIDE | 65 | 0 | 186 |
| 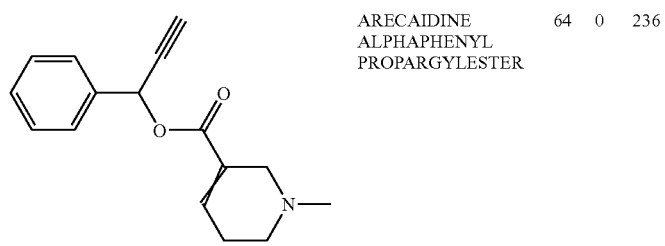 | ARECAIDINE ALPHAPHENYL PROPARGYLESTER | 64 | 0 | 236 |
| 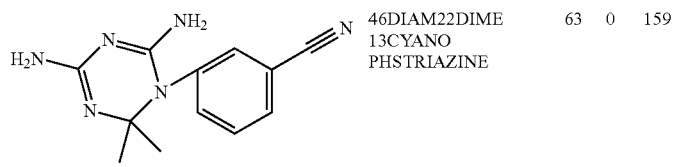 | 46DIAM22DIME 13CYANO PHSTRIAZINE | 63 | 0 | 159 |

TABLE 25-continued

| Structure | Name | | | |
|---|---|---|---|---|
| 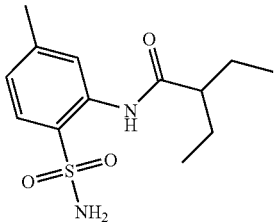 | BENZENESULFON AMIDE22ETHYL BUTANOYLAMINO 4METHYL | 63 | 0 | 260 |

TABLE 26

| Structure | Name | | | |
|---|---|---|---|---|
| 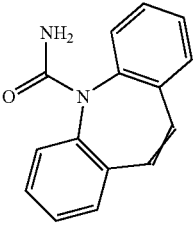 | CARBAMAZEPINE | 63 | 0 | 159 |
| 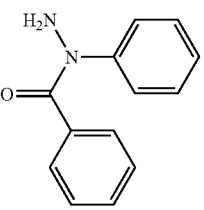 | N1PHENYL N1BENZOYL HYDRAZINE | 63 | 0 | 159 |
| 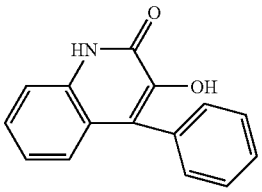 | VIRIDICATIN | 63 | 0 | 159 |
| 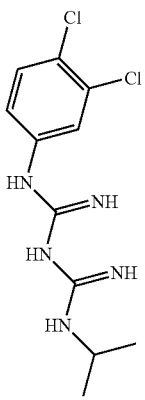 | CHLORPROGUANIL | 62 | 0 | 183 |
| 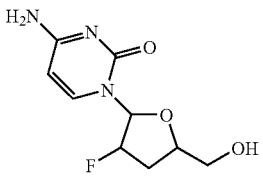 | DIDEOXYCYTIDINE 2ALPHAFLUORO | 62 | 0 | 183 |

TABLE 27

| Structure | Name | | | |
|---|---|---|---|---|
| 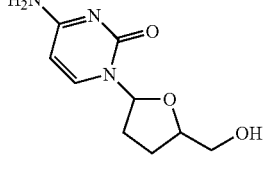 | ZALCITABINE | 62 | 0 | 183 |
| 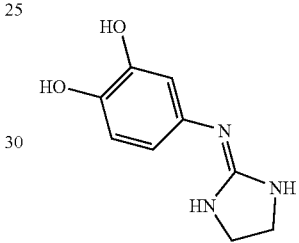 | 234DIHYDROXY PHENYLIMINOIMI DAZOLIDINE | 60 | 0 | 156 |
| 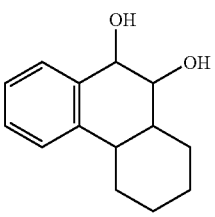 | 23BENZO OCTAHYDRO NAPHTHALENE E34DIOH34DIAX | 60 | 0 | 156 |
| 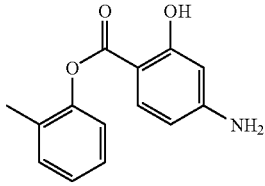 | 4AMINOSALICYLIC ACID2TOLYLESTER | 60 | 0 | 156 |
| 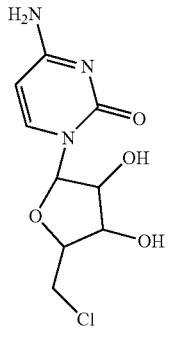 | 5CHLOROCYTIDINE | 60 | 63 | 118 |

TABLE 28
| Structure | Name | | | |
|---|---|---|---|---|
| 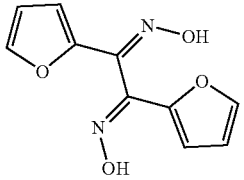 | AFURILDIOXIME | 60 | 0 | 156 |
| 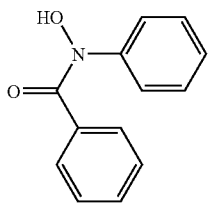 | BENZOYLPHENYL HYDROXYLAMINE | 60 | 0 | 156 |
| 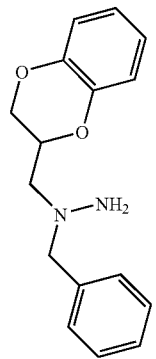 | DOMOXIN | 60 | 0 | 257 |
| 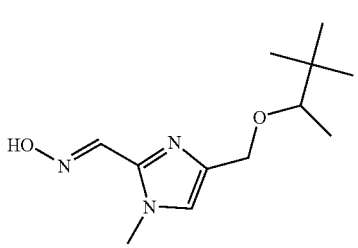 | IMIDAZOLE1 METHYL2HYDROXY IMINOMETHYL412 DIMETHYLPRO POXYETHYL | 60 | 0 | 257 |
TABLE 29
| Structure | Name | | | |
|---|---|---|---|---|
| 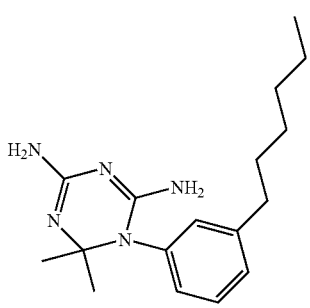 | 46DIAM12HSYM TRIAZINE1MHEXYLPHENYL | 59 | 0 | 281 |
TABLE 29-continued
| Structure | Name | | | |
|---|---|---|---|---|
| 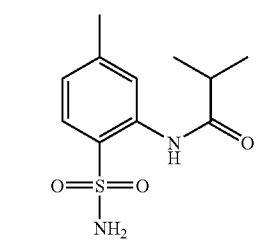 | BENZENESULFONAMIDE 2IBUTYROYLAMINO4METHYL | 58 | 0 | 204 |

TABLE 29-continued

| Structure | | | |
|---|---|---|---|
| 11DIPHENYLUREA | 57 | 0 | 153 |
| 12DIHYDROTRIAZINE 22DIMETHYL46DIAMINO 13METHYLPHENYL | 57 | 0 | 153 |
| AFURILMONOXIME | 57 | 0 | 153 |

TABLE 30

| Structure | | | |
|---|---|---|---|
| DIACETONEGLUCOSE | 57 | 0 | 153 |
| PYRIDINE2PHENACYLENOL | 57 | 0 | 153 |
| DIDEOXYCYTIDINE 5FLUORO | 56 | 0 | 177 |

TABLE 30-continued

| Structure | | | |
|---|---|---|---|
| UREA1ETHYL1 METHOXYPHENYL | 55 | 0 | 201 |
| PYRIDO12APYRIMIDIN 4ONE3CONH2H716DIMEAX | 54 | 0 | 150 |

TABLE 31

| Structure | | | |
|---|---|---|---|
| PHENOL26DIMETHYL OL4METHYL | 53 | 66 | 133 |
| 2CYCLOHEXYLPHENOL | 52 | 0 | 148 |
| 5AMINO1245TRICHLORO PHENYLTETRAZOLE | 52 | 0 | 148 |

TABLE 31-continued

| Structure | | | |
|---|---|---|---|
| BENZAMIDE23 AZETIDINYLTRIAZENE | 52 | 0 | 148 |
| BENZAMIDE23METHYL 3BUTYLTRIAZENYL | 52 | 0 | 224 |

TABLE 32

| Structure | | | |
|---|---|---|---|
| BENZENEMETHAN IMINEA3HYDROXY PHENYL | 52 | 0 | 148 |
| DICHLOROPHENARSINE | 52 | 0 | 148 |
| MEDETOMIDINE | 52 | 0 | 198 |

TABLE 32-continued

| Structure | | | |
|---|---|---|---|
| NAPHTHALENE2 AMINO4METHOXY CARBONYL | 52 | 0 | 148 |
| NAPHTHONONE | 52 | 0 | 148 |
| NNDIMETHYLCARBA MATEMAMINO BENZYLESTER | 52 | 0 | 198 |

TABLE 33

| Structure | | | |
|---|---|---|---|
| RO600213 | 52 | 0 | 198 |
| 5HYDROXY1METHYL 2AMINOTETRALINNPROPYL | 50 | 0 | 222 |
| BENZAMIDEODICHLORO ACETYLAMINO | 50 | 0 | 171 |

TABLE 33-continued

| Structure | | | |
|---|---|---|---|
| 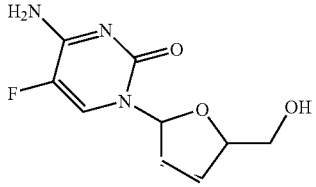 RA131423 | 50 | 0 | 171 |
| 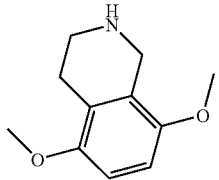 1234H4ISOQUINOLINE 58DIMETHOXY | 49 | 0 | 145 |

TABLE 34

| Structure | | | |
|---|---|---|---|
| 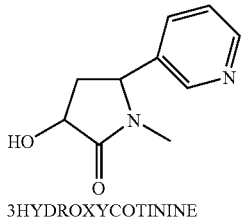 3HYDROXYCOTININE | 49 | 0 | 145 |
| 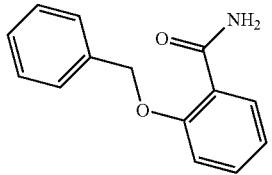 OBENZYLOXYBENZAMIDE | 49 | 0 | 195 |
| 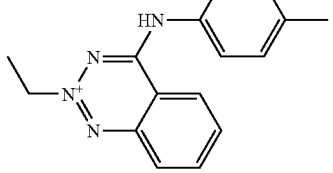 2ETHYL4PTOLYLAMINO 123BENZOTRIAZINIUMIODIDE | 47 | 0 | 168 |
| 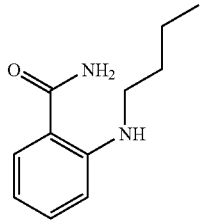 BENZAMIDEOBUTYLAMINO | 47 | 0 | 219 |

TABLE 34-continued

| Structure | | | |
|---|---|---|---|
| 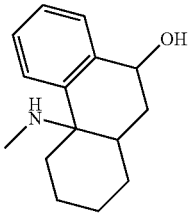 OCTAHYDRO PHENANTHREN4A AMINENMETHYL9HYDROXY | 47 | 0 | 168 |
| 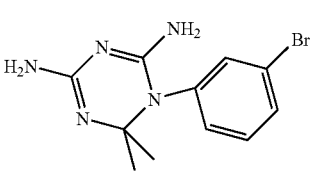 13BROMOPHENYL 22DIMETHYL46 DIAMINOSTRIAZINE | 46 | 0 | 142 |

TABLE 35

| Structure | | | |
|---|---|---|---|
| 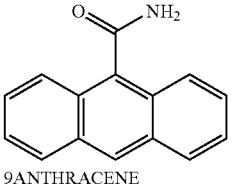 9ANTHRACENE CARBOXAMIDE | 46 | 0 | 142 |
| 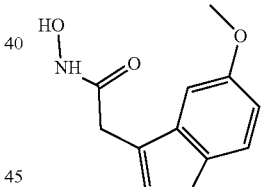 DEBOXAMET | 46 | 0 | 192 |
| 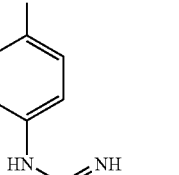 N1PCHLOROPHENYL N5PROPYLBIGUANIDE | 46 | 0 | 192 |

TABLE 35-continued

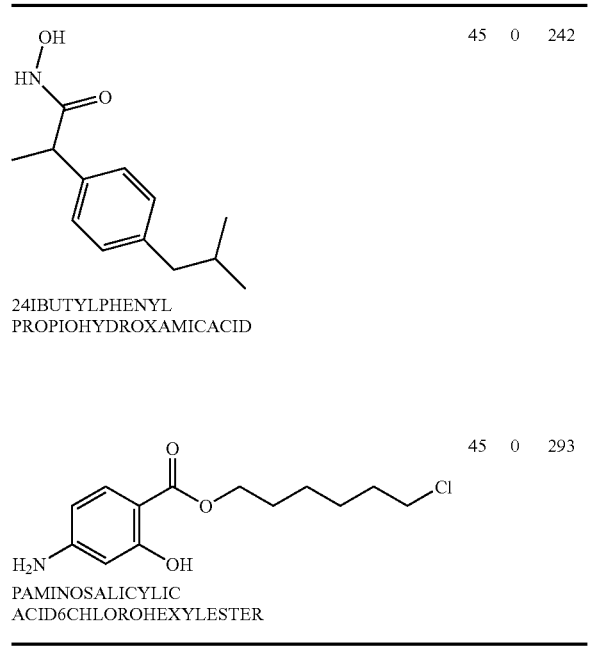

24IBUTYLPHENYL
PROPIOHYDROXAMICACID
45 0 242

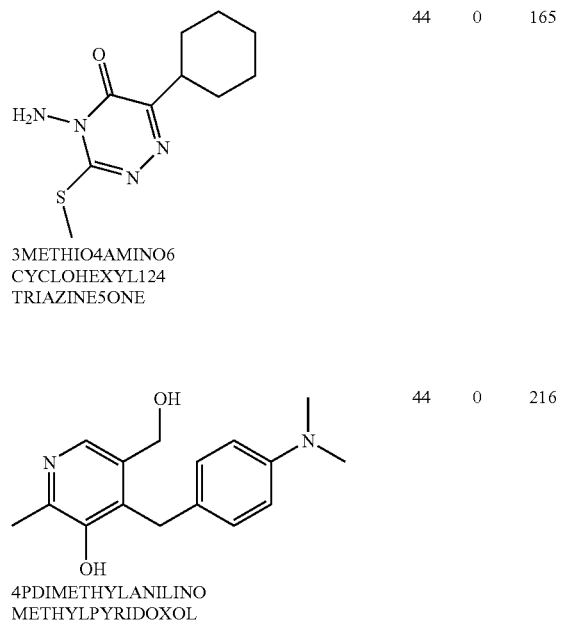

PAMINOSALICYLIC
ACID6CHLOROHEXYLESTER
45 0 293

TABLE 36

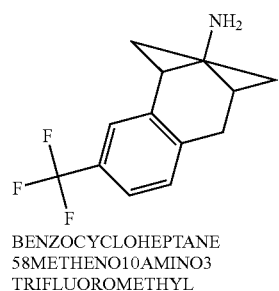

3METHIO4AMINO6
CYCLOHEXYL124
TRIAZINE5ONE
44 0 165

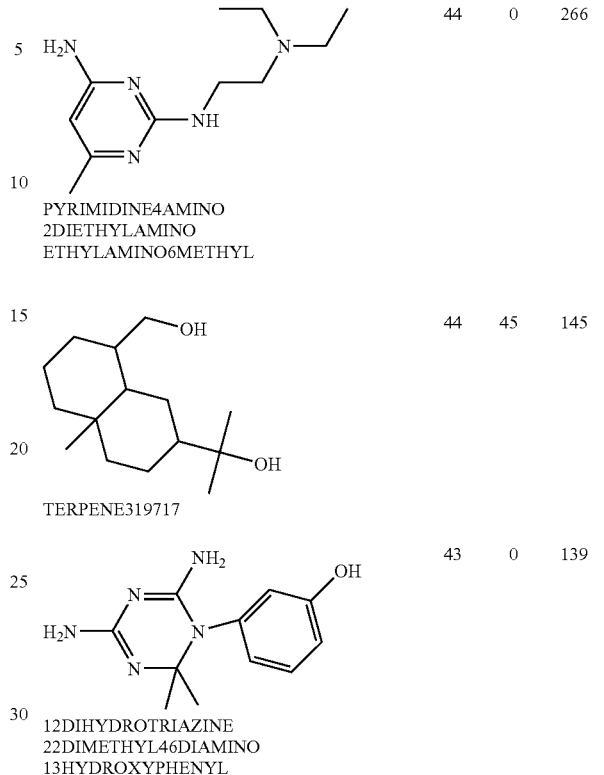

4PDIMETHYLANILINO
METHYLPYRIDOXOL
44 0 216

BENZOCYCLOHEPTANE
58METHENO10AMINO3
TRIFLUOROMETHYL
44 0 165

TABLE 36-continued

PYRIMIDINE4AMINO
2DIETHYLAMINO
ETHYLAMINO6METHYL
44 0 266

TERPENE319717
44 45 145

12DIHYDROTRIAZINE
22DIMETHYL46DIAMINO
13HYDROXYPHENYL
43 0 139

TABLE 37

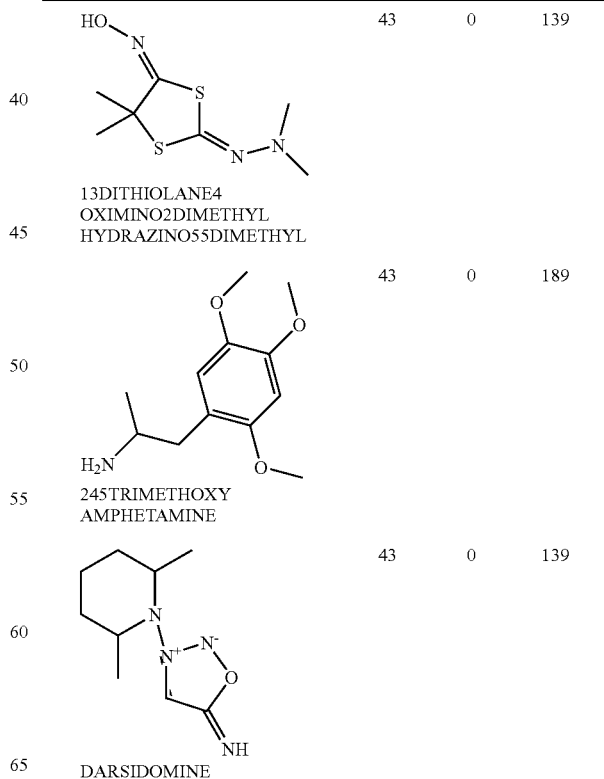

13DITHIOLANE4
OXIMINO2DIMETHYL
HYDRAZINO55DIMETHYL
43 0 139

245TRIMETHOXY
AMPHETAMINE
43 0 189

DARSIDOMINE
43 0 139

TABLE 37-continued

| Structure | | | |
|---|---|---|---|
| 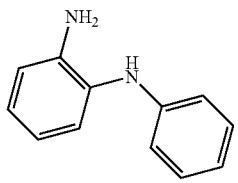 OAMINODIPHENYLAMINE | 43 | 0 | 139 |
| 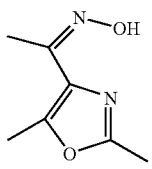 OXAZOLE4ACETOXIME25DIMETHYL | 43 | 0 | 139 |
| 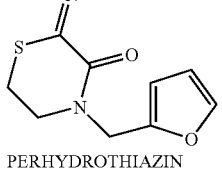 PERHYDROTHIAZIN3ONE2OXIMINON2FURANYLMETHYL | 43 | 0 | 189 |

TABLE 38

| Structure | | | |
|---|---|---|---|
| 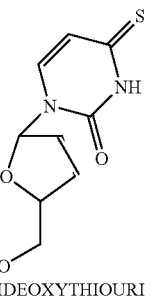 PYRIMIDINE24DIAMINO5BENZYL6METHYL | 43 | 0 | 189 |
| 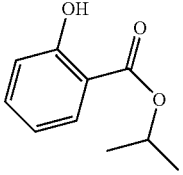 5NORBORNEN2YLHYDROXIMICACIDMETHYLESTER | 41 | 0 | 162 |

TABLE 38-continued

| Structure | | | |
|---|---|---|---|
| 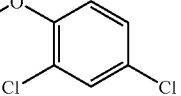 DIDEOXYTHIOURIDINE23DEHYDRO | 41 | 0 | 162 |
| 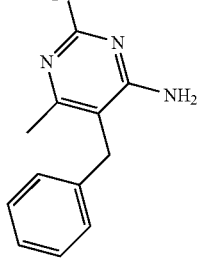 ISOPROPYLSALICYLATE | 41 | 0 | 162 |
| 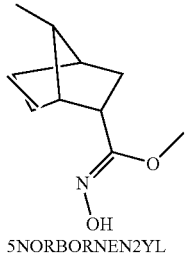 MDL72145 | 41 | 0 | 213 |

TABLE 39

| Structure | Name | | | |
|---|---|---|---|---|
| 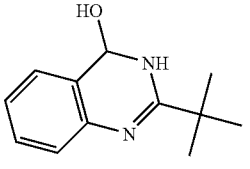 | QUINAZOLINE2TBUTYL34DIHYDRO4HYDROXY | 41 | 0 | 162 |
| 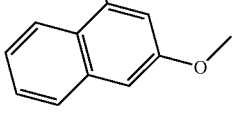 | 1NAPHTHALENEAMINE3METHOXY | 40 | 0 | 136 |
| 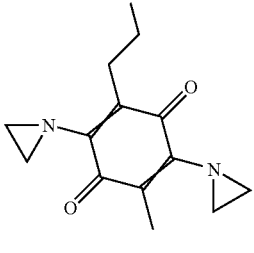 | BENZOQUINONE25BISAZIRIDINYL3METHYL6HYDROXYETHYL | 40 | 0 | 186 |

TABLE 39-continued

| Structure | Name | | | |
|---|---|---|---|---|
| (naphthyl-O-C(CH3)=N-OH with NH2) | NAPRODOXIME | 40 | 0 | 186 |
| (2-phenoxyaniline) | OPHENOXYANILINE | 40 | 0 | 136 |
| (2-cyclopentylphenol) | PHENOL2 CYCLOPENTYL | 40 | 0 | 136 |

TABLE 40

| Structure | Name | | | |
|---|---|---|---|---|
| (2,6-dichlorophenyl tetrahydropyrimidinylamine) | ST404 | 40 | 0 | 136 |
| (N-ethyl-N-(4-methoxyphenyl)urea) | UREA1ETHYL1 PANISYL | 38 | 0 | 159 |
| (5-phenyl-4-propyl-1,2-dihydropyrazol-3-one) | 12DIHYDROPYRA ZOLONE4PROPYL5 PHENYL | 37 | 0 | 183 |
| (7-methoxy-3-aminochroman) | 24DIMETHOXY AMPHETAMINE | 37 | 0 | 183 |

TABLE 40-continued

| Structure | Name | | | |
|---|---|---|---|---|
| (2-aminobiphenyl) | 2AMINOBIPHENYL | 37 | 0 | 133 |
| (1-(3-aminophenyl)-2-pyridone) | AMPHENIDONE | 37 | 0 | 133 |

TABLE 41

| Structure | Name | | | |
|---|---|---|---|---|
| (2-isobutyrylamino benzenesulfonamide) | BENZENESULFON AMIDE2IBUTYRO YLAMINO | 37 | 0 | 183 |
| (1-amino-6-methoxynaphthalene) | NAPHTHALENE1 AMINO6METHOXY | 37 | 0 | 133 |
| (N,N-dimethylsalicylamide) | SALICYLAMIDENN DIMETHYL | 37 | 0 | 133 |
| (2-(3-ethyl-3-methyltriazenyl)benzamide) | BENZAMIDE23 METHYL3ETHYL TRIAZENYL | 35 | 0 | 156 |
| (N-ethyl-indole-3-carboxamide) | INDOLE3NETHYL CARBOXAMIDO | 35 | 0 | 156 |

TABLE 41-continued
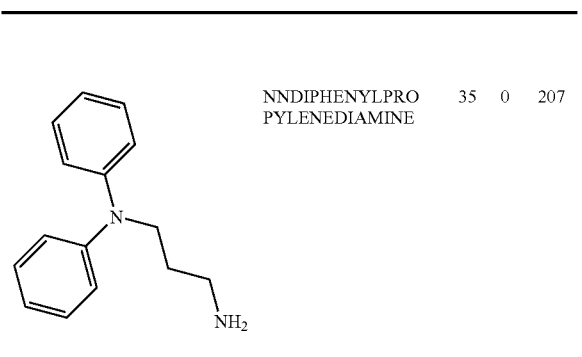
| | | | |
|---|---|---|---|
| NNDIPHENYLPROPYLENEDIAMINE | 35 | 0 | 207 |
TABLE 42
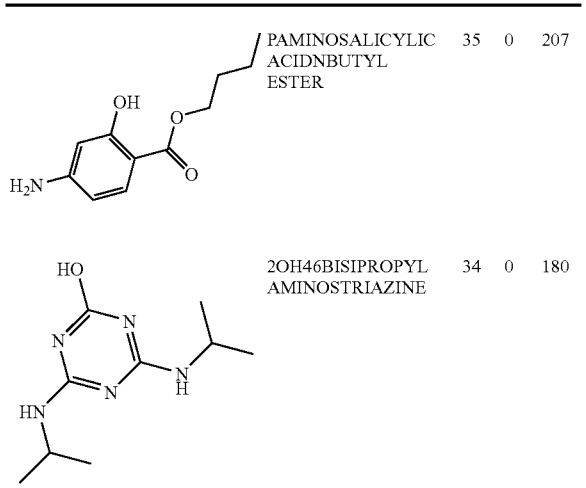
| | | | |
|---|---|---|---|
| PAMINOSALICYLICACIDNBUTYLESTER | 35 | 0 | 207 |
| 2OH46BISIPROPYLAMINOSTRIAZINE | 34 | 0 | 180 |
TABLE 42-continued
| | | | |
|---|---|---|---|
| 2PHENYLPHENOL | 34 | 0 | 130 |
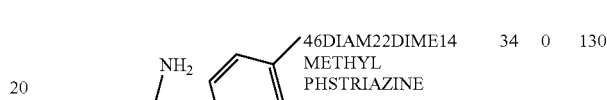
| | | | |
|---|---|---|---|
| 46DIAM22DIME14METHYLPHSTRIAZINE | 34 | 0 | 130 |
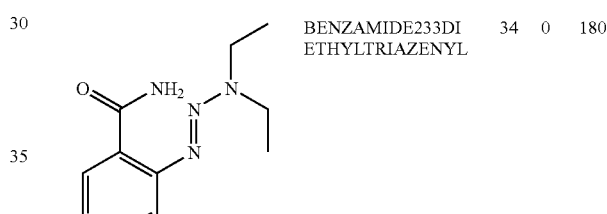
| | | | |
|---|---|---|---|
| BENZAMIDE233DIETHYLTRIAZENYL | 34 | 0 | 180 |
TABLE 43
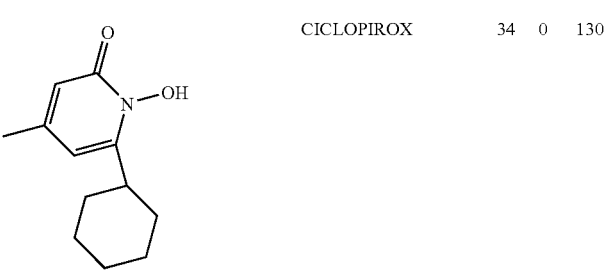
| | | | |
|---|---|---|---|
| CICLOPIROX | 34 | 0 | 130 |
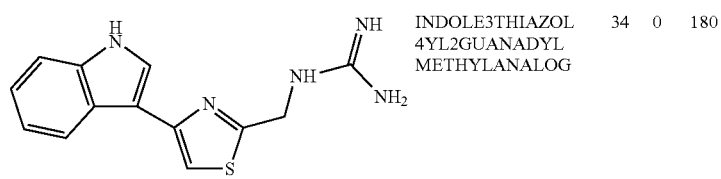
| | | | |
|---|---|---|---|
| INDOLE3THIAZOL4YL2GUANADYLMETHYLANALOG | 34 | 0 | 180 |

TABLE 43-continued
| Structure | Name | | | |
|---|---|---|---|---|
| 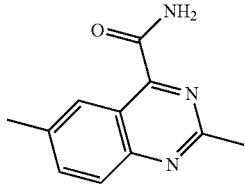 | QUINAZOLINE4 CARBAMOYL26 DIMETHYL | 34 | 0 | 130 |
| 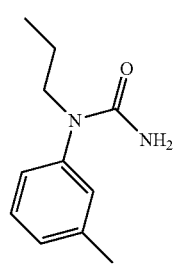 | UREA1PROPYL1M TOLYL | 34 | 0 | 180 |
| 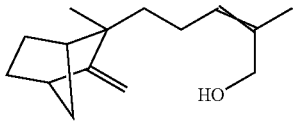 | BSANTALOL | 33 | 0 | 230 |
TABLE 44
| Structure | Name | | | |
|---|---|---|---|---|
| 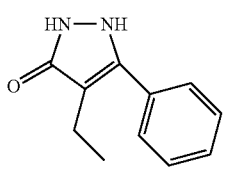 | 12DIHYDROPYRA ZOLONE4ETHYL5 PHENYL | 32 | 0 | 153 |
| 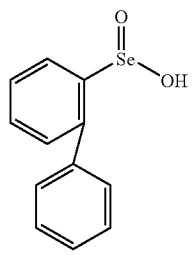 | 2BIPHENYLYL SELENIOUSACID | 32 | 0 | 153 |
| 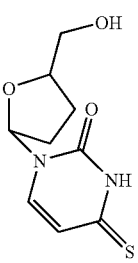 | DESETHYL ATRAZINE | 32 | 0 | 153 |
| 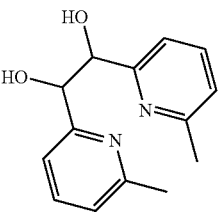 | DIDEOXY THIOURIDINE | 32 | 0 | 153 |
| 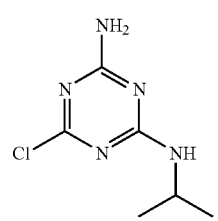 | ETHYLENEGLYCOL 12BIS6METHYL PYRID2YL | 32 | 0 | 204 |
TABLE 45
| Structure | Name | | | |
|---|---|---|---|---|
| 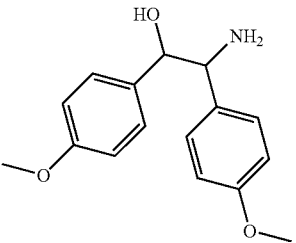 | ISOLADOL | 32 | 0 | 204 |

TABLE 46

| Name of compound | MW | LUDI_score | HB_score | LIPO_score | Rule of 5 Violations | Rotlbonds |
|---|---|---|---|---|---|---|
| 13HYDROXYPHENYL3METHOXY3METHYLUREA | 196.2054 | 32 | 0 | 153 | 0 | 5 |
| 1HYDROXYPENTACHLOROCYCLOHEXANE | 272.3857 | 28 | 0 | 124 | 0 | 1 |
| 1OHYDROXYMEPHENYL33DIMETRIAZENE | 179.2212 | 18 | 0 | 139 | 0 | 4 |
| 226DIHYDROXYPHENYLIMINOIMIDAZOLINE | 193.2048 | 16 | 0 | 112 | 0 | 3 |
| 24DIAMINO52BR45DIMEOBENZYLPYRIMIDINE | 339.1911 | 19 | 0 | 165 | 0 | 4 |
| 24DIAMINOPYRIMIDINE52CL35DIMEOBENZYL | 294.7401 | 22 | 0 | 168 | 0 | 4 |
| 26DIMETHYL1NAPHTHOL | 172.2262 | 19 | 0 | 115 | 0 | 1 |
| 2ENDOAMINOBENZOBICYCLO222OCTENE | 173.2572 | 25 | 0 | 121 | 0 | 0 |
| 2HPYRAZOLO34AQUINOLIZINE1236710BHEXAHYDRO | 177.2486 | 16 | 0 | 112 | 0 | 0 |
| 2METHOXY4MEAMINO6IPROPYLAMINOSTRIAZINE | 197.2394 | 18 | 0 | 139 | 0 | 4 |
| 2METHYL5IPROPYLPHENOL | 150.22 | 15 | 0 | 136 | 0 | 2 |
| 2OH4ETAMINO6DIETAMINOSTRIAZINE | 211.2662 | 23 | 0 | 195 | 0 | 6 |
| 2OH4IPROPYLAMINO6DIETAMINOSTRIAZINE | 225.293 | 20 | 0 | 192 | 0 | 6 |
| 2PROPYL4PTOLYLAMINO123BENZOTRIAZINIUMIODIDE | 279.3639 | 22 | 0 | 168 | 0 | 4 |
| 2PTERIDINAMINE5678TETRAHYDRO4HYDROXY67DIMETHY | 195.2236 | 16 | 0 | 112 | 0 | 1 |
| 35DIMETHOXYPHENOL | 154.1652 | 16 | 0 | 112 | 0 | 3 |
| 35DITBUTYLPHENOL | 206.3272 | 16 | 0 | 162 | 0 | 3 |
| 3AMINOBENZOICACIDETHYLESTER | 165.1914 | 21 | 0 | 142 | 0 | 3 |
| 3CYCLOHEXENOL1ISOPROPYL4METHYL | 154.2516 | 18 | 0 | 139 | 0 | 2 |
| 3HYDROXY4METHOXYCINNAMICACIDETHYLESTER | 222.2402 | 18 | 0 | 139 | 0 | 6 |
| 3OPENTYLMORPHINE | 355.476 | 16 | 0 | 213 | 0 | 6 |
| 4HYDROXYETHYLVANILLIN | 196.2024 | 31 | 0 | 177 | 0 | 6 |
| 4QUINOLINAMINE2METHYL | 158.2024 | 22 | 0 | 118 | 0 | 0 |
| 4QUINOLINAMINE6ETHOXY24PHENYLBUTADIENYL | 316.4018 | 15 | 0 | 136 | 0 | 5 |
| 5METHOXY8QUINOLINOL | 175.1866 | 28 | 0 | 124 | 0 | 2 |
| 6METHYL5INDANOL | 148.2042 | 16 | 0 | 112 | 0 | 1 |
| 8QUINOLINAMINE6METHOXY | 174.2018 | 25 | 0 | 121 | 0 | 1 |
| AAMIDOETHYLCINNAMATE | 219.2396 | 27 | 0 | 148 | 0 | 5 |
| AAMIDOMETHYLCINNAMATE | 205.2128 | 28 | 0 | 124 | 0 | 4 |
| ANILINE35DIMETHOXY | 153.1804 | 22 | 0 | 118 | 0 | 2 |
| ANILINE35DITBUTYL | 205.3424 | 19 | 0 | 165 | 0 | 2 |
| ANTHRALIN102HYDROXYETHIO | 302.3442 | 17 | 0 | 189 | 0 | 6 |

TABLE 47

| Name of compound | MW | LUDI_score | HB_score | LIPO_score | Rule of 5 Violations | Rotlbonds |
|---|---|---|---|---|---|---|
| ATROMEPINE | 303.4004 | 22 | 0 | 219 | 0 | 6 |
| BENZAMIDENHEXYL34DIHYDROXY | 237.298 | 29 | 0 | 251 | 0 | 9 |
| BENZAMIDEOISOPROPYLAMINO | 178.2334 | 15 | 0 | 136 | 0 | 3 |
| BENZENEMETHANIMINE25DIMETHYLAPHENYL | 209.2902 | 16 | 0 | 112 | 0 | 2 |
| BENZENESULFONAMIDE22ETHYLBUTANOYLAMINO | 270.3458 | 22 | 0 | 219 | 0 | 6 |
| BENZOICACID2AMINOMETHYLESTER | 151.1646 | 19 | 0 | 115 | 0 | 2 |
| BENZOICACIDHYDRAZIDEO33DIMETRIAZINO | 207.2346 | 40 | 0 | 136 | 0 | 4 |
| BENZOIN | 212.2476 | 16 | 0 | 162 | 0 | 4 |
| BENZOINOXIME | 227.2622 | 28 | 0 | 174 | 0 | 5 |
| BENZYLALCOHOL35DIMETHOXY4HYDROXY | 184.1914 | 21 | 0 | 142 | 0 | 5 |
| CARVEOL | 152.2358 | 18 | 0 | 139 | 0 | 2 |
| CINAMETICACID | 238.2396 | 16 | 0 | 162 | 0 | 8 |
| CYPENAMINE | 161.2462 | 25 | 0 | 121 | 0 | 1 |
| CYTIDINE23DIDEHYDRO23DIDEOXY | 209.2042 | 15 | 0 | 136 | 0 | 3 |
| CYTIDINEDIDEOXY3FLUORO | 229.2105 | 18 | 0 | 139 | 0 | 3 |
| CYTOSINE2BUTOXY | 167.2102 | 17 | 0 | 189 | 0 | 4 |
| DMDC | 239.2304 | 27 | 0 | 148 | 0 | 4 |
| ECGONINEMETHYLESTER | 199.2492 | 27 | 0 | 148 | 0 | 3 |
| ETHYCHLOZATE | 238.6731 | 20 | 0 | 192 | 0 | 4 |
| ETHYLENEGLYCOLMONO24DICHLOROPHENYLETHER | 207.056 | 25 | 0 | 171 | 0 | 4 |
| ETHYLMETHYLGLYOXIME | 130.1462 | 27 | 83 | 65 | 0 | 4 |
| F11105 | 203.2432 | 15 | 0 | 136 | 0 | 2 |
| FLOVERINE | 198.2182 | 22 | 0 | 168 | 0 | 6 |
| GUANIDINE1METHYL14CHLOROPHENYL | 183.6401 | 19 | 0 | 115 | 0 | 2 |
| GUANIDINEN43AMINOPHENYLTHIAZOL2YL | 233.2904 | 22 | 0 | 118 | 1 | 2 |
| HEXAHYDROFLUOREN9AAMINE | 187.284 | 28 | 0 | 124 | 0 | 0 |
| ILEPRO | 228.2906 | 16 | 83 | 130 | 0 | 6 |
| IMIDAZOLINE22HYDROXYPHENYL | 162.1908 | 19 | 0 | 115 | 0 | 2 |
| INDOLE3CARBOXYLICACIDETHYLESTER | 189.2134 | 18 | 0 | 139 | 0 | 3 |
| INDOLE3IMIDAZOL1YLMETHYL | 197.239 | 16 | 0 | 162 | 0 | 2 |
| INDOLE3NMETHYLCARBOXAMIDO | 174.2018 | 28 | 0 | 124 | 0 | 2 |
| LAMIVUDINE | 229.2532 | 18 | 0 | 139 | 0 | 3 |
| METHYLBENZOATE2AMINO5CHLORO | 185.6097 | 16 | 0 | 112 | 0 | 2 |
| METHYLSALICYLATE | 152.1494 | 16 | 0 | 112 | 0 | 3 |

TABLE 48

| | | | | | | |
|---|---|---|---|---|---|---|
| MORPHINE3HEXANOYL | 383.4864 | 25 | 0 | 222 | 0 | 7 |
| MPENTOXYPHENOL | 180.2462 | 16 | 0 | 213 | 0 | 6 |
| N1PCHLOROPHENYLN5METHYLBIGUANIDE | 225.6803 | 43 | 0 | 139 | 0 | 5 |
| N2N4N6TRIMETHYLNNNHYDROXYMETHYLMELAMINE | 258.2796 | 17 | 3 | 186 | 0 | 9 |
| NAPHTHALENE1AMINO3CHLORO | 177.6329 | 25 | 0 | 121 | 0 | 0 |
| NAPHTHALENE1AMINO3METHYL | 157.2146 | 25 | 0 | 121 | 0 | 0 |
| NAPHTHALENE1AMINO6CHLORO | 177.6329 | 28 | 0 | 124 | 0 | 0 |
| NBUTYLSALICYLIDENEIMINE | 177.2456 | 20 | 0 | 192 | 0 | 5 |
| NCYCLOPENTYLCINNAMAMIDE | 215.2944 | 27 | 0 | 148 | 0 | 4 |
| NETHYLMORPHINE | 299.3688 | 136 | 0 | 257 | 0 | 3 |
| NHYDROXYETHYLPTP | 203.2834 | 31 | 0 | 177 | 0 | 4 |
| NITRAFUDAM | 231.2104 | 25 | 0 | 121 | 0 | 2 |
| NNDIMETHYLTRYPTAMINE6METHOXY | 218.298 | 29 | 0 | 201 | 0 | 4 |
| OMETHOXYBENZAMIDE | 151.1646 | 16 | 0 | 112 | 0 | 2 |
| OMETHYLCINNAMAMIDE | 161.203 | 22 | 0 | 118 | 0 | 2 |
| OMETHYLTYROSINEETHYLESTER | 223.2712 | 30 | 0 | 227 | 0 | 6 |
| PAMINOSALICYLICACID4CHLOROBUTYLESTER | 243.6895 | 22 | 0 | 219 | 0 | 7 |
| PAMINOSALICYLICACIDNAMYLESTER | 223.2712 | 25 | 0 | 222 | 0 | 7 |
| PENTA24DIENYLAMINE23455PENTACHLORO | 255.3583 | 18 | 0 | 139 | 0 | 2 |
| PENTALAMIDE | 207.2718 | 19 | 0 | 216 | 0 | 6 |
| PHENOL2HEPTYL | 192.3004 | 21 | 0 | 142 | 0 | 7 |
| PHENYLBORONICACIDMETHOXYACETAMIDO | 209.0081 | 19 | 0 | 165 | 0 | 7 |
| PICOLINHYDROXAMICACID | 166.1792 | 19 | 0 | 115 | 0 | 3 |
| PROTOCATECHUICACIDETHYLESTER | 182.1756 | 15 | 0 | 136 | 0 | 5 |
| PYRAZINE2AMIDINO56DIMETHYL3METHYLAMINO | 179.2242 | 25 | 0 | 121 | 0 | 2 |
| PYRAZOLE23DIHYDRO3IMINO15DIMETHYL2PHENYL | 187.2438 | 25 | 0 | 121 | 0 | 1 |
| PYRAZOLE24DIMETHYL5PHENYL | 172.2292 | 16 | 0 | 112 | 0 | 1 |
| PYRAZOLE426DIMETHYLPHENYLMETHYL | 186.256 | 16 | 0 | 162 | 0 | 2 |
| PYRAZOLE4METHYL5PHENYL | 158.2024 | 16 | 0 | 112 | 0 | 1 |
| PYRIDINE22HYDROXYPHENYL | 171.1982 | 25 | 0 | 121 | 0 | 2 |
| PYRIDINE4HYDROXY26BISMETHOXYCARBONYL | 211.1738 | 22 | 0 | 118 | 0 | 5 |
| PYRIMIDINE24DIAMIO6METHYL5PHENYL | 200.2426 | 22 | 0 | 118 | 0 | 1 |
| PYRIMIDINE2AMINO4DIETHYLAMINOETHYLAMINO56DIMETHYL | 237.3472 | 26 | 0 | 248 | 0 | 6 |

TABLE 49

| | | | | | | |
|---|---|---|---|---|---|---|
| PYRIMIDINE2DIMETHYLAMINO4METHYLAMINO | 152.1986 | 19 | 0 | 115 | 0 | 2 |
| PYRIMIDINE2HYDRAZINO4METHOXY6METHYL | 154.1712 | 19 | 0 | 115 | 0 | 2 |
| PYRIMIDINE4AMINO2DIMETHYLAMINO | 138.1718 | 28 | 0 | 124 | 0 | 1 |
| QUINOLINE4AMINO7CHLORO | 178.6207 | 22 | 0 | 118 | 0 | 0 |
| RA161045 | 371.484 | 19 | 0 | 216 | 0 | 5 |
| SYMTRIAZINE2ETHYLAMINO4TBUTYLAMINO6HYDROXY | 211.2662 | 22 | 0 | 168 | 0 | 5 |
| TERPENE319712 | 268.3954 | 25 | 0 | 171 | 0 | 4 |
| TETRAHYDROPYRAN24DIONE31ETHOXYIMINOBUTYL66SPIRO35DIMETHYLCYCLOHEXYL | 323.4314 | 23 | 0 | 195 | 0 | 6 |
| TIMIRDINE | 227.7111 | 16 | 0 | 112 | 0 | 1 |
| TIZOLEMIDE | 335.8229 | 27 | 0 | 148 | 0 | 3 |
| UREA1BUTYL1PTOLYL | 206.287 | 17 | 0 | 189 | 0 | 5 |
| UREA1ETHYL1MTOLYL | 178.2334 | 29 | 0 | 150 | 0 | 3 |
| UREA1ETHYL1OANISYL | 194.2328 | 29 | 0 | 150 | 0 | 4 |
| UREA1ETHYL1OETHOXYPHENYL | 208.2596 | 31 | 0 | 177 | 0 | 5 |
| UREA1METHYL1MTOLYL | 164.2066 | 22 | 0 | 118 | 0 | 2 |
| VERBENOL | 152.2358 | 19 | 0 | 115 | 0 | 1 |
| VESTITOL | 272.3 | 22 | 0 | 118 | 0 | 4 |

EXAMPLE 6

Decrease of Activity by LBD Deletion Mutant

Figure 8:
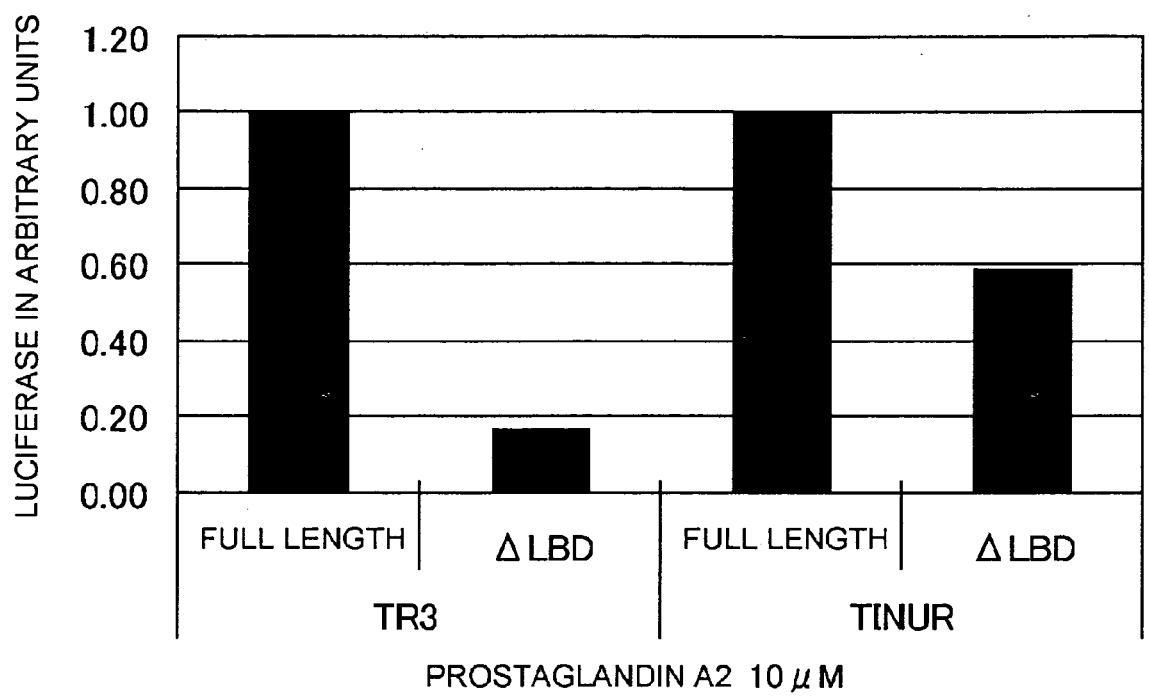
FIG. 8 shows a graph demonstrating the decrease of prostaglandin $A_2$ transcriptional activity by the LBD deletion mutant. ΔLBD denotes the deletion mutant.

Prostaglandin $A_2$ transcriptional activity was suppressed in a Mammalian Two Hybrid reporter system that used a TR3 or TINUR gene completely lacking an LBD region (FIG. 8). Thus, it was implied that prostaglandin $A_2$ functions by acting on the LBD region of the nuclear receptor.

EXAMPLE 7

Demonstration of the Binding of PGA Derivatives to TR3 or TINUR Using BIAcor

Figure 9:
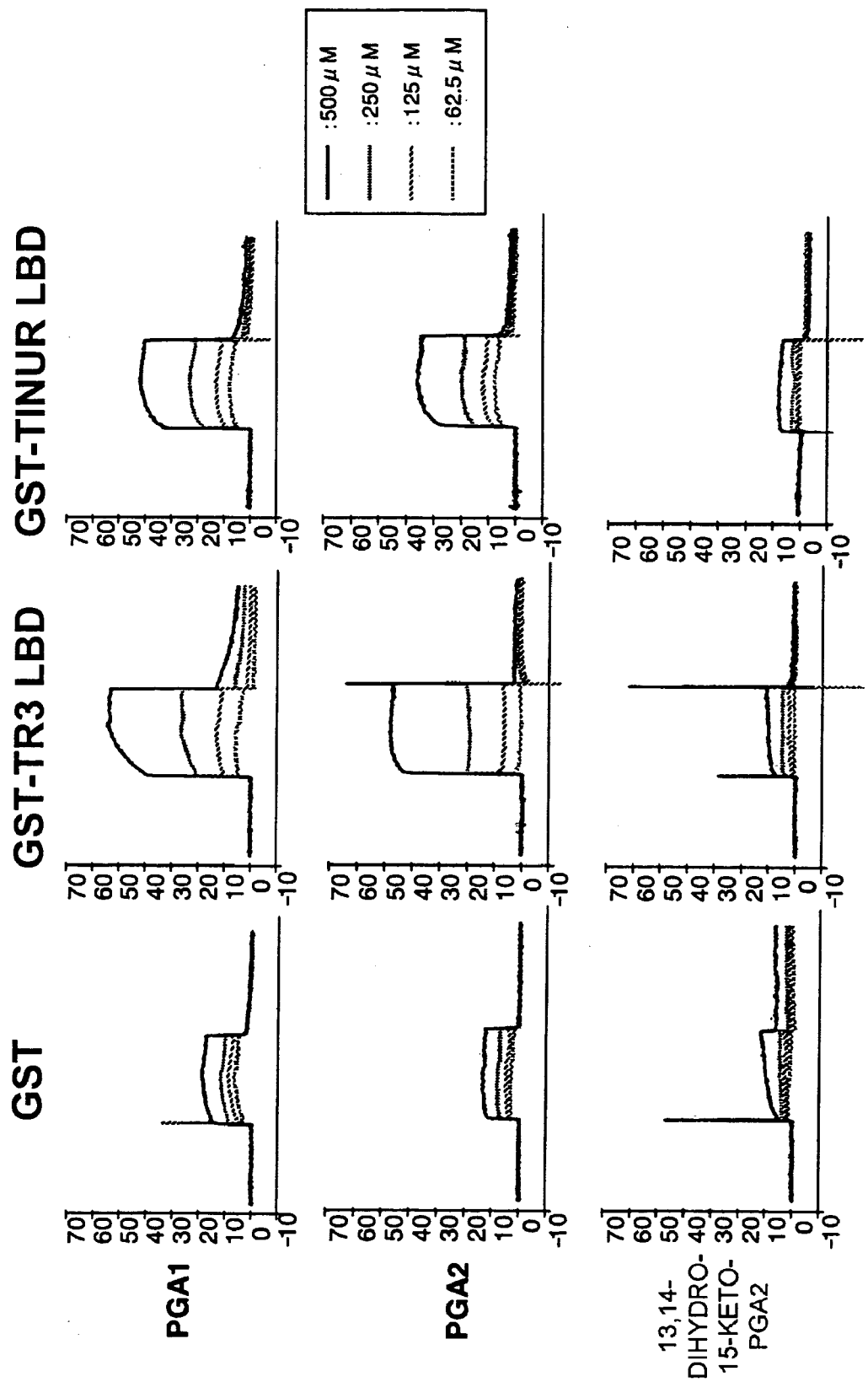
FIG. 9 shows diagrams showing PGA1 and PGA2 bound to TR3 LBD or TINUR LBD, revealed using BIAcor S51. Glutathione S-transferase (GST) was used as a comparison control, and 13,14-Dihydro-15-keto-PGA2 was used as a negative control.

To conclusively demonstrate PGA derivative ligand binding activity to TR3 or TINUR, revealed using the Mammalian Two Hybrid reporter system, TR3 GST-LBD and TINUR GST-LBD were respectively expressed in E. coli, and then purified. PGA1 and PGA2 binding to the LBD of TR3 or TINUR was detected by BIAcor S51, using comparison with GST as a base (FIG. 9). The negative control compound, 13,14-dihydro-15-keto-PGA2, did not demonstrate any activity in the reporter system, and did not bind to the LBD.

EXAMPLE 8

Genes such as TR3 or TINUR, which comprise apoptotic character, may be enhanced in the peripheral blood eosinophils of atopic dermatitis conditions due to negative feedback regulation that acts to reduce the increase in peripheral blood eosinophils that occurs in association with a pathologic condition. Therefore, the present inventers investigated in vitro the type of stimulation that causes expression of this kind of gene in eosinophils.

Figure 10:
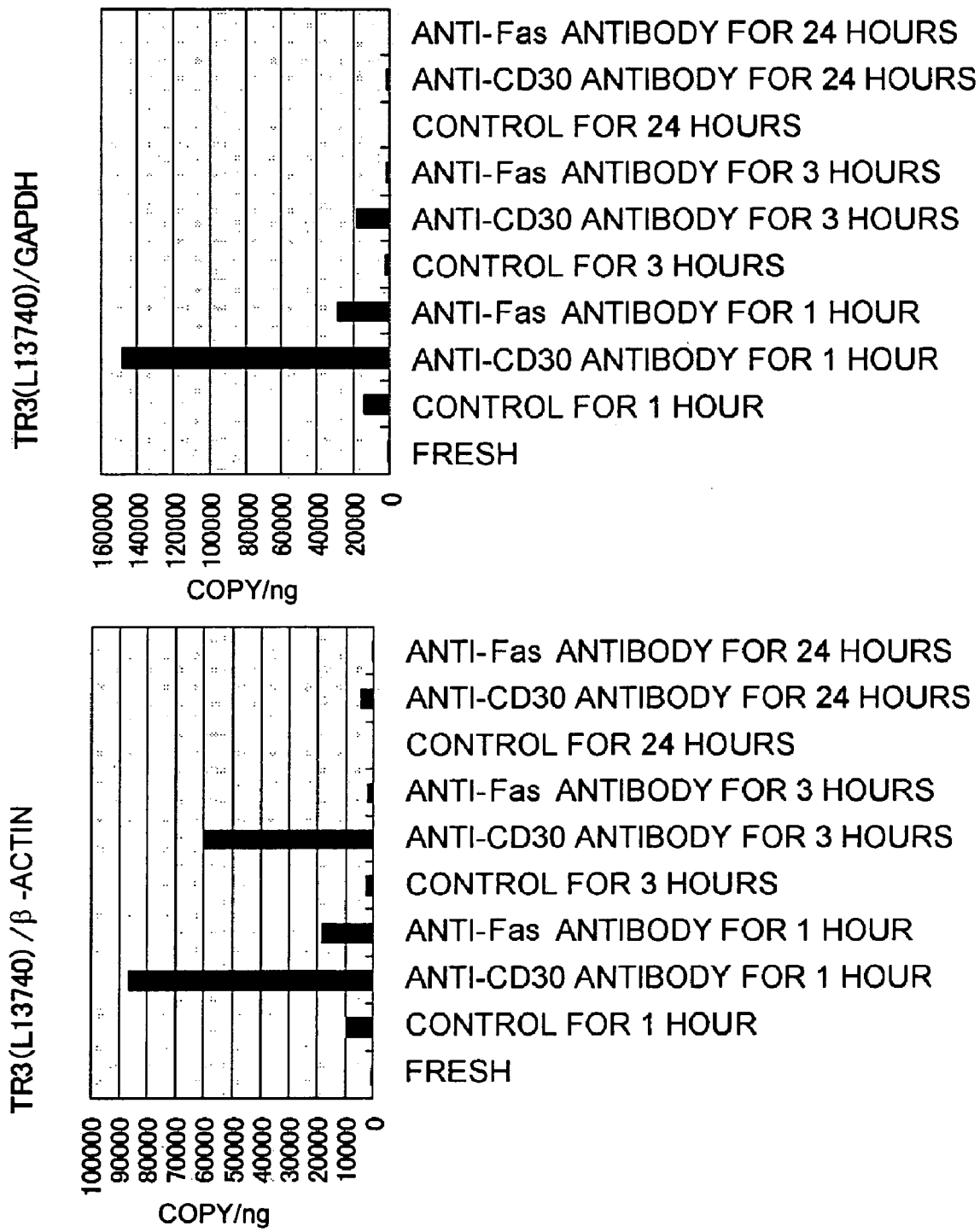
FIG. 10 shows graphs demonstrating the results of TR3 expression induction in apoptotic stimulation of peripheral blood eosinophils using an anti-CD30 or anti-Fas antibody. Beta-actin-corrected values and GAPDH-corrected values are shown.
Figure 11:
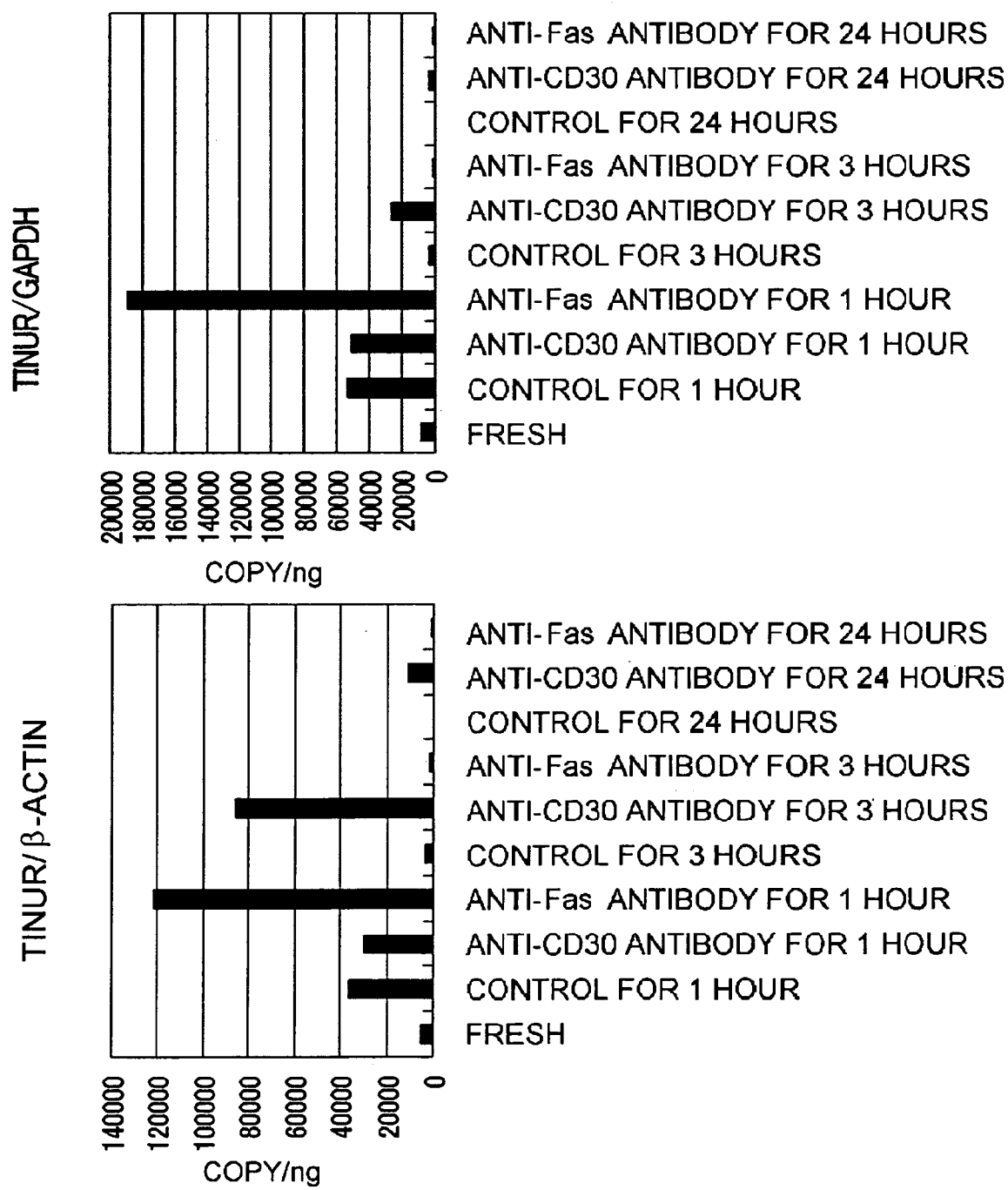
FIG. 11 shows graphs demonstrating the results of TINUR expression induction in apoptotic stimulation of peripheral blood eosinophils using anti-CD30 or anti-Fas antibody. Beta-actin-corrected values and GAPDH-corrected values are shown.

A large number of peripheral blood eosinophils were collected from healthy subjects and cultured, while suppressing their activation, in suspension in petri dishes. Eosinophil activation by stimulation with cytokines such as IL-5 and IL-4 did not lead to TR3 induction. In contrast, induction of cell apoptosis using anti-CD30 antibody resulted in dramatic induction of TR3 and TINUR in cultured peripheral blood eosinophils over a one to three-hour treatment (Table 50, FIGS. 10 and 11). This anti-CD30 antibody comprises agonist activity towards eosinophil CD30, and has recently received attention due to possible use as a therapeutic agent for asthma or the like, by inducing apoptosis in eosinophils by a specific intracellular pathway. Table 50 below summarizes the apoptosis induction of human peripheral blood eosinophils.

TABLE 50

|  |  | Annexin V-positive cells (%) |
|---|---|---|
| Fresh |  | 4.0 |
| Control | 1 hr | 2.30 |
| Anti-CD30 antibody |  | 9.20 |
| Anti-Fas antibody |  | 5.20 |
| Control | 3 hr | 4.50 |
| Anti-CD30 antibody |  | 20.00 |
| Anti-Fas antibody |  | 13.80 |

TABLE 50-continued

|  |  | Annexin V-positive cells (%) |
|---|---|---|
| Control | 24 hr | 11.70 |
| Anti-CD30 antibody |  | 63.00 |
| Anti-Fas antibody |  | 31.20 |

Figure 12:
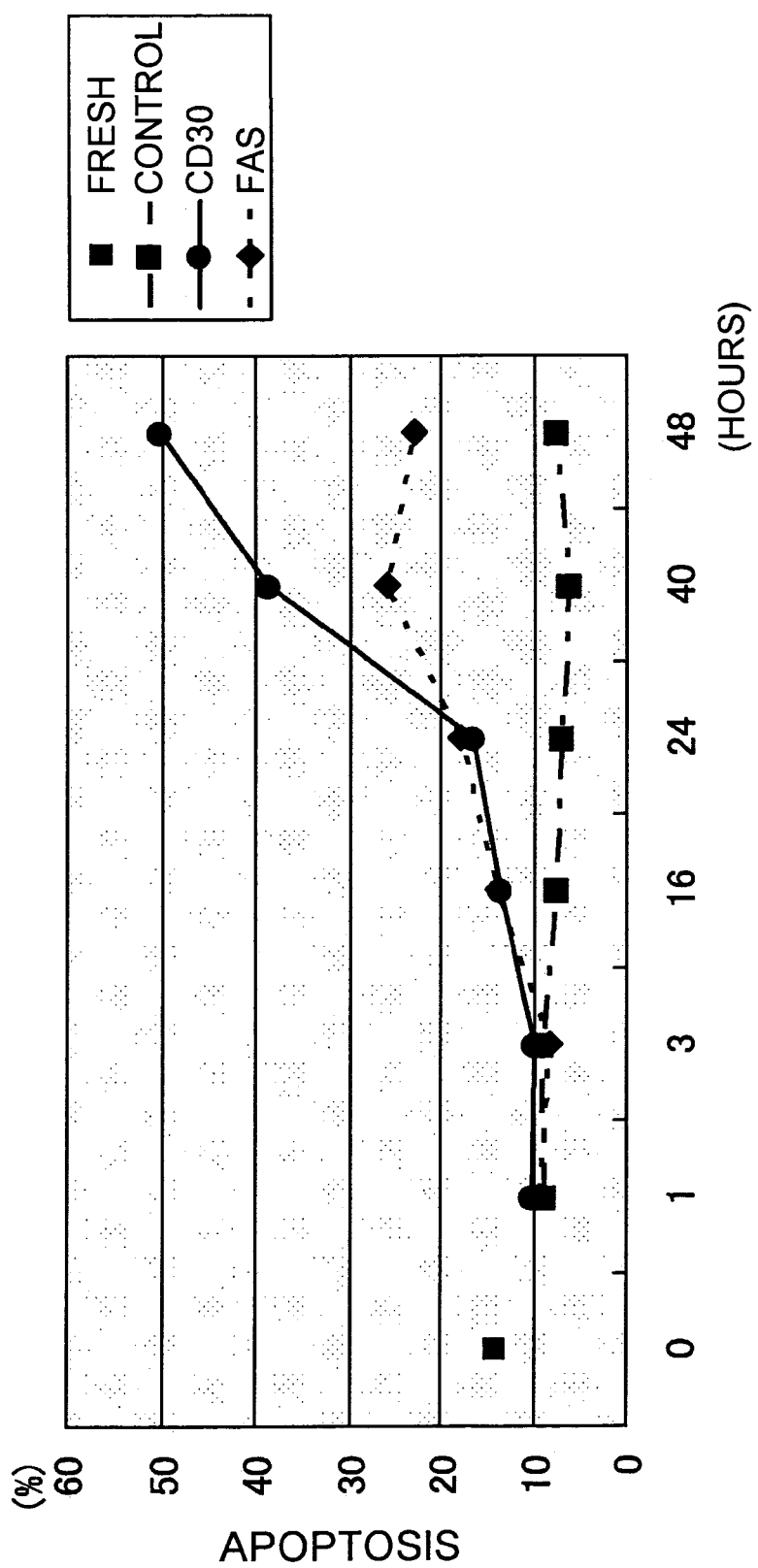
FIG. 12 is a graph indicating apoptosis induction after treating the eosinophil-specific cell line, AML14.3D10, with anti-CD30 antibody or anti-Fas antibody.
Figure 13:
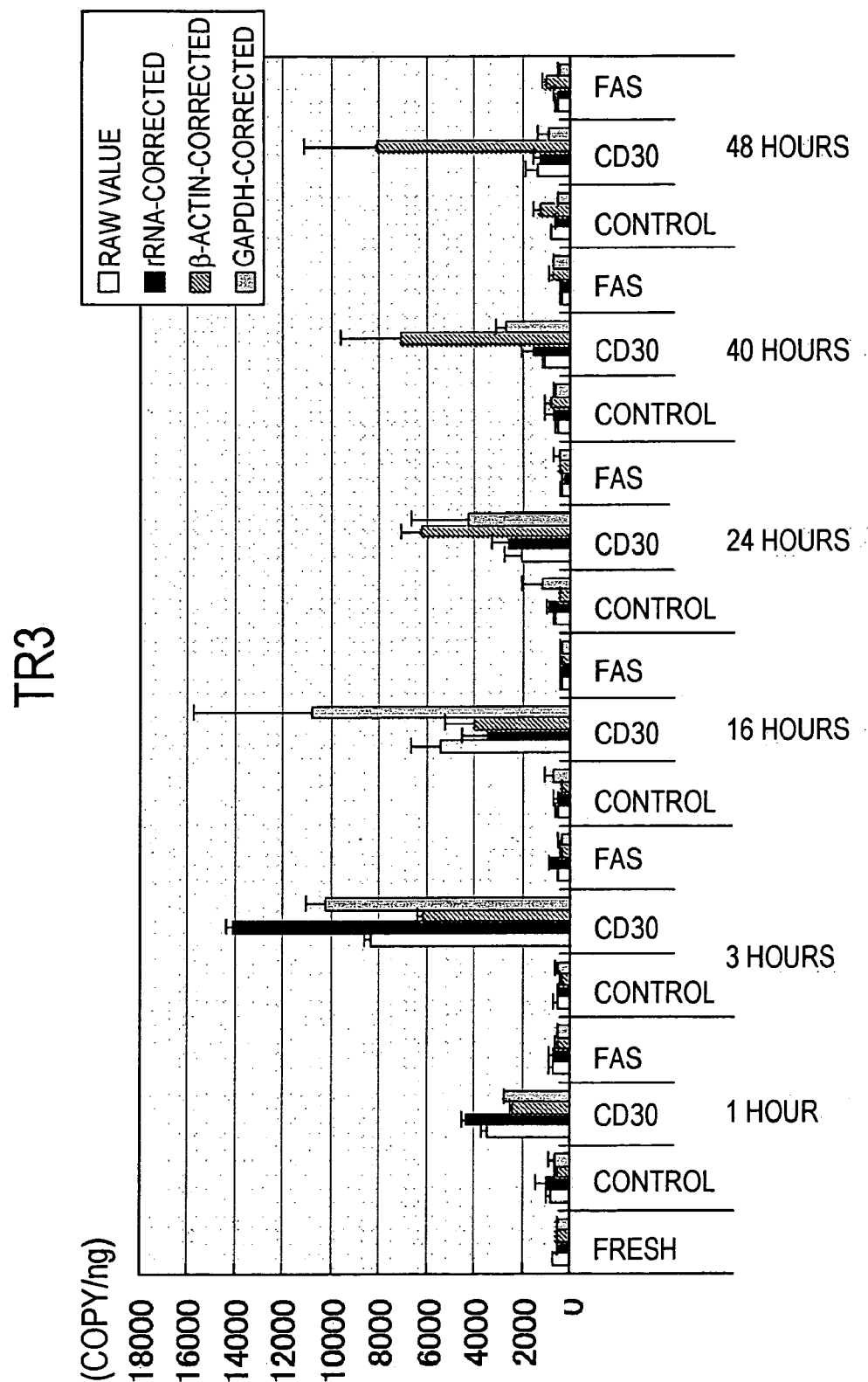
FIG. 13 is a graph indicating TR3 expression induction after treating the eosinophil-specific cell line, AML14.3D10, with anti-CD30 antibody or anti-Fas antibody.
Figure 14:
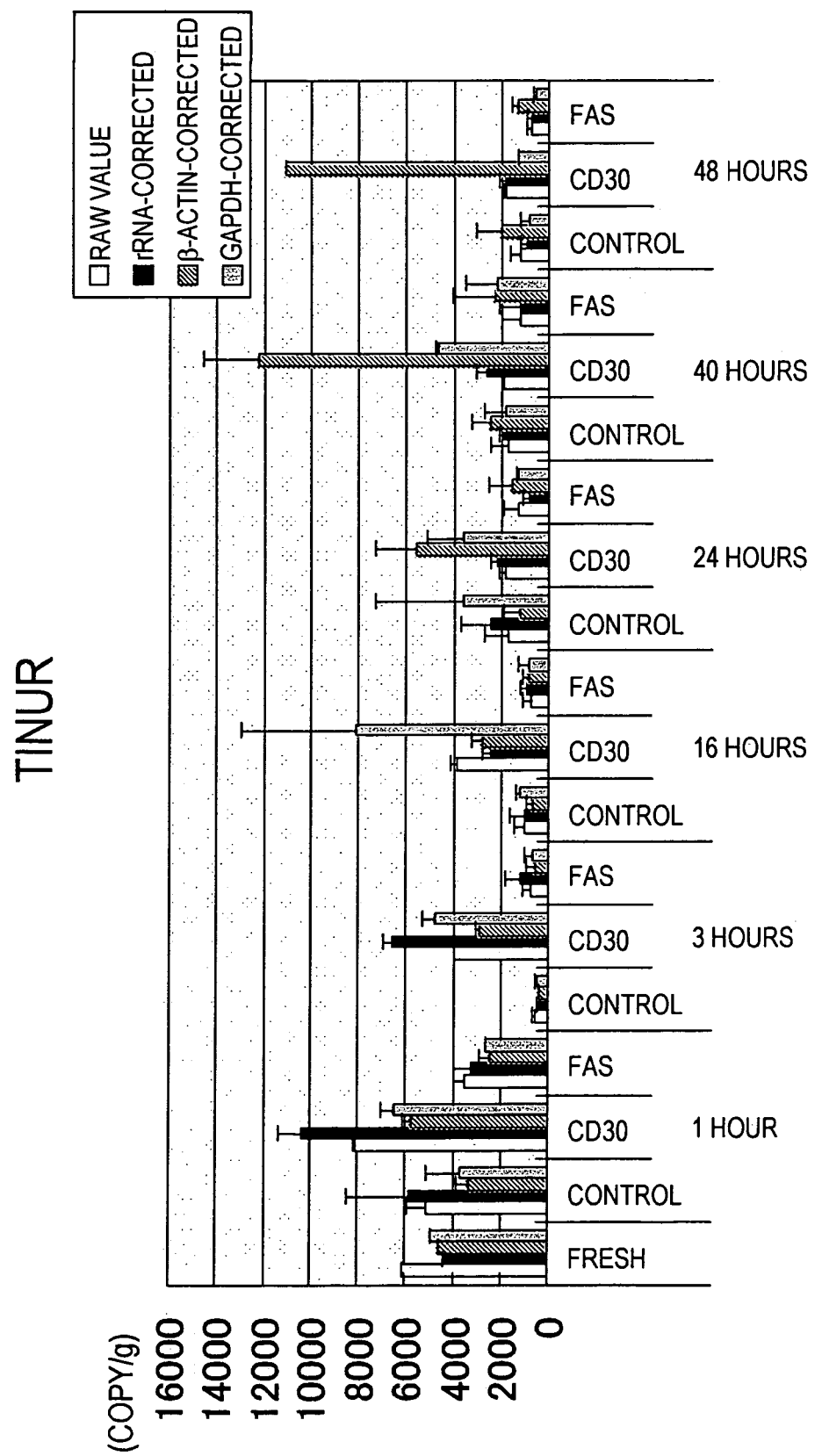
FIG. 14 shows a graph indicating TINUR expression induction after treating the eosinophil-specific cell line, AML14.3D10, with anti-CD30 antibody or anti-Fas antibody.

Although the anti-Fas antibody induced apoptosis, albeit more slowly than the anti-CD30 antibody, it did not induce TR3 and TINUR. Thus, apoptosis induction by the anti-CD30 antibody, accompanied by TR3 and TINUR induction, may occur through an eosinophil-specific apoptosis pathway that is different from conventional pathways. These phenomena (apoptosis induction and expression induction of TR3 or TINUR) were similarly observed when AML14.3D10, an eosinophil-specific cell line, was treated with anti-CD30 antibody (FIGS. 12, 13 and 14).

Figure 15:
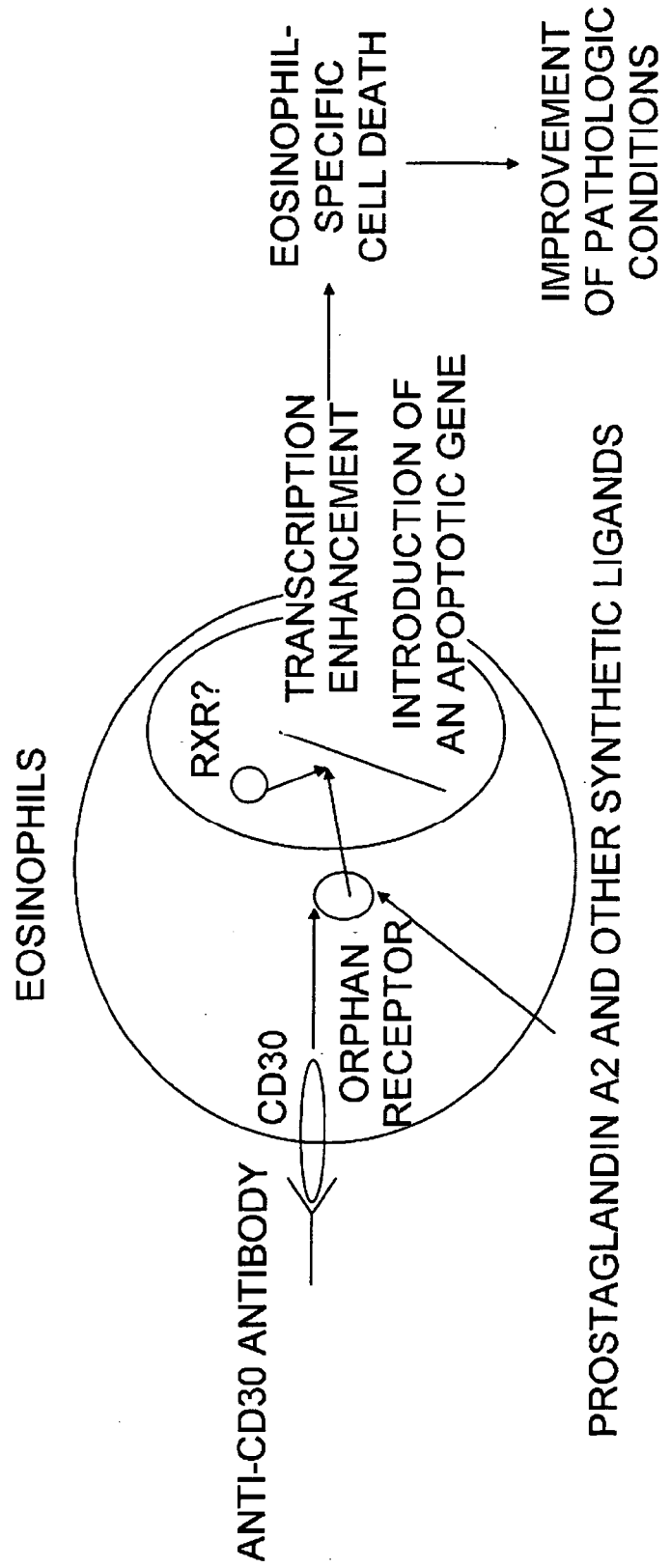
FIG. 15 shows a working hypothesis for allergic disease treatment via eosinophil cell death, caused by a member of the nuclear receptor Nur subfamily, including TR3 and TINUR.

It is very likely that promotion of a pathway that specifically leads eosinophils to cell death through the enhancement of TR3 or TINUR function will lead to the treatment of not only asthma, but also of various allergic diseases including atopic dermatitis, which was investigated by the present inventors. An example of the therapeutic strategy intended by the present inventors is shown in FIG. 15.

What is claimed is:

1. A method of testing for atopic dermatitis in a test subject, said method comprising the steps of:
   a) obtaining a sample from the test subject, said sample containing eosinophil cells;
   b) measuring the expression level of a gene or genes encoding the TR3, TINUR or TR3 and TINUR receptor protein, in the eosinophil cells; and
   c) determining whether the expression level of the gene or genes in the eosinophil cells is elevated compared to the expression level of the gene or genes in eosinophil cells of normal subjects,
   wherein a determination that the expression level of the gene or genes in the eosinophil cells is elevated indicates that the test subject has atopic dermatitis.

2. The testing method of claim 1, wherein the gene expression level is measured by cDNA PCR.

* * * * *

SEQUENCE LISTING

```
<160> NUMBER OF SEQ ID NOS: 14

<210> SEQ ID NO 1
<211> LENGTH: 2464
<212> TYPE: DNA
<213> ORGANISM: Homo sapiens
<220> FEATURE:
<221> NAME/KEY: CDS
<222> LOCATION: (111)..(1904)

<400> SEQUENCE: 1
cggaaacttg ggggagtgca cagaagaact tcgggagcgc acgcgggacc agggaccagg      60
ctgagactcg gggcgccagt ccgggcaggg gcagcgggac gcggccggag atg ccc       116
                                                      Met Pro
                                                        1 tgt atc caa gcc caa tat ggg aca cca gca ccg agt ccg gga ccc cgt      164
Cys Ile Gln Ala Gln Tyr Gly Thr Pro Ala Pro Ser Pro Gly Pro Arg
          5                  10                  15 gac cac ctg gca agc gac ccc ctg acc cct gag ttc atc aag ccc acc      212
Asp His Leu Ala Ser Asp Pro Leu Thr Pro Glu Phe Ile Lys Pro Thr
     20                  25                  30 atg gac ctg gcc agc ccc gag gca gcc ccc gct gcc ccc act gcc ctg      260
Met Asp Leu Ala Ser Pro Glu Ala Ala Pro Ala Ala Pro Thr Ala Leu
 35                  40                  45                  50 ccc agc ttc agc acg ttc atg gac ggc tac aca gga gag ttt gac acc      308
Pro Ser Phe Ser Thr Phe Met Asp Gly Tyr Thr Gly Glu Phe Asp Thr
                 55                  60                  65 ttc ctc tac cag ctg cca gga aca gtc cag cca tgc tca tca gcc tcc      356
Phe Leu Tyr Gln Leu Pro Gly Thr Val Gln Pro Cys Ser Ser Ala Ser
             70                  75                  80 tcc tcg gcc tcc tcc aca tcc tcg tcc tca gcc acc tcc cct gcc tct      404
```

```
                Ser Ser Ala Ser Ser Thr Ser Ser Ser Ala Thr Ser Pro Ala Ser
                        85                  90                  95 gcc tcc ttc aag ttc gag gac ttc cag gtg tac ggc tgc tac ccc ggc              452
Ala Ser Phe Lys Phe Glu Asp Phe Gln Val Tyr Gly Cys Tyr Pro Gly
        100                 105                 110 ccc ctg agc ggc cca gtg gat gag gcc ctg tcc tcc agt ggc tct gac              500
Pro Leu Ser Gly Pro Val Asp Glu Ala Leu Ser Ser Ser Gly Ser Asp
115                 120                 125                 130 tac tat ggc agc ccc tgc tcg gcc ccg tcg ccc tcc acg ccc agc ttc              548
Tyr Tyr Gly Ser Pro Cys Ser Ala Pro Ser Pro Ser Thr Pro Ser Phe
                135                 140                 145 cag ccg ccc cag ctc tct ccc tgg gat ggc tcc ttc ggc cac ttc tcg              596
Gln Pro Pro Gln Leu Ser Pro Trp Asp Gly Ser Phe Gly His Phe Ser
        150                 155                 160 ccc agc cag act tac gaa ggc ctg cgg gca tgg aca gag cag ctg ccc              644
Pro Ser Gln Thr Tyr Glu Gly Leu Arg Ala Trp Thr Glu Gln Leu Pro
        165                 170                 175 aaa gcc tct ggg ccc cca cag cct cca gcc ttc ttt tcc ttc agt cct              692
Lys Ala Ser Gly Pro Pro Gln Pro Pro Ala Phe Phe Ser Phe Ser Pro
180                 185                 190 ccc act ggc ccc agc ccc agc ctg gcc cag agc ccc ctg aag ttg ttc              740
Pro Thr Gly Pro Ser Pro Ser Leu Ala Gln Ser Pro Leu Lys Leu Phe
195                 200                 205                 210 ccc tca cag gcc acc cac cag ctg ggg gag gga gag agc tat tcc atg              788
Pro Ser Gln Ala Thr His Gln Leu Gly Glu Gly Glu Ser Tyr Ser Met
                215                 220                 225 cct acg gcc ttc cca ggt ttg gca ccc act tct cca cac ctt gag ggc              836
Pro Thr Ala Phe Pro Gly Leu Ala Pro Thr Ser Pro His Leu Glu Gly
        230                 235                 240 tcg ggg ata ctg gat aca ccc gtg acc tca acc aag gcc cgg agc ggg              884
Ser Gly Ile Leu Asp Thr Pro Val Thr Ser Thr Lys Ala Arg Ser Gly
        245                 250                 255 gcc cca ggt cca agt gaa ggc cgc tgt gct gtg tgt ggg gac aac gct              932
Ala Pro Gly Pro Ser Glu Gly Arg Cys Ala Val Cys Gly Asp Asn Ala
260                 265                 270 tca tgc cag cat tat ggt gtc cgc aca tgt gag ggc tgc aag ggc ttc              980
Ser Cys Gln His Tyr Gly Val Arg Thr Cys Glu Gly Cys Lys Gly Phe
275                 280                 285                 290 ttc aag cgc aca gtg cag aaa aac gcc aag tac atc tgc ctg gct aac             1028
Phe Lys Arg Thr Val Gln Lys Asn Ala Lys Tyr Ile Cys Leu Ala Asn
                295                 300                 305 aag gac tgc cct gtg gac aag agg cgg cga aac cgc tgc cag ttc tgc             1076
Lys Asp Cys Pro Val Asp Lys Arg Arg Arg Asn Arg Cys Gln Phe Cys
        310                 315                 320 cgc ttc cag aag tgc ctg gcg gtg ggc atg gtg aag gaa gtt gtc cga             1124
Arg Phe Gln Lys Cys Leu Ala Val Gly Met Val Lys Glu Val Val Arg
        325                 330                 335 aca gac agc ctg aag ggg cgg cgg ggc cgg cta cct tca aaa ccc aag             1172
Thr Asp Ser Leu Lys Gly Arg Arg Gly Arg Leu Pro Ser Lys Pro Lys
        340                 345                 350 cag ccc cca gat gcc tcc cct gcc aat ctc ctc act tcc ctg gtc ctt             1220
Gln Pro Pro Asp Ala Ser Pro Ala Asn Leu Leu Thr Ser Leu Val Leu
355                 360                 365                 370 gca cac ctg gat tca ggg ccc agc act gcc aaa ctg gac tac tcc aag             1268
Ala His Leu Asp Ser Gly Pro Ser Thr Ala Lys Leu Asp Tyr Ser Lys
                375                 380                 385 ttc cag gag ctg gtg ctg ccc cac ttt ggg aag gaa gat gct ggg gat             1316
Phe Gln Glu Leu Val Leu Pro His Phe Gly Lys Glu Asp Ala Gly Asp
        390                 395                 400
```

| | | | | | | | | | | | | | | | |
|---|---|---|---|---|---|---|---|---|---|---|---|---|---|---|---|
| gta | cag | cag | ttc | tac | gac | ctg | ctc | tcc | ggt | tct | ctg | gag | gtc | atc | cga | 1364 |
| Val | Gln | Gln | Phe | Tyr | Asp | Leu | Leu | Ser | Gly | Ser | Leu | Glu | Val | Ile | Arg | |
| | 405 | | | | | 410 | | | | | 415 | | | | | | aag tgg gcg gag aag atc cct ggc ttt gct gag ctg tca ccg gct gac 1412
Lys Trp Ala Glu Lys Ile Pro Gly Phe Ala Glu Leu Ser Pro Ala Asp
420                      425                      430 cag gac ctg ttg ctg gag tcg gcc ttc ctg gag ctc ttc atc ctc cgc 1460
Gln Asp Leu Leu Leu Glu Ser Ala Phe Leu Glu Leu Phe Ile Leu Arg
435                  440                      445                      450 ctg gcg tac agg tct aag cca ggc gag ggc aag ctc atc ttc tgc tca 1508
Leu Ala Tyr Arg Ser Lys Pro Gly Glu Gly Lys Leu Ile Phe Cys Ser
                 455                      460                      465 ggc ctg gtg cta cac cgg ctg cag tgt gcc cgt ggc ttc ggg gac tgg 1556
Gly Leu Val Leu His Arg Leu Gln Cys Ala Arg Gly Phe Gly Asp Trp
             470                      475                      480 att gac agt atc ctg gcc ttc tca agg tcc ctg cac agc ttg ctt gtc 1604
Ile Asp Ser Ile Leu Ala Phe Ser Arg Ser Leu His Ser Leu Leu Val
         485                      490                      495 gat gtc cct gcc ttc gcc tgc ctc tct gcc ctt gtc ctc atc acc gac 1652
Asp Val Pro Ala Phe Ala Cys Leu Ser Ala Leu Val Leu Ile Thr Asp
     500                      505                      510 cgg cat ggg ctg cag gag ccg cgg cgg gtg gag gag ctg cag aac cgc 1700
Arg His Gly Leu Gln Glu Pro Arg Arg Val Glu Glu Leu Gln Asn Arg
515                      520                      525                      530 atc gcc agc tgc ctg aag gag cac gtg gca gct gtg gcg ggc gag ccc 1748
Ile Ala Ser Cys Leu Lys Glu His Val Ala Ala Val Ala Gly Glu Pro
                 535                      540                      545 cag cca gcc agc tgc ctg tca cgt ctg ttg ggc aaa ctg ccc gag ctg 1796
Gln Pro Ala Ser Cys Leu Ser Arg Leu Leu Gly Lys Leu Pro Glu Leu
             550                      555                      560 cgg acc ctg tgc acc cag ggc ctg cag cgc atc ttc tac ctc aag ctg 1844
Arg Thr Leu Cys Thr Gln Gly Leu Gln Arg Ile Phe Tyr Leu Lys Leu
         565                      570                      575 gag gac ttg gtg ccc cct cca ccc atc att gac aag atc ttc atg gac 1892
Glu Asp Leu Val Pro Pro Pro Pro Ile Ile Asp Lys Ile Phe Met Asp
     580                      585                      590 acg ctg ccc ttc tgaccctgc ctgggaacac gtgtgcacat gcgcactctc         1944
Thr Leu Pro Phe
595 atatgccacc ccatgtgcct ttagtccacg gaccccagca gcaccccaa gcctgggctt   2004 gagctgcaga atgactccac cttctcacct gctccaggag gtttgcaggg agctcaagcc  2064 cttggggagg gggatgcctt catggggtg acccccacgat ttgtcttatc ccccccagcc  2124 tggcccccggc ctttatgttt tttgtaagat aaaccgtttt taacacatag cgccgtgctg 2184 taaataagcc cagtgctgct gtaaatacag gaagaaagag cttgaggtgg gagcggggct  2244 gggaggaagg gatgggcccc gccttcctgg gcagcctttc cagcctcctg cctggctctc  2304 tcttcctacc ctccttccac atgtacataa actgtcactc taggaagaag acaaatgaca  2364 gattctgaca tttatatttg tgtattttcc tggatttata gtatgtgact tttctgatta  2424 atatatttaa tatattgaat aaaaaataga catgtagttg                        2464

<210> SEQ ID NO 2
<211> LENGTH: 598
<212> TYPE: PRT
<213> ORGANISM: Homo sapiens

<400> SEQUENCE: 2

Met Pro Cys Ile Gln Ala Gln Tyr Gly Thr Pro Ala Pro Ser Pro Gly

```
              1               5              10              15

Pro Arg Asp His Leu Ala Ser Asp Pro Leu Thr Pro Glu Phe Ile Lys
                    20                  25                  30

Pro Thr Met Asp Leu Ala Ser Pro Glu Ala Ala Pro Ala Ala Pro Thr
            35                  40                  45

Ala Leu Pro Ser Phe Ser Thr Phe Met Asp Gly Tyr Thr Gly Glu Phe
        50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
        130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
                180                 185                 190

Ser Pro Pro Thr Gly Pro Ser Pro Ser Leu Ala Gln Ser Pro Leu Lys
            195                 200                 205

Leu Phe Pro Ser Gln Ala Thr His Gln Leu Gly Glu Gly Glu Ser Tyr
        210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Pro Ser Glu Gly Arg Cys Ala Val Cys Gly Asp
                260                 265                 270

Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
        290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
                340                 345                 350

Pro Lys Gln Pro Pro Asp Ala Ser Pro Ala Asn Leu Leu Thr Ser Leu
            355                 360                 365

Val Leu Ala His Leu Asp Ser Gly Pro Ser Thr Ala Lys Leu Asp Tyr
        370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
                420                 425                 430
```

```
Ala Asp Gln Asp Leu Leu Leu Glu Ser Ala Phe Leu Glu Leu Phe Ile
        435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
        515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
        595

<210> SEQ ID NO 3
<211> LENGTH: 3427
<212> TYPE: DNA
<213> ORGANISM: Homo sapiens
<220> FEATURE:
<221> NAME/KEY: CDS
<222> LOCATION: (318)..(2111)

<400> SEQUENCE: 3
gctcgcgcac ggctccgcgg tcccttttgc ctgtccagcc ggccgcctgt ccctgctccc      60
tccctccgtg agtgtccggg ttcccttcgc ccagctctcc cacccctacc cgaccccggc     120
gcccgggctc ccagagggaa ctgcacttcg gcagagttga atgaatgaag agagacgcgg     180
agaactccta aggaggagat tggacaggct ggactcccca ttgcttttct aaaaatcttg     240
gaaactttgt ccttcattga attacgacac tgtccacctt taatttcctc gaaaacgcct     300
gtaactcggc tgaagcc atg cct tgt gtt cag gcg cag tat ggg tcc tcg       350
                    Met Pro Cys Val Gln Ala Gln Tyr Gly Ser Ser
                      1               5                  10 cct caa gga gcc agc ccc gct tct cag agc tac agt tac cac tct tcg       398
Pro Gln Gly Ala Ser Pro Ala Ser Gln Ser Tyr Ser Tyr His Ser Ser
            15                  20                  25 gga gaa tac agc tcc gat ttc tta act cca gag ttt gtc aag ttt agc       446
Gly Glu Tyr Ser Ser Asp Phe Leu Thr Pro Glu Phe Val Lys Phe Ser
        30                  35                  40 atg gac ctc acc aac act gaa atc act gcc acc act tct ctc ccc agc       494
Met Asp Leu Thr Asn Thr Glu Ile Thr Ala Thr Thr Ser Leu Pro Ser
    45                  50                  55 ttc agt acc ttt atg gac aac tac agc aca ggc tac gac gtc aag cca       542
Phe Ser Thr Phe Met Asp Asn Tyr Ser Thr Gly Tyr Asp Val Lys Pro
60                  65                  70                  75 cct tgc ttg tac caa atg ccc ctg tcc gga cag cag tcc tcc att aag       590
Pro Cys Leu Tyr Gln Met Pro Leu Ser Gly Gln Gln Ser Ser Ile Lys
                80                  85                  90
```

```
gta gaa gac att cag atg cac aac tac cag caa cac agc cac ctg ccc      638
Val Glu Asp Ile Gln Met His Asn Tyr Gln Gln His Ser His Leu Pro
             95                  100                 105 ccc cag tct gag gag atg atg ccg cac tcc ggg tcg gtt tac tac aag      686
Pro Gln Ser Glu Glu Met Met Pro His Ser Gly Ser Val Tyr Tyr Lys
        110                 115                 120 ccc tcc tcg ccc ccg acg ccc acc acc ccg ggc ttc cag gtg cag cac      734
Pro Ser Ser Pro Pro Thr Pro Thr Thr Pro Gly Phe Gln Val Gln His
        125                 130                 135 agc ccc atg tgg gac gac ccg gga tct ctc cac aac ttc cac cag aac      782
Ser Pro Met Trp Asp Asp Pro Gly Ser Leu His Asn Phe His Gln Asn
140                 145                 150                 155 tac gtg gcc act acg cac atg atc gag cag agg aaa acg cca gtc tcc      830
Tyr Val Ala Thr Thr His Met Ile Glu Gln Arg Lys Thr Pro Val Ser
                160                 165                 170 cgc ctc tcc ctc ttc tcc ttt aag caa tcg ccc cct ggc acc ccg gtg      878
Arg Leu Ser Leu Phe Ser Phe Lys Gln Ser Pro Pro Gly Thr Pro Val
            175                 180                 185 tct agt tgc cag atg cgc ttc gac ggg ccc ctg cac gtc ccc atg aac      926
Ser Ser Cys Gln Met Arg Phe Asp Gly Pro Leu His Val Pro Met Asn
        190                 195                 200 ccg gag ccc gcc ggc agc cac cac gtg gtg gac ggg cag acc ttc gct      974
Pro Glu Pro Ala Gly Ser His His Val Val Asp Gly Gln Thr Phe Ala
        205                 210                 215 gtg ccc aac ccc att cgc aag ccc gcg tcc atg ggc ttc ccg ggc ctg     1022
Val Pro Asn Pro Ile Arg Lys Pro Ala Ser Met Gly Phe Pro Gly Leu
220                 225                 230                 235 cag atc ggc cac gcg tct cag ctg ctc gac acg cag gtg ccc tca ccg     1070
Gln Ile Gly His Ala Ser Gln Leu Leu Asp Thr Gln Val Pro Ser Pro
                240                 245                 250 ccg tcg cgg ggc tcc ccc tcc aac gag ggg ctg tgc gct gtg tgt ggg     1118
Pro Ser Arg Gly Ser Pro Ser Asn Glu Gly Leu Cys Ala Val Cys Gly
            255                 260                 265 gac aac gcg gcc tgc caa cac tac ggc gtg cgc acc tgt gag ggc tgc     1166
Asp Asn Ala Ala Cys Gln His Tyr Gly Val Arg Thr Cys Glu Gly Cys
        270                 275                 280 aaa ggc ttc ttt aag cgc aca gtg caa aaa aat gca aaa tac gtg tgt     1214
Lys Gly Phe Phe Lys Arg Thr Val Gln Lys Asn Ala Lys Tyr Val Cys
        285                 290                 295 tta gca aat aaa aac tgc cca gtg gac aag cgt cgc cgg aat cgc tgt     1262
Leu Ala Asn Lys Asn Cys Pro Val Asp Lys Arg Arg Arg Asn Arg Cys
300                 305                 310                 315 cag tac tgc cga ttt cag aag tgc ctg gct gtt ggg atg gtc aaa gaa     1310
Gln Tyr Cys Arg Phe Gln Lys Cys Leu Ala Val Gly Met Val Lys Glu
                320                 325                 330 gtg gtt cgc aca gac agt tta aaa ggc cgg aga ggt cgt ttg ccc tcg     1358
Val Val Arg Thr Asp Ser Leu Lys Gly Arg Arg Gly Arg Leu Pro Ser
            335                 340                 345 aaa ccg aag agc cca cag gag ccc tct ccc cct tcg ccc ccg gtg agt     1406
Lys Pro Lys Ser Pro Gln Glu Pro Ser Pro Pro Ser Pro Pro Val Ser
        350                 355                 360 ctg atc agt gcc ctc gtc agg gcc cat gtc gac tcc aac ccg gct atg     1454
Leu Ile Ser Ala Leu Val Arg Ala His Val Asp Ser Asn Pro Ala Met
365                 370                 375 acc agc ctg gac tat tcc agg ttc cag gcg aac cct gac tat caa atg     1502
Thr Ser Leu Asp Tyr Ser Arg Phe Gln Ala Asn Pro Asp Tyr Gln Met
380                 385                 390                 395 agt gga gat gac acc cag cat atc cag caa ttc tat gat ctc ctg act     1550
Ser Gly Asp Asp Thr Gln His Ile Gln Gln Phe Tyr Asp Leu Leu Thr
                400                 405                 410
```

```
                                                -continued ggc tcc atg gag atc atc cgg ggc tgg gca gag aag atc cct ggc ttc      1598
Gly Ser Met Glu Ile Ile Arg Gly Trp Ala Glu Lys Ile Pro Gly Phe
            415                 420                 425 gca gac ctg ccc aaa gcc gac caa gac ctg ctt ttt gaa tca gct ttc      1646
Ala Asp Leu Pro Lys Ala Asp Gln Asp Leu Leu Phe Glu Ser Ala Phe
        430                 435                 440 tta gaa ctg ttt gtc ctt cga tta gca tac agg tcc aac cca gtg gag      1694
Leu Glu Leu Phe Val Leu Arg Leu Ala Tyr Arg Ser Asn Pro Val Glu
    445                 450                 455 ggt aaa ctc atc ttt tgc aat ggg gtg gtc ttg cac agg ttg caa tgc      1742
Gly Lys Leu Ile Phe Cys Asn Gly Val Val Leu His Arg Leu Gln Cys
460                 465                 470                 475 gtt cgt ggc ttt ggg gaa tgg att gat tcc att gtt gaa ttc tcc tcc      1790
Val Arg Gly Phe Gly Glu Trp Ile Asp Ser Ile Val Glu Phe Ser Ser
                480                 485                 490 aac ttg cag aat atg aac atc gac att tct gcc ttc tcc tgc att gct      1838
Asn Leu Gln Asn Met Asn Ile Asp Ile Ser Ala Phe Ser Cys Ile Ala
            495                 500                 505 gcc ctg gct atg gtc aca gag aga cac ggg ctc aag gaa ccc aag aga      1886
Ala Leu Ala Met Val Thr Glu Arg His Gly Leu Lys Glu Pro Lys Arg
        510                 515                 520 gtg gaa gaa ctg caa aac aag att gta aat tgt ctc aaa gac cac gtg      1934
Val Glu Glu Leu Gln Asn Lys Ile Val Asn Cys Leu Lys Asp His Val
    525                 530                 535 act ttc aac aat ggg ggg ttg aac cgc ccc aat tat ttg tcc aaa ctg      1982
Thr Phe Asn Asn Gly Gly Leu Asn Arg Pro Asn Tyr Leu Ser Lys Leu
540                 545                 550                 555 ttg ggg aag ctc cca gaa ctt cgt acc ctt tgc aca cag ggg cta cag      2030
Leu Gly Lys Leu Pro Glu Leu Arg Thr Leu Cys Thr Gln Gly Leu Gln
                560                 565                 570 cgc att ttc tac ctg aaa ttg gaa gac ttg gtg cca ccg cca gca ata      2078
Arg Ile Phe Tyr Leu Lys Leu Glu Asp Leu Val Pro Pro Pro Ala Ile
            575                 580                 585 att gac aaa ctt ttc ctg gac act tta cct ttc taagacctcc tcccaagcac    2131
Ile Asp Lys Leu Phe Leu Asp Thr Leu Pro Phe
        590                 595 ttcaaaggaa ctggaatgat aatggaaact gtcaagaggg ggcaagtcac atgggcagag    2191
atagccgtgt gagcagtctc agctcaagct gcccccatt tctgtaaccc tcctagcccc     2251
cttgatccct aaagaaaaca aacaaacaaa caaaaactgt tgctatttcc taacctgcag    2311
gcagaacctg aaagggcatt ttggctccgg ggcatcctgg atttagaaca tggactacac    2371
acaatacagt ggtataaact ttttattctc agtttaaaaa tcagtttgtt gttcagaaga    2431
aagattgcta taaggtataa tgggaaatgt ttggccatgc ttggttgttg cagttcagac    2491
aaatgtaaca cacacacaca tacacacaca cacacacaca gagacacatc ttaaggggac    2551
ccacaagtat tgcccttaa caagacttca agttttctg ctgtaaagaa agctgtaata      2611
tatagtaaaa ctaaatgttg cgtgggtggc atgagttgaa gaaggcaaag gcttgtaaat    2671
ttacccaatg cagtttggct tttttaaatta ttttgtgcct atttatgaat aaatattaca   2731
aattctaaaa gataagtgtg tttgcaaaaa aaaagaaaat aaatacataa aaaagggaca    2791
agcatgttga ttctaggttg aaaatgttat aggcacttgc tacttcagta atgtctatat    2851
tatataaata gtatttcaga cactatgtag tctgttagat tttataaaga ttggtagtta    2911
tctgagctta aacattttct caattgtaaa ataggtgggc acaagtatta cacatcagaa    2971
aatcctgaca aaagggacac atagtgtttg taacaccgtc caacattcct tgtttgtaag    3031
```

-continued

```
tgttgtatgt accgttgatg ttgataaaaa gaaagtttat atcttgatta ttttgttgtc    3091
taaagctaaa caaaacttgc atgcagcagc ttttgactgt ttccagagtg cttataatat    3151
acataactcc ctggaaataa ctgagcactt tgaattttt  ttatgtctaa aattgtcagt    3211
taatttatta ttttgtttga gtaagaattt taatattgcc atattctgta gtattttct     3271 ttgtatattt ctagtatggc acatgatatg agtcactgcc ttttttcta tggtgtatga     3331 cagttagaga tgctgatttt ttttctgata aattctttct ttgagaaaga caattttaat    3391
gtttacaaca ataaaccatg taaatgaaaa aaaaaa                              3427
```

<210> SEQ ID NO 4
<211> LENGTH: 598
<212> TYPE: PRT
<213> ORGANISM: Homo sapiens

<400> SEQUENCE: 4

```
Met Pro Cys Val Gln Ala Gln Tyr Gly Ser Ser Pro Gln Gly Ala Ser
  1               5                  10                  15

Pro Ala Ser Gln Ser Tyr Ser Tyr His Ser Ser Gly Glu Tyr Ser Ser
             20                  25                  30

Asp Phe Leu Thr Pro Glu Phe Val Lys Phe Ser Met Asp Leu Thr Asn
         35                  40                  45

Thr Glu Ile Thr Ala Thr Thr Ser Leu Pro Ser Phe Ser Thr Phe Met
     50                  55                  60

Asp Asn Tyr Ser Thr Gly Tyr Asp Val Lys Pro Pro Cys Leu Tyr Gln
 65                  70                  75                  80

Met Pro Leu Ser Gly Gln Gln Ser Ser Ile Lys Val Glu Asp Ile Gln
                 85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300
```

```
Cys Pro Val Asp Lys Arg Arg Asn Arg Cys Gln Tyr Cys Arg Phe
305                 310                 315                 320

Gln Lys Cys Leu Ala Val Gly Met Val Lys Glu Val Val Arg Thr Asp
            325                 330                 335

Ser Leu Lys Gly Arg Arg Gly Arg Leu Pro Ser Lys Pro Lys Ser Pro
        340                 345                 350

Gln Glu Pro Ser Pro Pro Ser Pro Pro Val Ser Leu Ile Ser Ala Leu
    355                 360                 365

Val Arg Ala His Val Asp Ser Asn Pro Ala Met Thr Ser Leu Asp Tyr
370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
ccactttggg aaggaagatg ct                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence
```

```
<400> SEQUENCE: 6
actttcggat gacctccaga ga                                                  22

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Probe Sequence
<220> FEATURE:
<221> NAME/KEY: misc_binding
<222> LOCATION: (1)
<223> OTHER INFORMATION: Label FAM
<220> FEATURE:
<221> NAME/KEY: misc_binding
<222> LOCATION: (30)
<223> OTHER INFORMATION: Label TAMRA

<400> SEQUENCE: 7
atgtacagca gttctacgac ctgctctccg                                          30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
agcacaggct acgacgtcaa                                                     20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
tcttctacct taatggagga ctgc                                                24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Probe Sequence

<400> SEQUENCE: 10
ttgtaccaaa tgcccctgtc cgga                                                24

<210> SEQ ID NO 11
<211> LENGTH: 63
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
ggccagtgaa ttgtaatacg actcactata gggaggcggt tttttttttt tttttttttt         60
ttt                                                                       63
```

```
<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tcacccacac tgtgcccatc tacga                                           25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
cagcggaacc gctcattgcc aatgg                                           25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:Artificially
      Synthesized Probe Sequence
<220> FEATURE:
<221> NAME/KEY: misc_binding
<222> LOCATION: (1)
<223> OTHER INFORMATION: Label FAM
<220> FEATURE:
<221> NAME/KEY: misc_binding
<222> LOCATION: (7)
<223> OTHER INFORMATION: Label TAMRA

<400> SEQUENCE: 14
atgccctccc ccatgccatc ctgcgt                                          26
```